(12) United States Patent
Timmers et al.

(10) Patent No.: US 8,034,945 B2
(45) Date of Patent: *Oct. 11, 2011

(54) 4-PHENYL-5-OXO-1,4,5,6,7,8-HEXAHYDROQUINOLINE DERIVATIVES AS MEDICAMENTS FOR THE TREATMENT OF INFERTILITY

(75) Inventors: Cornelis Marius Timmers, Oss (NL); Willem Frederik Karstens, Oss (NL); Pedro Manuel Grima Poveda, Oss (NL)

(73) Assignee: N.V. Organon, Oss (NL)

( * ) Notice: Subject to any disclaimer, the term of this patent is extended or adjusted under 35 U.S.C. 154(b) by 826 days.

This patent is subject to a terminal disclaimer.

(21) Appl. No.: 11/912,746

(22) PCT Filed: May 2, 2006

(86) PCT No.: PCT/EP2006/061976
§ 371 (c)(1),
(2), (4) Date: Oct. 26, 2007

(87) PCT Pub. No.: WO2006/117370
PCT Pub. Date: Nov. 9, 2006

(65) Prior Publication Data
US 2008/0300270 A1 Dec. 4, 2008

(30) Foreign Application Priority Data
May 4, 2005 (EP) .................................. 05103738

(51) Int. Cl.
C07D 215/04 (2006.01)
C07D 215/00 (2006.01)
C07D 413/00 (2006.01)
(52) U.S. Cl. .................... 546/173; 546/165; 544/128
(58) Field of Classification Search .............. 546/165, 546/173; 544/128
See application file for complete search history.

(56) References Cited

U.S. PATENT DOCUMENTS

| 5,455,253 A * | 10/1995 | Ohnmacht et al. ............. 514/311 |
| 5,622,964 A * | 4/1997 | Ohnmacht et al. ............. 514/311 |
| 6,087,503 A | 7/2000 | Furuya et al. |
| 6,194,428 B1 | 2/2001 | Urbahns et al. |
| 2008/0262033 A1 | 10/2008 | Karstens et al. |
| 2008/0275042 A1 | 11/2008 | Poveda et al. |
| 2009/0215773 A1 | 8/2009 | Van Straten et al. |

FOREIGN PATENT DOCUMENTS

| DE | 1070162 | 12/1959 |
| EP | 0 755 931 | 1/1997 |
| JP | 2003026630 | 1/2003 |
| WO | WO 94/08966 | 4/1994 |
| WO | WO 96/06610 | 3/1996 |
| WO | WO 00/08015 | 2/2000 |
| WO | WO 00/78768 | 12/2000 |
| WO | WO 02/09706 | 2/2002 |
| WO | WO 03/004028 | 1/2003 |
| WO | WO 2004/056779 | 7/2004 |

OTHER PUBLICATIONS

Altmayer, et al., "Propofol Binding to Human Blood Proteins", *Arzneim.-Forsch./Drug Res.* (1995) 45: 1053-1056.
Anelli et al., "Smiles Rearrangement as a Tool for the Preparation of 5-[(2-Hydroxyacyl)amino]-2,4,6-triiodo-1,3-benzenedicarboxamides: Main Pathway and Side Reactions," *Tetrahedron* (1997) 53:11919-11928.
Aranyos, et al., "An Application of the Stille Coupling for the Preparation of Arylated Phthalonitriles and Phthalocyanines", *Acta Chem. Scand.* (1999) 53: 714-720.
Bahner, et al., "Halogenated Aminobenzaldehydes and Aminostyrylquinolines", *J. Org. Chem*, 25 (1960) 2053-2055.
Baker, William R. "Alkoxide-Accelerated Smiles Rearrangements. Synthesis of N-(2-Hydroxyethyl)anilines from N-(2-Hydroxyethyl)(aryloxy)acetamides," *J. Org. Chem.* (1983) 48: 5140-5143.
Bierbaum et al., "Hypotensive 1,2,4-Benzothiadiazines," *J. Med. Chem.* (1963) 6: 272-275.
Claiborne et al., "Orally Efficacious NR2B-Selective NMDA Receptor Antagonists," *Bioorg. & Med. Chem. Lett.* 13:697-700, 2003.
Crich, et.al., "Enantiospecific Synthesis with Amino Acids. Part 2. a-Alkylation of Tryptophan: A Chemical and Computational Investigation of Cyclic Tryptophan Tautomers", *J. Chem. Soc. Perkin Trans.* 2 (1992) 2233-2240.

(Continued)

*Primary Examiner* — Nizal Chandrakumar
(74) *Attorney, Agent, or Firm* — Janet E. Fair; John C. Todaro

(57) ABSTRACT

The invention relates to a 4-phenyl-5-oxo-1,4,5,6,7,8-hexahydroquinoline derivative according to Formula (I), wherein the substituents are defined as in the description, or a pharmaceutically salt thereof. The compounds of this invention are potent FSH receptor activators and may be used for treating fertility disorders in e.g. controlled ovarian hyperstimulation and IVF procedures.

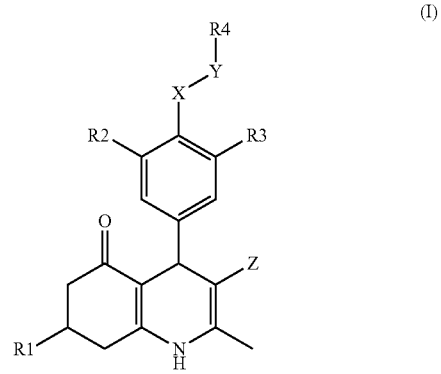

11 Claims, 1 Drawing Sheet

OTHER PUBLICATIONS

Devroey, et al., "Successful in-vitro fertilisation and embryo transfer after treatment with recombinant human FSH", *Lancet* 339 (1992) 1170-1171.

Dondoni et al., "Two- and Three-Component Hantzsch Reaction Using C-Glycosylated Reagents. Approach to the Asymmetric Synthesis of 1,4-Diyhydropyridines", *Synlett* (2002) 89-92.

Dorrington & Armstrong, "Effects of FSH on Gonadal Functions", *Recent Prog. Horm. Res.*, 35 (1979) 301-342.

Dow, et al., "Discovery of a Novel Series of 6-Azauracil-Based Thyroid Hormone Receptor Ligands:Potent, TRβ Subtype-Selective Thyromimetics", *Bioorg. & Med. Chem. Lett.* 13 (2003) 379-382.

Drizin, et al., "Structure-Activity Studies for a Novel Series of Tricyclic Dihydropyrimidines as KATP Channel Openers (KCOs)", *Bioorg. &Med. Chem. Lett.* 12 (2002) 1481-1484.

Eisner, et al., "The Chemistry Of Dihydropyridines", *Chem. Rev.* 72 (1972) 1-42.

Fisher, et al., "Heteroatom-Directed Metalation. Lithiation of N-Propenylbenzamides and N-Propenyl-o -toluamides. Novel Routes to Ortho-Substituted Primary Benzamide Derivatives and N-Unsubstituted Isoquinolin-1(2H)-ones", *J. Org. Chem.* 57 (1992) 2700-2705.

Fukuyama, et al., "2,4-Dinitrobenzenesulfonamides: A Simple and Practical Method for the Preparation of a Variety of Secondary Amines and Diamines", *Tetrahedron Lett.* 38 (1997) 5831-5834.

Greiner, A., "TDA-1 Catalysis in Smiles Rearrangement of N-Arylphenoxyamides. Accelerating Effect of the 2,4,6-Trichloro Substitution," *Tetrahedron Lett.* 30:931-934, 1989.

Guilford, et al., "Synthesis, Characterization, and Structure-Activity Relationships of Amidine-Substituted (Bis)benzylidene-Cycloketone Olefin Isomers as Potent and Selective Factor Xa Inhibitors," *J. Med. Chem.* 42:5415-5425, 1999.

Guo, et al., "Enantioselective Addition of Diethylzinc to Benzaldehyde Catalyzed by Chiral Titanate Complexes with Helical Ligands", *Tetrahedron* 53 (1997) 4145-4158.

Harvey, et al., "o-Nitroaniline Derivatives. Part 11. 4- and 7-Amino-IH-benzimidazole 3-Oxides", *J. Chem. Soc. Perkin Trans.* 1 (1988) 1939-1943.

Insler, V., "Gonadotropin Therapy: New Trends and Insights", *Int. J. Fertil.*, 33 (1988) 85-97.

Jia, et al., "Expression of Human Luteinizing Hormone (LH) Receptor: Interaction with LH and Chorionic Gonadotropin from Human but not Equine, Rat, and Ovine Species", *Mol. Endocrinol.* 5 (1991) 759-768.

Kansal, et al., "Diuretic Agents: Synthesis of 1,2-Disubstituted 7-Sulphamoylbenzimidazole-5-Carboxylic Acids," *Indian J. Chem.* 18B:88-90, 1979.

Katsumi, et al., "Studies on Styrene Derivatives. I. Synthesis and Antiinflammatory Activities of a-Benzylidene-γ-butyrolactone Derivatives", *Chem. Pharm. Bull.* 34 (1986) 121-129.

Kesten, et al., "Synthesis and Antimalarial Properties of 1-Imino Derivatives of 7-Chloro-3-substituted-3,4-dihydro-1,9(2H,10H)-acridinediones and Related Structures", *J. Med. Chem.* 35 (1992) 3429-3447.

Krohn, et al., "Total Synthesis of Angucyclines. Part 15: A Short Synthesis of (±)-6-Deoxybrasiliquinone B", *Tetrahedron* 56 (2000) 4753-4758.

Kuehne, et al., "1,4-Dihydrobenzoic Acid"; *Org. Synth. Coll.* 5 (1973) 400.

Kumar, et al., "Synthesis and Evaluation of Anticancer Benzoxazoles and Benzimidazoles Related to UK-1", *Bioorg. &Med. Chem.* 10 (2002) 3997-4004.

Lal, et al., "Regiospecific Oxidation by DDQ of Unhindered Alkyl Groups in Sterically Hindered Aromatic Amines", *Tetrahedron Lett.* 25 (1984) 2901-2904.

Langry, K.C., "Synthesis Of Imidazoquinolines And Imidazoisoquinolines From Azanaphthalene Carboxylic Acids", *Org. Prep. Proced. Int.* 26 (1994) 429-438.

Larget, et.al. "A Convenient Extension of the Wessely-Moser Rearrangement for the Synthesis of Substituted Alkylaminoflavones as Neuroprotective Agents in Vitro", *Bioorg. &Med. Chem. Lett.* 10 (2000) 835-838.

Lavilla, R., "Recent developments in the chemistry of dihydropyridines", *J. Chem. Soc., Perkin Trans.* 1 (2002) 1141-1156.

Loev, et al., "Hantzsch-Type Dihydropyridine Hypotensive Agents", *J. Med. Chem.* 17 (1974) 956-965.

Manchand, et al., "Synthesis of 3,4,5-Trimethoxybenzaldehyde", *Synth. Commun.* 20 (1990) 2659-2666.

Mariella, et al., "Synthesis of Some Aromatic Malononitriles", *J. Org. Chem.* 23 (1958) 120-121.

Mayer, et.al., "Über Carbocyclische Reduktone. Dihyrogpyogallol and Dihydrogallussäure", *Chem. Ber.* 88 (1955) 316-327.

McCarthy, et al., "Synthesis and Renal Vasodilator Activity of 2-Chlorodopamine and N-Substituted Derivatives," *J. Med. Chem.* 29: 1586-1590 (1986).

Miri, et al., "Synthesis and Calcium Channel Modulating Effects of Modified Hantzsch Nitrooxyalkyl 1,4-Dihydro-2,6-dimethyl-3-nitro-4-(pyridinyl or 2-trifluoromethylphenyl)-5-pyridinecarboxylates", *Drug Dev. Res.* 51 (2000) 225-232.

Mitchell, et al., "N-Bromosuccinimide-Dimethylformamide: A Mild, Selective Nuclear Monobromination Reagent for Reactive Aromatic Compounds", *J. Org. Chem.* 44 (1979) 4733-4735.

Morse, et al., "Hetrogeneity of Proteins in Commercial Preparations of Human Chorionic Gonadotropin (hCG) Demonstrated by Western Blotting", *Amer. J. Reproduct. Immunol. and Microbiology* 17 (1988) 134-140.

Navot, et al., "The Use of Follicle-Stimulating Hormone for Controlled Ovarian Hyperstimulation in In Vitro Fertilization", *J. In Vitro Fert. Embryo Transf.* 5 (1988) 3-13.

Nguyen, et al., "Hantzsch 1,4-Dihydropyridines Containing a Nitrooxyalkyl Ester Moiety to Study Calcium Channel Antagonist Structure—Activity Relationships and Nitric Oxide Release", *Drug Dev. Res.* 51 (2000) 233-243.

Nobel, D., "The Copper-Carbon Dioxide System, a New Mild and Selective Catalyst for the Methoxylation of Non-activated Aromatic Bromides", *J. Chem. Soc., Chem. Commun.* 4 (1993) 419-420.

Novak, et al, :Hydrolysis and $Fe^{2+}$-Induced Reduction of N-Aryl-O-pivaloylhydroxylamines: Aqueous Solution Chemistry of Model Carcinogens, *J. Org. Chem.* 53 (1988) 4762-4769.

Olijve, et al., "Molecular Biology and Biochemistry of Human Recombinant Follicle Stimulating Hormone (Puregon®)", *Mol. Hum. Reprod.* 2 (1996) 371-382.

Olson, et al., "A Dopamine Receptor Model and Its Application in the Design of a New Class of Rigid Pyrrolo[2,3-g]isoquinoline Antipsychotics", *J. Med. Chem.* 24 (1981) 1026-1034.

Raviña, et al., "Conformationally Constrained Butyrophenones with Affinity for Dopamine (D1, D2, D4) and Serotonin (5-HT2A, 5-HT2B, 5-HT2C) Receptors: Synthesis of Aminomethylbenzo[b]furanones and Their Evaluation as Antipsychotics", *J. Med. Chem.* 43 (2000) 4678-4693.

Sainani, et al., "Synthesis of 4-aryl-1,4,5,6,7,8-hexahydro-5-oxo-2,7,7-trimethylquinoline-3-carboxylates and amides", *Indian J. Chem.* 33B (1994) 526-531.

Sarma, et al., "Solid State Nuclear Bromination with N-Bromosuccinimide. Part 2. Experimental and theoretical studies of reactions with some substituted benzaldehydes", *J. Chem. Soc., Perkin Trans.* 2, (2000) 1119-1124.

Sarma, et al., "Solid State Nuclear Bromination with N-bromosuccinimide. Part 1. Experimental and theoretical studies on some substituted aniline, phenol and nitro aromatic compounds", *J. Chem. Soc., Perkin Trans.* 2, (2000) 1113-1118.

Shadyro et al, "Synthesis and Antiviral Activity of N-Acyl Derivatives of 4,6-Di-(*tert*-Butyl)-2-Aminophenol", *Pharm. Chem. J.*, 36 (2002) 410-412.

Sharma, et al., "Syntheses of Some Mannich Bases of Formyl & Other Substituted Phenols as Potential Spermicides", *Indian J. Chem.*, 20B (1981) 1010-1013.

Sharpe, R.M., "Intratesticular Control of Steroidogenesis", *Clin. Endocrinol.*, 33 (1990) 787-807.

Shilcrat, et al., "A New Regioselective Synthesis of 1,2,5-Trisubstituted 1H-Imidazoles and Its Application to the Development of Eprosartan ," *J. Org. Chem.* 62:8449-8454, 1997.

Sircar, et al., "Calcium Channel Blocking and Positive Inotropic Activities of Ethyl 5-Cyano-1,4-dihydro-6-methyl-2-[(phenylsulfonyl)methyl]-4-aryl-3-pyridine-carboxylate and Analogues. Synthesis and Structure-Activity Relationships", *J. Med. Chem.*, 34 (1991) 2248-2260.

Stratowa, et al., "Use of a luciferase reporter system for characterizing G-protein-linked receptors", *Curr. Opin. Biotechnol.*, 6 (1995) 574-581.

Theilacker, et al.,"Zur Konstitution dér Triacylmethane. II. Über das Bicyclo-[2,2,2]-octantrion-(2,6,7)", *Justus Liebig's Annalen der Chemie*, 570 (1950) 15-33.

Turconi, et al., "Synthesis of a New Class of 2,3-Dihydro-2-oxo-1H-benzimidazole-1-carboxylic Acid Derivatives as Highly Potent 5-HT3 Receptor Antagonists", *J. Med. Chem.*, 33 (1990) 2101-2108.

Vierhapper, et al., "Zur Sauerstoffoxidation von Kreosolderivaten in alkalisch-wäβriger Lösung", *Monatsh. Chem.*, 106 (1975) 1191-1201.

Visentin, et al. "Synthesis and Voltage-Clamp Studies of Methyl 1,4-Dihydro-2,6-dimethyl-5-nitro-4-(benzofurazanyl)pyridine-3-carboxylate Racemates and Enantiomers and of Their Benzofuroxanyl Analogues," *J. Med. Chem.*, 42 (1999) 1422-1427.

Vitolina, et al. "Synthesis and Study of the pharmacological activity of derivatives of condensed 1, 4-dihydropyridines," *Khimiko-Farmatsevticheskii Zhumal*, 15 (1981) 39-42.

Wadia, et al., "A Convenient Preparation of N-Alkyl and N-Arylamines by Smiles Rearrangement—Synthesis of Analogues of Diclofenac," *Synth. Commun.*, 33:2725-2736, 2003.

White, et al., "Resistance-Modifying Agents. 9. Synthesis and Biological Properties of Benzimidazole Inhibitors of the DNA Repair Enzyme Poly(ADP-ribose) Polymerase", *J. Med. Chem.*, 43 (2000) 4084-4097.

Wong, et al., "Identification of a Dihydropyridine as a Potent α1a Adrenoceptor-Selective Antagonist That Inhibits Phenylephrine-Induced Contraction of the Human Prostate", *J. Med. Chem.*, 41 (1998) 2643-2650.

Yagupolskii, et al., "Vasorelaxation by New Hybrid Compounds Containing Dihydropyridine and Pinacidil-Like Moieties", *J. Med. Chem.*, 42 (1999) 5266-5271.

Database CAPLUS Chemical Abstracts Service, Columbus, Ohio, US; XP-002288485 retrieved from STN accession No. 1802 Database accession No. 1981:497547.

XP-002369583 Retrieved from STN, Database Registry [Online] RN:330674-72-1, Apr. 10, 2001.

Search Report issued on May 12, 2005 in connection with PCT Intl. Appln. No. PCT/EP2005/052042.

Written Opinion issued on Nov. 4, 2007 in connection with PCT Intl. Appln. No. PCT/EP2005/052042.

International Preliminary Report on Patentability issued on Nov. 6, 2007 in connection with PCT Intl. Appln. No. PCT/EP2005/052042.

Search Report issued on Aug. 18, 2006 in connection with PCT Intl. Appln. No. PCT/EP2006/061972.

Written Opinion issued on Nov. 4, 2007 in connection with PCT Intl. Appln. No. PCT/EP2006/061972.

International Preliminary Report On Patentability issued on Nov. 6, 2007 in connection with PCT Intl. Appln. No. PCT/EP2006/061972.

Search Report issued on Jul. 5, 2006 in connection with PCT Intl. Appln. No. PCT/EP2006/061976.

Written Opinion issued on Nov. 4, 2007 in connection with PCT Intl. Appln. No. PCT/EP2006/061976.

International Preliminary Report on Patentability issued on Nov. 6, 2007 in connection with PCT Intl. Appln. No. PCT/EP2006/061976.

Search Report issued on Jul. 5, 2006 in connection with PCT Intl. Appln. No. PCT/EP2006/061978.

Written Opinion issued on Nov. 4, 2007 in connection with PCT Intl. Appln. No. PCT/EP2006/061978.

International Preliminary Report On Patentability issued on Nov. 6, 2007 in connection with PCT Intl. Appln. No. PCT/EP2006/061978.

Non-Final Rejection issued Jan. 8, 2010 in connection with US2009/0215773.

* cited by examiner

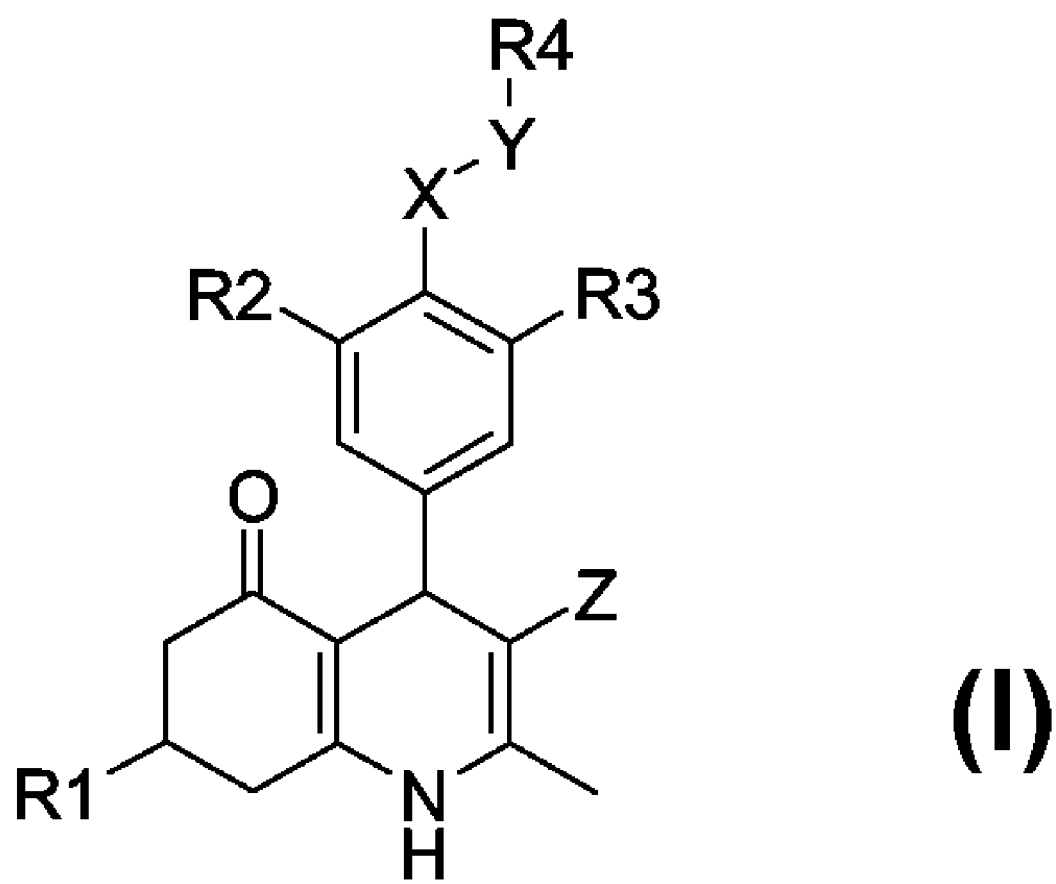
(I)

4-PHENYL-5-OXO-1,4,5,6,7,8-HEXAHYDROQUINOLINE DERIVATIVES AS MEDICAMENTS FOR THE TREATMENT OF INFERTILITY

CROSS REFERENCE TO RELATED APPLICATION

This application claims priority based on International Patent Application No. PCT/EP2006/061976, filed on May. 2, 2006.

FIELD OF THE INVENTION

The present invention relates to 4-phenyl-5-oxo-1,4,5,6,7,8-hexahydroquinoline derivatives, to pharmaceutical compositions comprising the same and to the use of said derivatives for the manufacture of medicaments for the treatment of fertility disorders.

Background Of The Invention

Gonadotropins serve important functions in a variety of bodily functions including metabolism, temperature regulation and the reproductive process. Gonadotropins act on specific gonadal cell types to initiate ovarian and testicular differentiation and steroidogenesis. The pituitary gonadotropin FSH (follicle stimulating hormone) for example plays a pivotal role in the stimulation of follicle development and maturation whereas LH (luteinizing hormone) induces ovulation (Sharp, R. M. Clin Endocrinol. 33:787-807, 1990; Dorrington and Armstrong, Recent Prog. Horm. Res. 35:301-342, 1979). Currently, FSH is applied clinically, for ovarian stimulation i.e. ovarian hyperstimulation for in vitro fertilisation (IVF) and induction of ovulation in infertile anovulatory women (Insler, V., Int. J. Fertility 33:85-97, 1988, Navot and Rosenwaks, J. Vitro Fert. Embryo Transfer 5:3-13, 1988), as well as for male hypogonadism and male infertility.

The gonadotropin FSH is released from the anterior pituitary under the influence of gonadotropin-releasing hormone and estrogens, and from the placenta during pregnancy. In the female, FSH acts on the ovaries promoting development of follicles and is the major hormone regulating secretion of estrogens. In the male, FSH is responsible for the integrity of the seminiferous tubules and acts on Sertoli cells to support gametogenesis. Purified FSH is used clinically to treat infertility in females and for some types of failure of spermatogenesis in males. Gonadotropins destined for therapeutic purposes can be isolated from human urine sources and are of low purity (Morse et al, Amer. J. Reproduct. Immunol. and Microbiology 17:143, 1988). Alternatively, they may be prepared as recombinant gonadotropins. Recombinant human FSH is available commercially and is being used in assisted reproduction (Olijve et al. Mol. Hum. Reprod. 2:371, 1996; Devroey et al. Lancet 339:1170, 1992).

The actions of the FSH hormone are mediated by a specific plasma membrane receptor that is a member of the large family of G-protein coupled receptors. These receptors consist of a single polypeptide with seven transmembrane domains and are able to interact with the Gs protein, leading to the activation of adenylate cyclase.

The FSH receptor is a highly specific target in the ovarian follicle growth process and is exclusively expressed in the ovary. Blocking of the receptor or inhibiting the signalling which is normally induced after FSH-mediated receptor activation will disturb follicle development and thus ovulation and fertility. Low molecular weight FSH antagonists could form the basis for new contraceptives, while low molecular weight FSH agonists may be used for the same clinical purposes as native FSH, i.e. for the treatment of infertility and for ovarian hyperstimulation on behalf of in vitro fertilisation.

Low molecular weight FSH mimetics with agonistic properties were disclosed in the International Application WO 2000/08015 (Applied Research Systems ARS Holding N.V.) and in WO 2002/09706 (Affymax Research Institute). Certain tetrahydroquinoline derivatives have recently been disclosed in the International Application WO 2003/004028 (AKZO NOBEL N.V.) as FSH modulating substances, either having agonistic or antagonistic properties. There remains a need for low molecular weight hormone mimetics that selectively activate the FSH receptor.

DETAILED DESCRIPTION OF THE INVENTION

To that aim the present invention provides 4-phenyl-5-oxo-1,4,5,6,7,8-hexahydroquinoline derivatives of general formula I

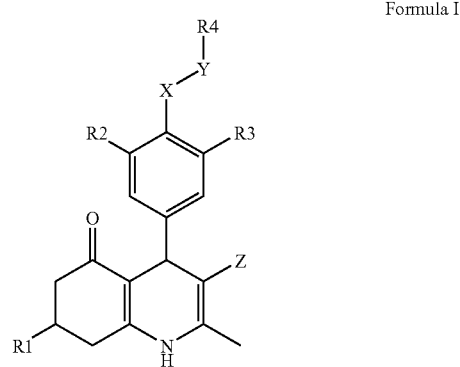

Formula I wherein
$R^1$ is (1-6C)alkyl, (2-6C)alkenyl or (2-6C)alkynyl;
$R^2$ is halogen, (1-4C)alkoxy, fluorinated (1-4C)alkoxy, (1-4C)alkyl, or fluorinated (1-4C)alkyl; or $R^2$ may be H when $R^3$ is $R^9,R^{10}$-aminosulfonyl;
$R^3$ is OH, $NO_2$, CN, fluorinated (1-4C)alkoxy, (1-4C)alkoxy(2-4C)alkoxy, hydroxy(2-4C)alkoxy, (1-4C)alkoxycarbonyl, (3-4C)alkenyloxycarbonyl, (1-4C)alkoxycarbonyloxy, (3-4C)alkenyloxycarbonyloxy, $R^7,R^8$-amino, $R^9,R^{10}$-amino, $R^9,R^{10}$-aminocarbonyl, $R^9,R^{10}$-aminosulfonyl or phenyl(1-4C)alkoxy, wherein the phenyl ring is optionally substituted with one or more substituents selected from hydroxy, amino, halogen, nitro, trifluoromethyl, cyano, (1-4C)alkyl, (2-4C)alkenyl, (2-4C)alkynyl, (1-4C)alkoxy, (di)(1-4C)alkylamino;
$R^4$ is $R^{11}$-phenyl or $R^{11}$-(2-5C)heteroaryl, wherein the phenyl or heteroaryl group is optionally further substituted with one or more substituents selected from hydroxy, amino, halogen, nitro, trifluoromethyl, cyano, (1-4C)alkyl, (1-4C)alkylthio, (1-4C)alkoxy, (2-4C)alkenyl, (2-4C)alkynyl;
$R^7$ is H, (1-4C)alkyl;
$R^8$ is (1-4C)alkylsulfonyl, (1-4C)alkylcarbonyl, (2-4C)alkenylcarbonyl, (3-6C)cycloalkylcarbonyl, (1-4C)alkoxycarbonyl, (3-4C)alkenyloxycarbonyl, (1-4C)alkoxy(1-4C)alkylcarbonyl, (3-4C)alkenyloxy(1-4C)alkylcarbonyl phenylcarbonyl, (2-5C)heteroarylcarbonyl, phenyl(1-4C)alkylcarbonyl, (2-5C)heteroaryl(1-4C)alkylcarbonyl, wherein the phenyl ring or the heteroaromatic ring is optionally substituted with one or more substituents selected from hydroxy, amino, halogen, nitro, trifluoromethyl, cyano, (1-4C)alkyl, (2-4C)alkenyl, (2-4C)alkynyl, (1-4C)alkoxy, (di)(1-4C)alkylamino;

$R^9$ and $R^{10}$ are independently selected from H, (1-6C)alkyl, (3-6C)cycloalkyl, (3-6C)cycloalkyl(1-4C)alkyl and (1-4C)alkoxy(2-4C)alkyl;

or $R^9$ and $R^{10}$ may be joined in a (4-6C)heterocycloalkenyl ring or a (2-6C)heterocycloalkyl ring, optionally substituted with one or more (1-4C)alkyl substituents;

$R^{11}$ is H, (1-6C)alkoxycarbonyl, $R^{12},R^{13}$-amino, (1-6C)alkylcarbonyl, (1-6C)alkylsulfonyl, $R^{14}$-oxy, $R^{14},R^{15}$-amino, $R^{14},R^{15}$-aminocarbonyl, $R^{14},R^{15}$ aminosulfonyl;

$R^{12}$ is H, (1-4C)alkyl;

$R^{13}$ is (1-4C)alkylsulfonyl, (1-4C)alkylcarbonyl, (3-6C)cycloalkylcarbonyl, (1-4C)alkoxycarbonyl, (3-4C)alkenyloxycarbonyl, (di)(1-4C)alkylamino-(1-4C)alkylcarbonyl, (2-6C)heterocycloalkyl(1-4C)alkylcarbonyl, (4-6C)heterocyclo-alkenyl(1-4C)alkylcarbonyl or (1-4C)alkoxy(1-4C)alkylcarbonyl;

$R^{14}$ and $R^{15}$ are independently selected from H, (1-6C)alkyl, (3-4C)alkenyl, (3-4C)alkynyl, (3-6C)cycloalkyl, (3-6C)cycloalkyl(1-4C)alkyl, hydroxy(2-4C)alkyl, amino(2-4C)alkyl, (1-4C)alkoxy(2-4C)alkyl, (di)(1-4C)alkylamino(2-4C)alkyl, (2-6C)heterocycloalkyl(2-4C)alkyl, (4-6C)heterocycloalkenyl(2-4C)alkyl, phenyl(1-4C)alkyl and (2-5C)heteroaryl(1-4C)alkyl;

X is O or $R^{16}$—N;
Y is $CH_2$, C(O) or $SO_2$;
Z is CN or $NO_2$;
$R^{16}$ is H, (1-4C)alkyl, (1-4C)alkylcarbonyl;
or a pharmaceutically acceptable salt thereof.

The 4-phenyl-5-oxo-1,4,5,6,7,8-hexahydroquinoline derivatives according to the present invention are potent FSH receptor activators and may be used for the same clinical purposes as native FSH since they behave like agonists, with the advantage that they may be prepared synthetically, may display altered stability properties and may be administered differently.

Thus, the FSH-receptor agonists of the present invention may be used for treating fertility disorders in e.g. controlled ovarian hyperstimulation and IVF procedures.

The terms (1-4C)alkyl and (1-6C)alkyl as used in the definition mean branched or unbranched alkyl groups having 1-4 and 1-6 carbon atoms, respectively, being methyl, ethyl, propyl, isopropyl, butyl, sec-butyl, isobutyl and tert-butyl, etc.

The term (2-4C)alkoxy(2-4C)alkyl means an alkoxy group, the alkyl group of which contains 2-4 carbon atoms, attached to an alkyl group having 2-4 carbon atoms.

The terms fluorinated (1-4C)alkyl and fluorinated (1-4C)alkoxy mean branched or unbranched alkyl and alkoxy groups, having 1-4 carbon atoms respectively and which are substituted with at least one fluorine atom.

The terms (2-4C)alkenyl, (3-4C)alkenyl and (2-6C)alkenyl mean branched or unbranched alkenyl groups having 2-4, 3-4 and 2-6 carbon atoms, respectively, such as ethenyl, 2-butenyl, and n-pentenyl.

The terms (2-4C)alkynyl mean branched or unbranched alkynyl groups having 2-4 carbon atoms, such as ethynyl and propynyl.

The term (3-6C)cycloalkyl means a cycloalkyl group having 3-6 carbon atoms, being cyclopropyl, cyclobutyl, cyclopentyl and cyclohexyl.

The term (3-6C)cycloalkyl(1-4C)alkyl means a (1-4C)alkyl group, as previously defined, substituted with a (3-6C)cycloalkylalkyl group, as previously defined.

The term (2-6C)heterocycloalkyl means a heterocycloalkyl group having 2-6 carbon atoms, preferably 3-5 carbon atoms, and at least including one heteroatom selected from N, O and/or S, which may be attached via a heteroatom if feasible, or a carbon atom. Preferred heteroatoms are N or O. Most preferred are piperidin-1-yl, morpholin-4-yl, pyrrolidin-1-yl and piperazin-1-yl.

The term (4-6C)heterocycloalkenyl means a heterocycloalkenyl group having 4-6 carbon atoms, preferably 5-6 carbon atoms, and at least including one heteroatom selected from N, O and/or S, which may be attached via a heteroatom if feasible, or a carbon atom. Preferred heteroatoms are N or O.

The term (2-5C)heteroaryl means a heteroaromatic group having 2-5 carbon atoms and at least one heteroatom selected from N, O and S, like imidazolyl, thiadiazolyl, pyridinyl, thienyl or furyl. Preferred heteroaryl groups are thienyl, furyl and pyridinyl.

The (2-5C)heteroaryl group may be attached via a carbon atom or a heteroatom, if feasible.

The term (di)(1-4C)alkylamino as used herein means an amino group, monosubstituted or disubstituted with alkyl groups, each of which contains 1-4 carbon atoms and has the same meaning as previously defined.

The term halogen means fluorine, chlorine, bromine or iodine, wherein chlorine, bromine or iodine are preferred.

The term pharmaceutically acceptable salt represents those salts which are, within the scope of medical judgement, suitable for use in contact for the tissues of humans and lower animals without undue toxicity, irritation, allergic response and the like, and are commensurate with a reasonable benefit/risk ratio. Pharmaceutically acceptable salts are well known in the art. They may be obtained during the final isolation and purification of the compounds of the invention, or separately by reacting the free base function with a suitable mineral acid such as hydrochloric acid, phosphoric acid, or sulfuric acid, or with an organic acid such as for example ascorbic acid, citric acid, tartaric acid, lactic acid, maleic acid, malonic acid, fumaric acid, glycolic acid, succinic acid, propionic acid, acetic acid, methanesulfonic acid, and the like. The acid function may be reacted with an organic or a mineral base, like sodium hydroxide, potassium hydroxide or lithium hydroxide.

One aspect of the invention relates to compounds of formula I, wherein $R^1$ is (1-6C)alkyl. More in particular, the invention relates to compounds wherein $R^1$ is (1-4C)alkyl.

Another aspect of the invention relates to compounds according to formula I wherein $R^2$ is halogen. More in particular, $R^2$ is Br.

In another aspect of this invention, $R^3$ in the compound of formula I is $R^9,R^{10}$-aminosulfonyl. In particular, $R^9$ and $R^{10}$ are independently (1-6C)alkyl.

Another aspect of this invention relates to compounds of formula I, wherein $R^4$ is $R^{11}$-phenyl or $R^{11}$-(2-5C)heteroaryl, the phenyl or heteroaryl group optionally being further substituted with one (1-4C)alkoxy. In particular, the invention relates to compounds wherein $R^{11}$ is H or $R^{12},R^{13}$-amino.

A further aspect of the invention relates to compounds of formula I, wherein X is O.

In another aspect, the invention concerns compounds of formula I, wherein Y is $CH_2$.

Another aspect of the invention relates to compounds wherein Z is CN.

Still another aspect of the invention concerns compounds wherein one or more of the specific definitions of the groups $R^1$ through $R^{16}$ and X, Y and Z as defined here above are combined in the definition of the 4-phenyl-5-oxo-1,4,5,6,7,8-hexahydroquinoline compound of formula I.

Yet another aspect of the invention concerns compounds according to Formula I which have an $EC_{50}$ in the binding assay of less than $10^{-8}$ M (as described in example 43).

Suitable general methods for the preparation of the compounds are outlined below.

In some cases, the $R^x$-groups comprising functional groups may need additional temporary protection depending on the type of reaction to be performed, which will be easily recognized by a person skilled in the art (see *Protective groups in*

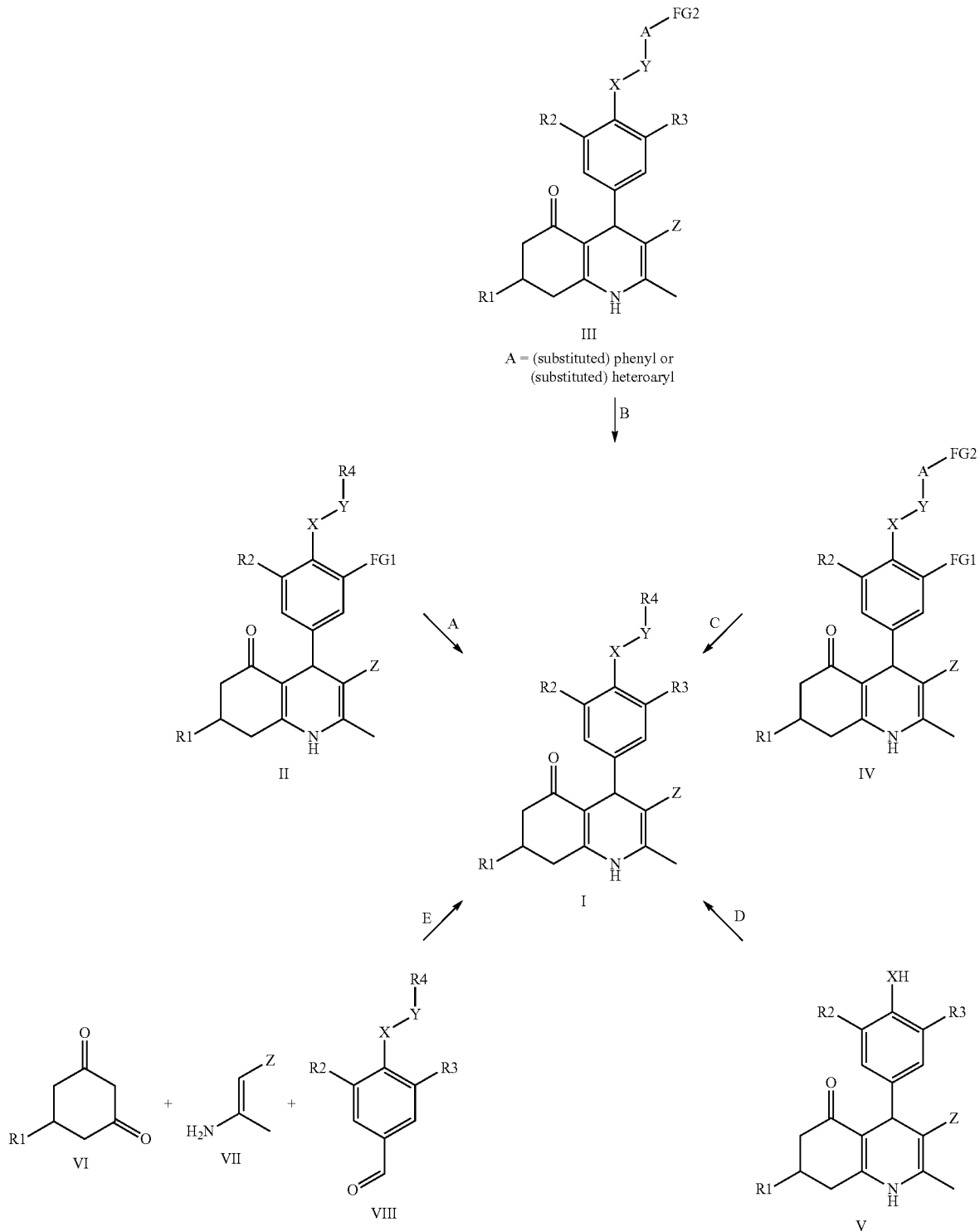

FG1 and FG2 are functional groups
A = (substituted) phenyl or (substituted) heteroaryl Organic Synthesis, T. W. Greene and P. G. M. Wuts, John Wiley & sons, Inc., New York, 1999).

The 4-phenyl-5-oxo-1,4,5,6,7,8-hexahydroquinoline derivatives of formula I, wherein $R^1$, $R^2$, $R^3$, $R^4$, X, Y and Z are as previously defined, may be prepared following several strategies. Method A starts from appropriately functionalised 4-phenyl-5-oxo-1,4,5,6,7,8-hexahydroquinoline derivatives of general structure II, wherein $R^1$, $R^2$, $R^4$, X, Y and Z are as previously defined and FG1 is a functional group, such as nitro, azido, (optionally protected) amino, (optionally protected) hydroxyl, carboxylic acid, sulfonyl chloride and the like, which may be converted to groups defined for $R^3$.

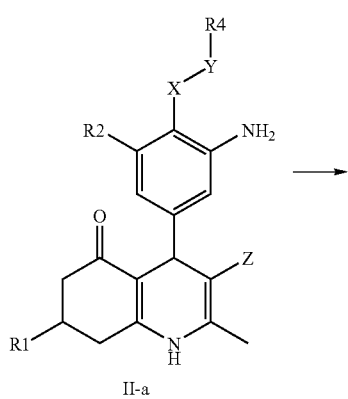

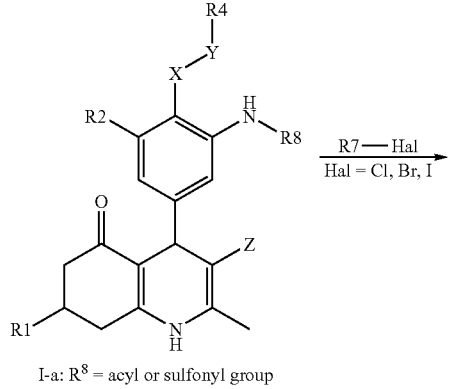

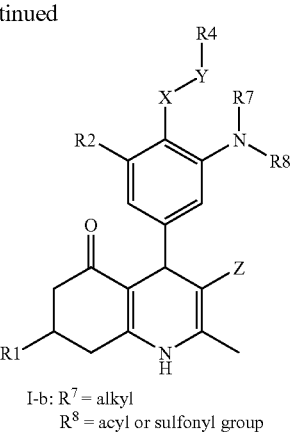

For example, N-acylation or N-sulfonylation of compounds of general formula II-a yields compounds of general formula I-a, wherein $R^1$, $R^2$, $R^4$, X, Y and Z are as previously defined, $R^7$ is H and $R^8$ is an acyl or sulfonyl group.

In a typical experiment, compounds II-a are reacted in a solvent, such as dichloromethane, N,N-dimethylformamide, dimethyl sulfoxide, ethanol, tetrahydrofuran, 1,4-dioxane, toluene, 1-methyl-pyrrolidin-2-one or pyridine with an appropriately substituted acyl halide, acid anhydride or sulfonyl halide in the presence of a base such as triethylamine, N,N-diisopropylethylamine (DiPEA) or pyridine, to give N-acylated or N-sulfonylated derivatives of formula I-a, respectively. Alternatively, N-acylated compounds of general formula I-a may be obtained by reaction of derivatives II-a with appropriately substituted carboxylic acids in the presence of a coupling reagent such as diisopropyl carbodiimide (DIC), (3-dimethylaminopropyl)-ethyl-carbodiimide (EDCI), O-(benzotriazol-1-yl)-N,N,N',N'-tetramethyluronium tetrafluoroborate (TBTU) or O-(7-azabenzotriazol-1-yl)-N,N,N',N'-tetramethyluronium hexafluorophosphate (HATU) and a tertiary amine base (e.g. DiPEA) in a solvent such as N,N-dimethylformamide or dichloromethane at ambient or elevated temperature.

Compounds of general formula I-b, wherein $R^1$, $R^2$, $R^4$, $R^8$, X, Y and Z are as previously defined and $R^7$ is a (1-4C)alkyl group, may be prepared by N-alkylation of derivatives I-a with appropriately substituted alkyl halides of general formula $R^7$-Hal. This reaction is typically conducted in the presence of a base such as potassium carbonate, cesium carbonate, sodium hydroxide or sodium hydride in suitable solvents such as dichloromethane, N,N-dimethylformamide, ethanol, dimethyl sulfoxide, tetrahydrofuran or 1,4-dioxane.

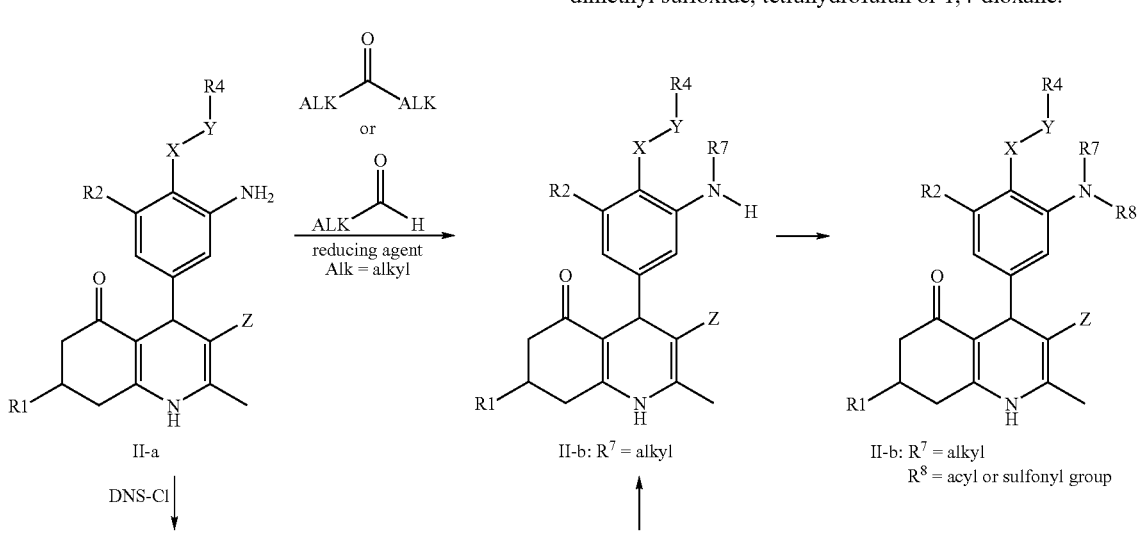

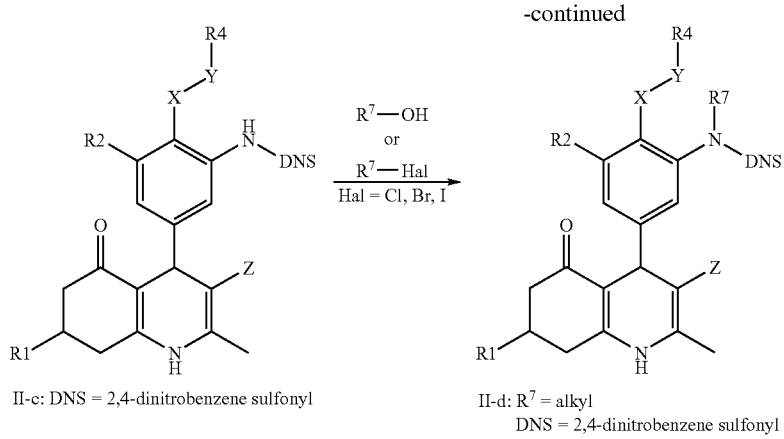

II-c: DNS = 2,4-dinitrobenzene sulfonyl

II-d: $R^7$ = alkyl
DNS = 2,4-dinitrobenzene sulfonyl

Alternatively, compounds of formula I-b may be obtained by reductive alkylation known in the art with alkyl aldehydes (e.g. acetaldehyde, (iso)butyraldehyde), acetone or butanone. Typically, compounds of general formula II-a are treated with the appropriate carbonyl compound and a reducing agent such as sodium cyanoborohydride or sodium triacetoxyborohydride in a suitable solvent such as methanol, ethanol, dichloromethane, N,N-dimethylformamide or mixtures thereof, optionally in the presence of acids such as acetic acid, to give compounds of general formula II-b. Compounds of general formula II-b may then be N-acylated or N-sulfonylated to give compounds of general formula I-b by the same methods described for the preparation of compounds of general formula I-a from II-a.

Compounds of general formula II-b may also be obtained via a 3 step sequence. First, compounds of formula II-a may be converted to 2,4-dinitrobenzenesulfonamide derivatives II-c by N-sulfonylation with 2,4-dinitrobenzenesulfonyl chloride (DNS-Cl).

The sulfonamide may be alkylated to give compounds of general formula II-d by using art known Mitsunobu reactions with appropriately substituted primary or secondary alcohols of formula $R^7$—OH ($R^7$=alkyl), triphenylphosphine (optionally resin bound) and a dialkyl azodicarboxylate in appropriate solvents such as 1,4-dioxane, tetrahydrofuran or dichloromethane at elevated or ambient temperature. Alternatively, the sulfonamide of general formula II-c may be alkylated using alkyl halides of formula $R^7$-Hal (Hal=Cl, Br, I) and a suitable base such as $K_2CO_3$ in a solvent such as N,N-dimethylformamide, tetrahydrofuran or 1,4-dioxane. Cleavage of the N—S sulfonamide bond with a primary amine such as propylamine in a suitable solvent such as dichloromethane then gives compounds of formula II-b. Alternatively, the N—S sulfonamide bond may be cleaved using mercaptoacetic acid and a tertiary amine base in a solvent such as dichloromethane. Precedence for these types of reactions can be found in literature. For example, see: Tetrahedron Lett. 38 (1997) 5831-5834, Bioorg. Med. Chem. Lett. 10 (2000) 835-838.

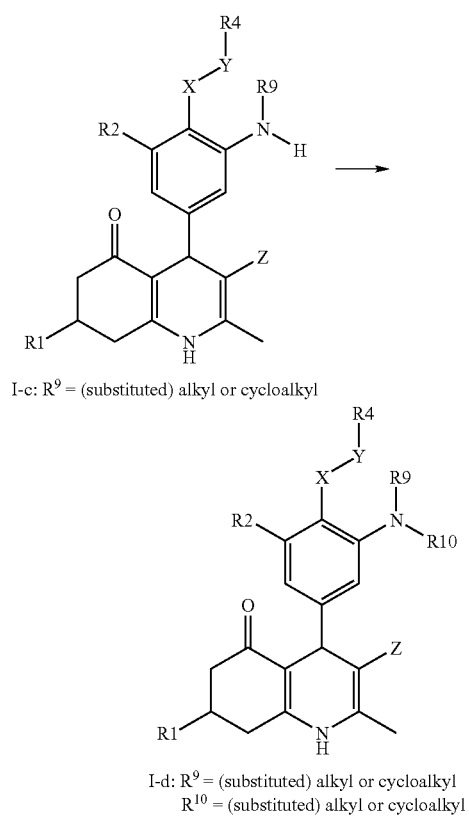

I-c: $R^9$ = (substituted) alkyl or cycloalkyl

I-d: $R^9$ = (substituted) alkyl or cycloalkyl
$R^{10}$ = (substituted) alkyl or cycloalkyl Using the same methods described for the preparation of derivatives II-b, compounds of general formula I-c are prepared, wherein $R^1$, $R^2$, $R^4$, $R^9$, X, Y and Z are as previously defined, by reacting compounds II-a with (substituted) alkyl aldehydes or (cyclic) ketones (e.g. propionaldehyde, cyclohexanone, acetone or acetaldehyde) under reductive conditions or by alkylation of derivatives II-c with $R^9$—OH or $R^9$-Hal, followed by removal of the DNS-group. Compounds I-c may be reductively alkylated again using appropriately substituted aldehydes or ketones to introduce $R^{10}$, yielding compounds of general formula I-d, wherein $R^1$, $R^2$, $R^4$, $R^9$, $R^{10}$, X, Y and Z are as previously defined. In some cases, the reductive alkylation of II-a may occur twice to yield compounds of general formula I-d wherein $R^9$=$R^{10}$ (e.g. when formaldehyde is used, $R^9$=$R^{10}$=methyl).

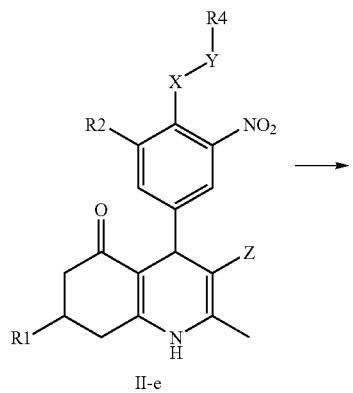
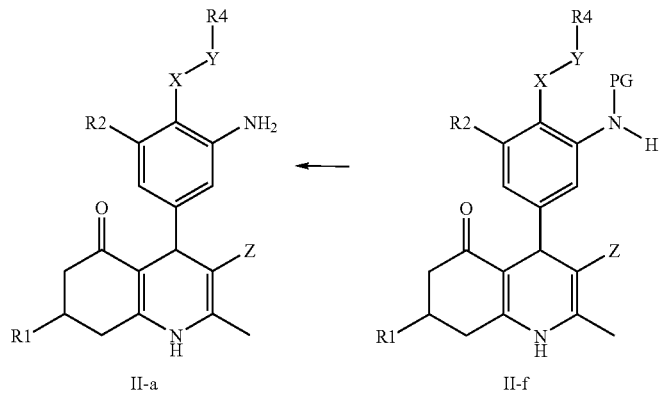

Compounds of general formula II-a may be obtained by the reduction of the nitro group in compounds of general formula II-e to the corresponding amino group. Typically, compounds II-e are treated with zinc dust and acetic acid in a suitable solvent such as THF or dioxane at temperatures between 0° C. and reflux temperature. Alternative methods include treatment with iron, $SnCl_2$, or hydrogen in the presence of a transition metal catalyst such palladium or platinum on charcoal, using methods and reagents well known to those skilled in the art. Alternatively, compounds of general formula II-a may be obtained by cleavage of known N-protecting groups (=PG in formula II-f) such as an allyloxycarbonyl (Alloc), fluoren-9-yl-methoxycarbonyl (Fmoc) or tert-butoxycarbonyl (Boc) group in compounds of general formula II-f to give the corresponding derivatives II-a. Related protective group manipulations can be found in *Protective groups in Organic Synthesis*, T. W. Greene and P. G. M. Wuts, John Wiley & sons, Inc., New York, 1999.

Carboxylic acid derivatives of general formula II-h, accessible by saponification of corresponding alkyl esters II-g, may be condensed with amines of general structure $R^9R^{10}NH$ using a coupling reagent as described before for the preparation of derivatives I-a from II-a to give compounds of formula I-e, wherein $R^1$, $R^2$, $R^4$, $R^9$, $R^{10}$, x, Y and Z are as previously defined. Alternatively, compounds of general formula II-h may be converted to the corresponding acid chlorides of general formula II-i by methods known in the art: treatment of carboxylic acids of general formula II-h with

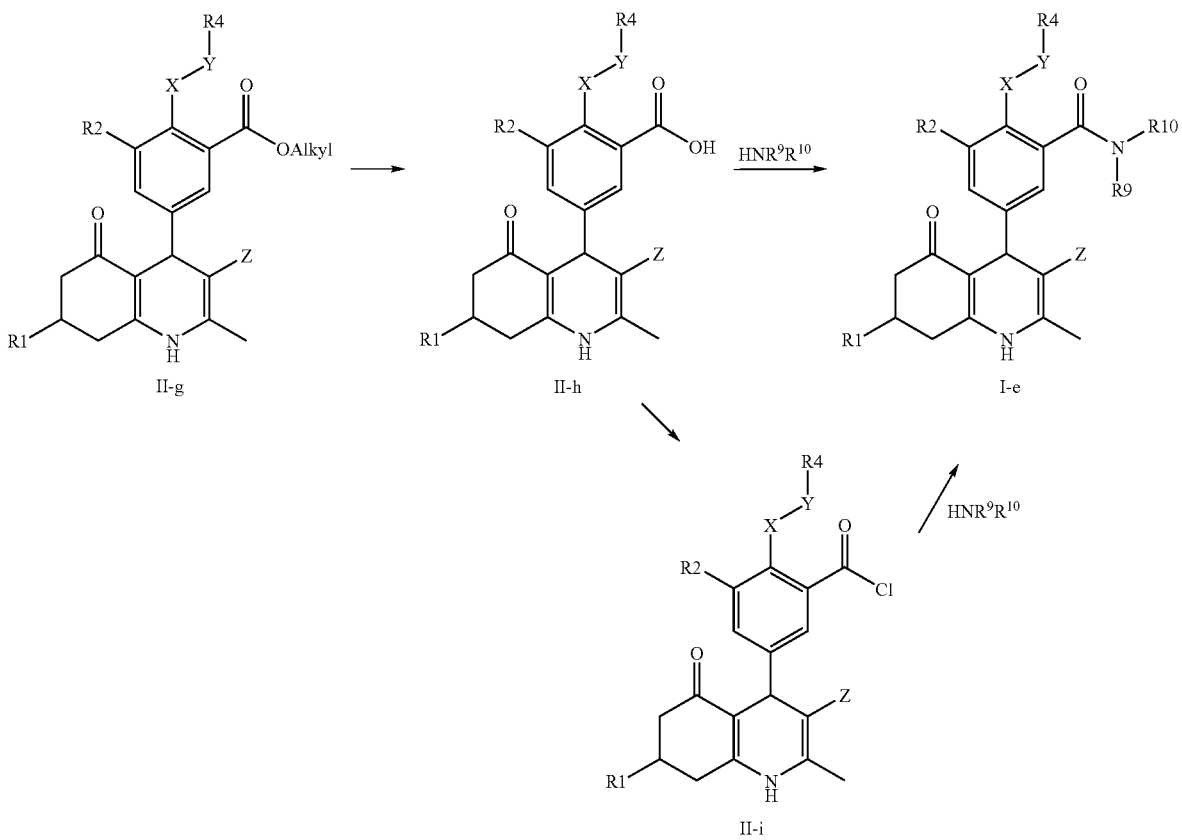

thionyl chloride or oxalyl chloride and DMF in a suitable solvent such as dichloromethane or toluene gives the corresponding acid chlorides II-i. Subsequent reaction with amines of general structure R⁹R¹⁰NH, optionally in the presence of a suitable tertiary amine base, yields compounds of general formula I-e.

Compounds of general formula I-f, wherein R¹, R², R⁴, X, Y and Z are as previously defined and R is cyano, may be obtained by dehydration of amides of general formula I-g with trifluoroacetic anhydride and a suitable base such as triethylamine or pyridine in a suitable solvent such as dichloromethane, 1,4-dioxane or tetrahydrofuran at 0° C. or ambient temperature. Related dehydrations of amides to give aryl nitrites can be found in literature, for example, see: Org. Prep. Proced. Int. 26 (1994) 429-438, Acta Chem. Scand. 53 (1999) 714-720, J. Org. Chem. 57 (1992) 2700-2705. Compounds of formula I-g are prepared according to the synthesis outlined for derivatives I-e.

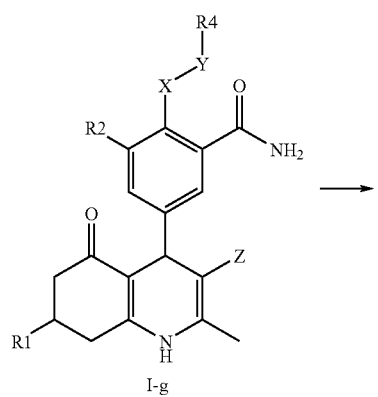

I-g

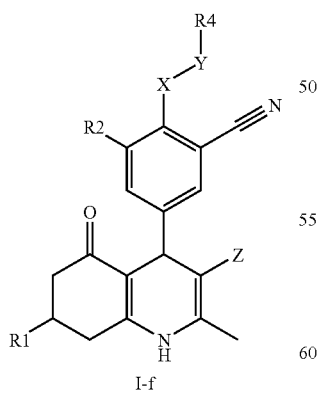

I-f

Compounds of general formula II-j wherein R¹, R², R⁴, X, Y and Z are as previously defined may be O-alkylated with (substituted) alkyl halides E-Hal (E=alkyl, fluorinated alkyl, alkoxyalkyl, hydroxyalkyl, (substituted) phenylalkyl or (substituted) heteroarylalkyl; Hal=Cl, Br, I) by treatment with a base such as potassium carbonate or cesium carbonate in suitable solvents such as N,N-dimethylformamide, acetone, tetrahydrofuran, 1,4-dioxane or 1-methyl-pyrrolidin-2-one to give compounds of general formula I-h, wherein R¹, R², R⁴, X, Y and Z are as previously defined and E is alkyl, fluorinated alkyl, alkoxyalkyl, hydroxyalkyl, (substituted) phenylalkyl or (substituted) heteroarylalkyl. Alternatively, Mitsunobu conditions as described for the conversion of derivatives II-c to compounds II-d may be used to effect this conversion.

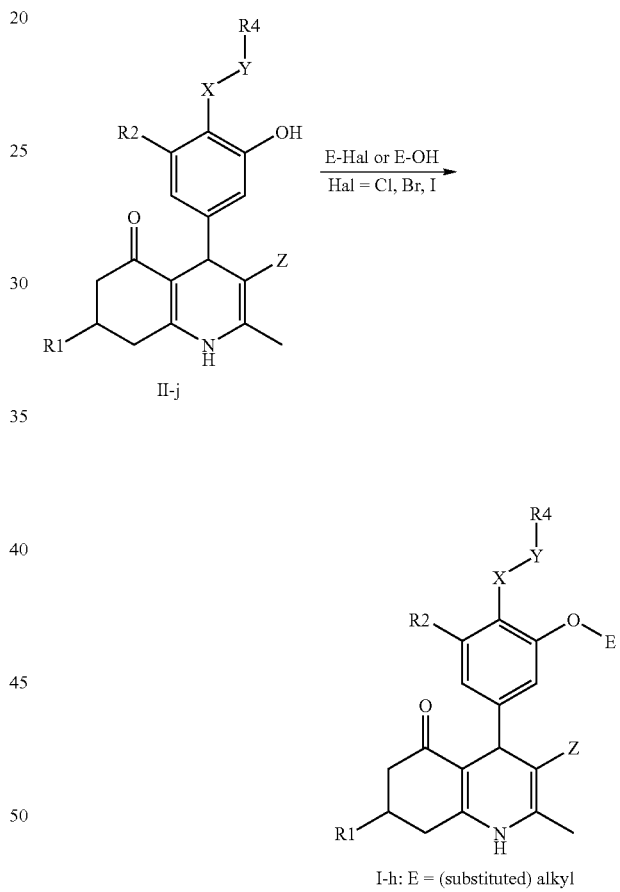

I-h: E = (substituted) alkyl

Compounds of general formula I may also be obtained by manipulation of functional groups FG2 in compounds of general formula III (method B). For example, functionalization of the amino group of compounds of general formula III-a in same manner as described for the conversion of derivatives II-a into I-a and I-b, yields compounds of general formula I-k, wherein R¹, R², R³, R¹², R¹³, X, Y and Z are as previously defined, A is a (substituted) phenyl or a (substituted) heteroaryl ring.

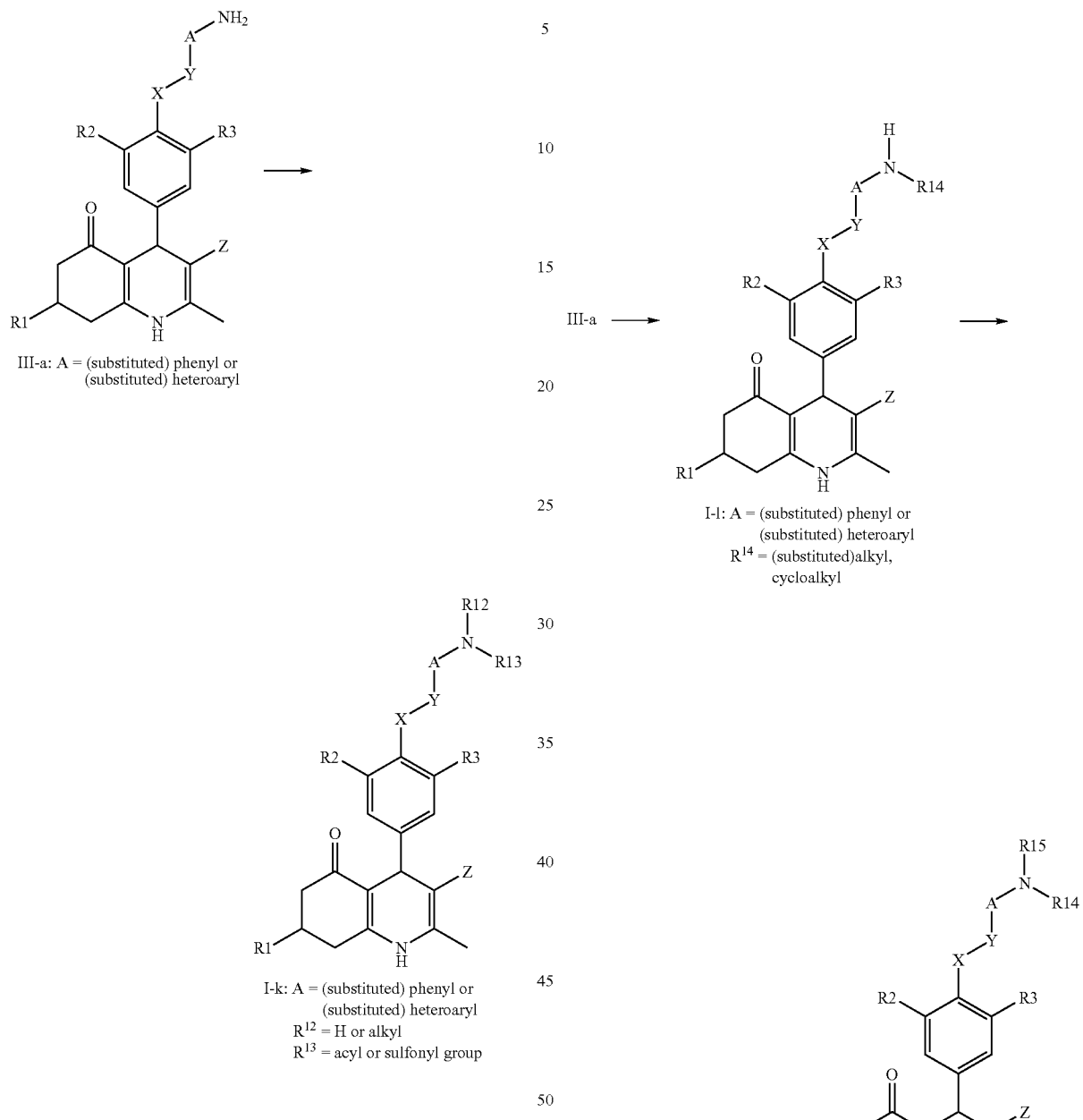

Compounds of general formula I-l, wherein $R^1$, $R^2$, $R^3$, $R^{14}$, X, Y and Z are as previously defined, $R^{15}$ is H and A is a (substituted) phenyl or a (substituted) heteroaryl ring, may be obtained by reductive alkylation of compounds of general formula III-a using the same methods described for the preparation of compounds II-b from II-a or by the 3 step sequence described for the preparation of derivatives II-b from II-a via II-c and II-d. Reductive alkylation of compounds I-l with aldehydes or ketones in the presence of sodium cyanoborohydride or sodium triacetoxyborohydride may afford compounds of general formula I-m, wherein $R^1$, $R^2$, $R^3$, $R^{14}$, $R^{15}$, X, Y and Z are as previously defined and A is a (substituted) phenyl or a (substituted) heteroaryl ring.

Compounds of general formula III-a may be prepared from compounds of general formula III-b or III-c in analogy to the preparation of compounds II-a from II-e or II-f, respectively.

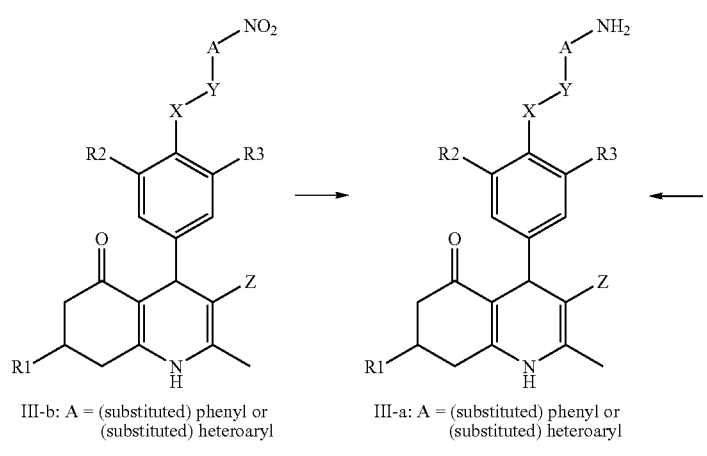

III-b: A = (substituted) phenyl or (substituted) heteroaryl

III-a: A = (substituted) phenyl or (substituted) heteroaryl

III-c: A = (substituted) phenyl or (substituted) heteroaryl
PG = protective group Amide derivatives I-n, wherein $R^1$, $R^2$, $R^3$, $R^{14}$, $R^{15}$, X, Y and Z are as previously defined and A is a (substituted) phenyl or (substituted) heteroaryl ring, may be prepared from carboxylic acids III-e, by the same methods (via acid chloride or by the use of coupling reagents) that were described for the preparation of compounds I-e from II-h.

Similarly, esters of general formula I-o, wherein $R^1$, $R^2$, $R^3$, $R^{14}$, X, Y and Z are as previously defined and A is a (substituted) phenyl or (substituted) heteroaryl ring may be obtained from derivatives III-e and alcohols of general formula $R^{14}$—OH using the same methods as described for the conversion of III-e into the corresponding amides I-n.

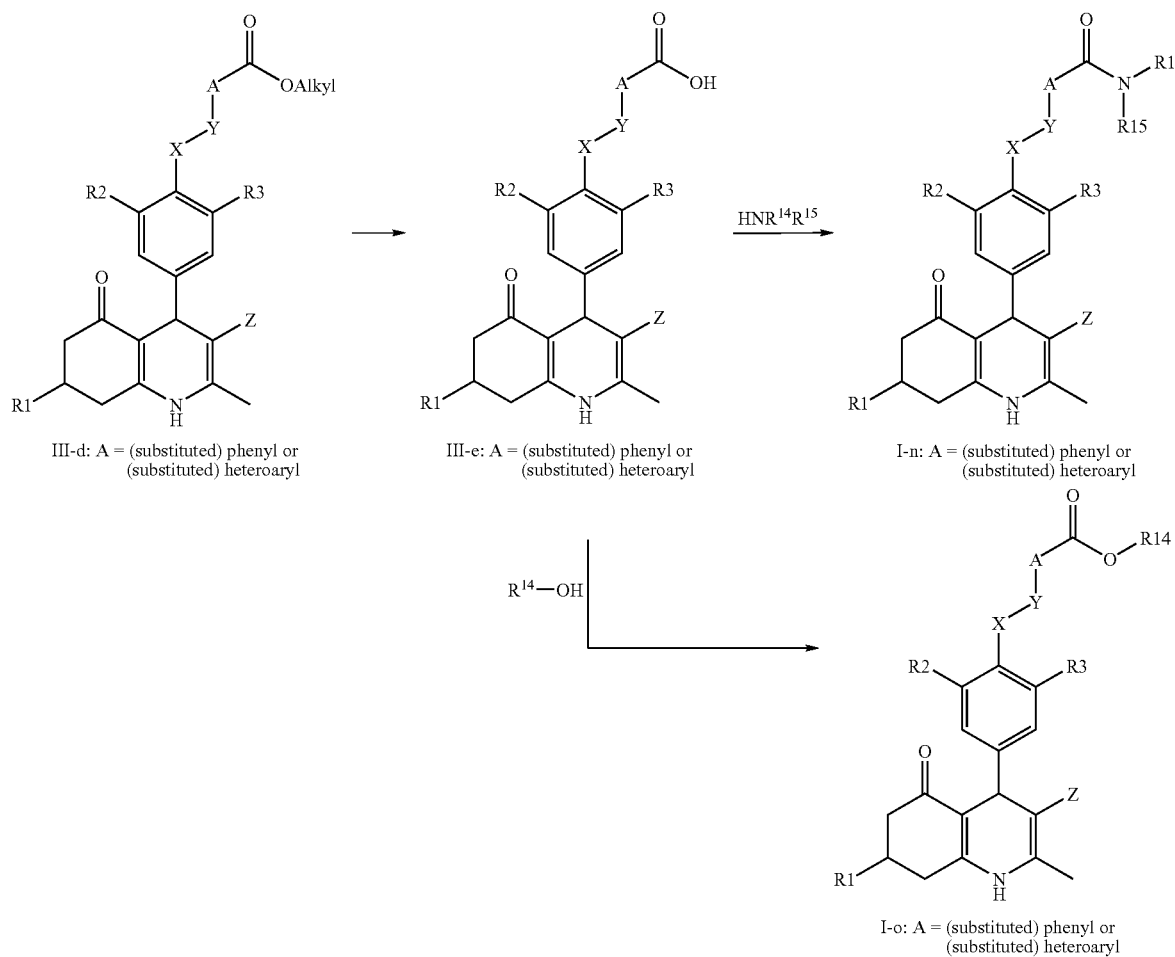

III-d: A = (substituted) phenyl or (substituted) heteroaryl

III-e: A = (substituted) phenyl or (substituted) heteroaryl

I-n: A = (substituted) phenyl or (substituted) heteroaryl

I-o: A = (substituted) phenyl or (substituted) heteroaryl

Compounds of general formula III-e may be prepared from the corresponding alkyl esters III-d by base or acid mediated ester cleavage, well known to those skilled in the art.

Derivatives of general formula I-p, wherein $R^1$, $R^2$, $R^3$, $R^{14}$, X, Y and Z are as previously defined and A is a (substituted) phenyl or a (substituted) heteroaryl ring, may be prepared by alkylation of the hydroxyl group in compounds of general formula III-g with an alkyl halide of general formula $R^{14}$-Hal, in which Hal may be Br, Cl or I. Typically, such a reaction is carried out in an aprotic solvent such as NAN-dimethylformamide, 1,4-dioxane or tetrahydrofuran in the presence of a base, such as sodium hydride, potassium carbonate, cesium carbonate or triethyl amine at ambient or elevated temperature. Alternatively, conversion of compounds of general formula III-g into aryl ethers of general formula I-p may be accomplished under Mitsunobu-type alkylation conditions. In such a transformation, alkylation of the hydroxyl group in compounds of formula III-g is effected with alcohols of general formula $R^{14}$—OH under the agency of (resin bound) triphenyl phosphine and diethyl azodicarboxylate or its derivatives in a suitable aprotic solvent such as tetrahydrofuran or dichloromethane.

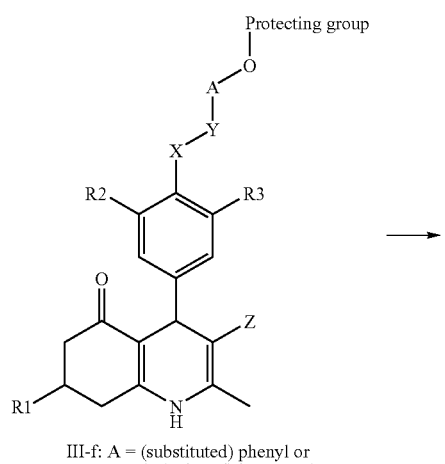

III-f: A = (substituted) phenyl or (substituted) heteroaryl

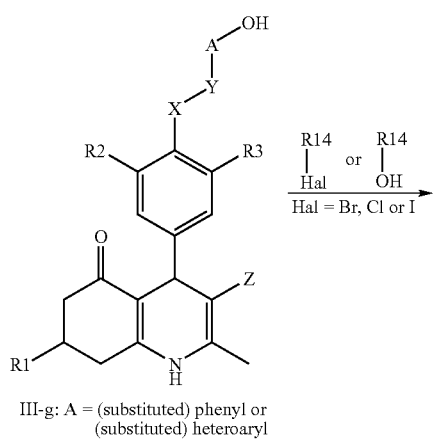

III-g: A = (substituted) phenyl or (substituted) heteroaryl

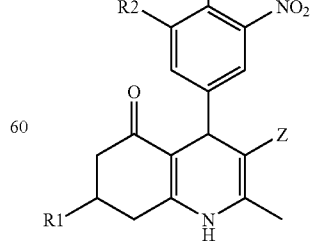

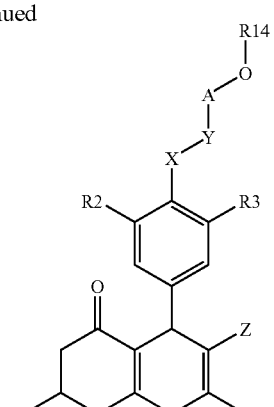

I-p: A = (substituted) phenyl or (substituted) heteroaryl

Derivatives of general formula III-g may be obtained by cleavage of the hydroxyl-protecting group in compounds of general formula III-f Suitable protective groups, well-known to those skilled in the art, are the tetrahydropyranyl (THP) or tert-butyl dimethylsilyl (TBS) protective groups. Cleavage of the THP and TBS groups is generally accomplished by treatment with acids, such as hydrochloric acid, trifluoromethanesulfonic acid or trifluoroacetic acid in a suitable solvent, such as tetrahydrofuran or methanol. Alternatively, the TBS group may be removed by treatment with tetra-n-butylammonium fluoride in tetrahydrofuran. Related protective group manipulations can be found in *Protective groups in Organic Synthesis*, T. W. Greene and P. G. M. Wuts, John Wiley & sons, Inc., New York, 1999.

Compounds of general formula I may also be obtained by manipulation of both functional groups FG1 and FG2 in compounds of general formula IV (method C), along the lines described for the conversions of compounds of general formula II and III. The two functional groups can be, but do not need to be, identical. It is clear to those skilled in the art that the order in which the functional groups FG1 and FG2 are modified may be crucial for a successful synthetic outcome. Clearly, in some cases the use of (orthogonal) protective groups may be necessary.

For example, dinitro compounds of general formula IV-a may be reduced to the diamino compounds IV-b using the methods described for the preparation of derivatives II-a from II-e. Standard N-acylation or N-sulfonylation affords compounds of general formula I-q, wherein $R^1$, $R^2$, $R^3$, X, Y and Z are as previously defined and A is a (substituted) phenyl or a (substituted) heteroaryl ring and $R^{13}$=$R^8$.

IV-a: A = (substituted) phenyl or (substituted) heteroaryl

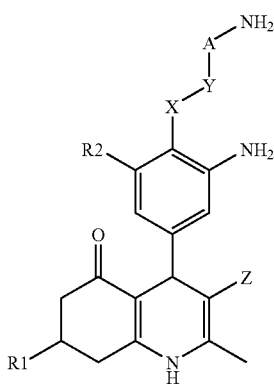

IV-b: A = (substituted) phenyl or (substituted) heteroaryl

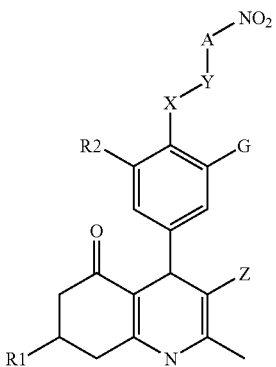

IV-d: A = (substituted) phenyl or (substituted) heteroaryl
G = NR$^7$R$^8$ or NR$^9$R$^{10}$

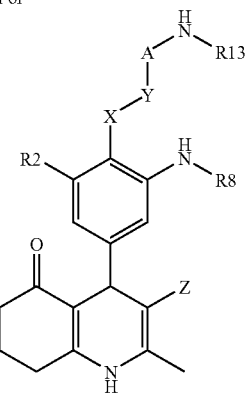

I-q: A = (substituted) phenyl or (substituted) heteroaryl
R$^8$ = R$^{13}$ = acyl or sulfonyl group

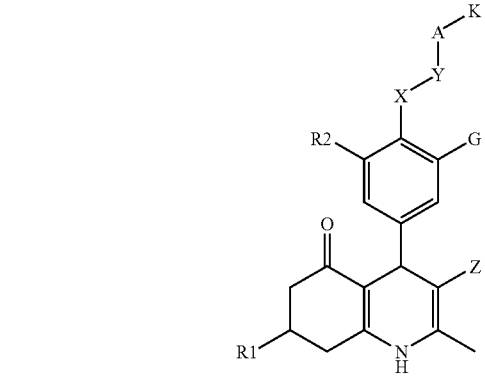

I-r: A = (substituted) phenyl or (substituted) heteroaryl
G = NR$^7$R$^8$ or NR$^9$R$^{10}$
K = NR$^{12}$R$^{13}$ or NR$^{14}$R$^{15}$ To allow independent variation of the substituents (e.g. R$^8$ and R$^{13}$), the functional groups in compounds of general formula IV need to be functionalized in an orthogonal manner. For example, compounds of general formula IV-c may be functionalized using the same methods described for the synthesis of derivatives I-a, I-b, I-c and I-d from compounds II-a to give compounds of general formula IV-d, wherein R$^1$, R$^2$, X, Y and Z are as previously defined, A is a (substituted) phenyl or a (substituted) heteroaryl ring and G is NR$^7$R$^8$ or NR$^9$R$^{10}$. These compounds may be converted to derivatives I-r, wherein R$^1$, R$^2$, X, Y and Z are as previously defined, A is a (substituted) phenyl or a (substituted) heteroaryl ring and G is NR$^7$R$^8$ or NR$^9$R$^{10}$ and K is NR$^{12}$R$^{13}$ or NR$^{14}$R$^{15}$.

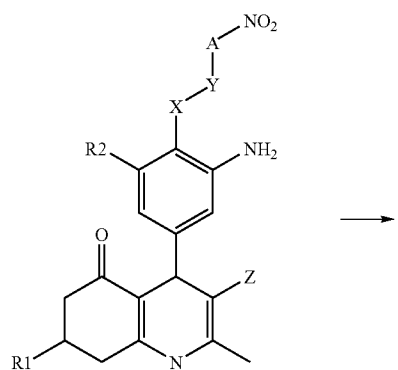

IV-c: A = (substituted) phenyl or (substituted) heteroaryl

Yet another possibility to arrive at the desired compounds of general formula I may be the functionalization of compounds of general formula V (method D). Compounds of general formula V-a wherein X=O may be used to prepare compounds I-s, wherein R$^1$, R$^2$, R$^3$, R$^4$, Y and Z are as previously defined and X=O, by O-alkylation, O-acylation or O-sulfonylation using standard conditions, well known to those skilled in the art. The substitution pattern of the (hetero) aryl ring in R$^4$ is as previously defined. In a typical experiment, compounds V-a are reacted in a solvent, such as dichloromethane, N,N-dimethylformamide, dimethyl sulfoxide, ethanol, tetrahydrofuran, 1,4-dioxane, toluene, 1-methyl-pyrrolidin-2-one or pyridine with an appropriately substituted (hetero)aromatic alkyl halide of formula IX, acyl chloride of formula X, or sulfonyl chloride of formula XII in the presence of a base such as triethylamine, N,N-diisopropylethylamine (DiPEA), pyridine, potassium carbonate, cesium carbonate or sodium hydride, optionally in the presence of a catalytic amount of potassium iodide or tetrabutylammonium iodide, to give O-alkylated, O-acylated or O-sulfonylated derivatives of formula I-s, respectively.

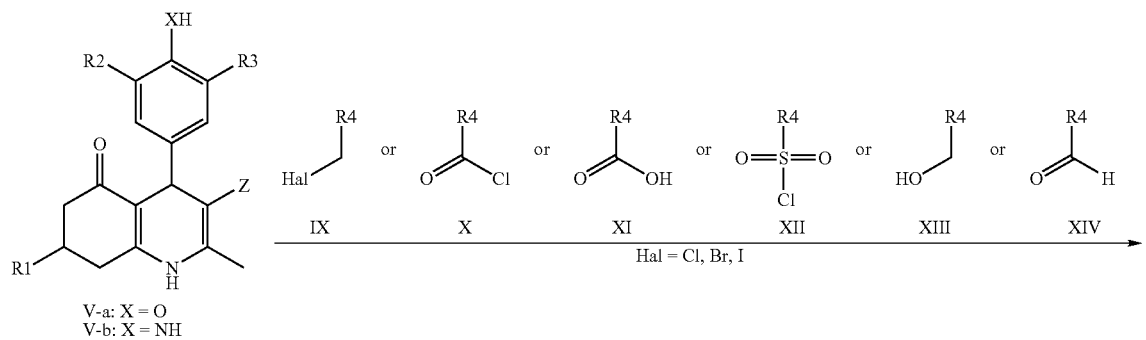

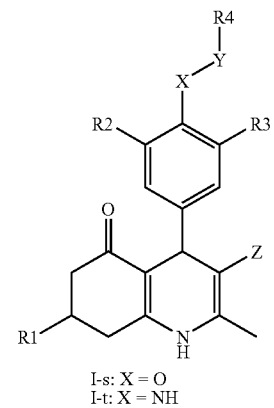

Alternatively, O-alkylated compounds of general formula I-s in which Y=CH$_2$ may be obtained by using art known Mitsunobu reactions with alcohols of formula XIII, triphenylphosphine (optionally resin bound) and a dialkyl azodicarboxylate (e.g. diethyl azodicarboxylate) in appropriate solvents such as 1,4-dioxane, tetrahydrofuran or dichloromethane at elevated or ambient temperature.

Additionally, O-acylated compounds of general formula I-s, wherein Y=C(O) may be obtained by reaction of a (hetero)aromatic carboxylic acid of formula XI in the presence of a coupling reagent such as diisopropyl carbodiimide (DIC), (3-dimethylaminopropyl)-ethyl-carbodiimide (EDCI), O-(benzotriazol-1-yl)-N,N,N',N'-tetramethyluronium tetrafluoroborate (TBTU) or O-(7-azabenzotriazol-1-yl)-N,N,N',N'-tetramethyluronium hexafluorophosphate (HATU) and a tertiary amine base (e.g. DiPEA) in a solvent such as N,N-dimethylformamide or dichloromethane at ambient or elevated temperature.

Likewise, compounds of general formula I-t may be prepared from compounds V-b by N-alkylation, N-acylation or N-sulfonylation using the same methods described for the synthesis of compounds I-s using the reagents of formula IX-XIII. Additionally, compounds of general formula I-t in which Y=CH$_2$ may be prepared by reductive amination of (hetero)aromatic aldehydes of formula XIV with compounds V-b and a suitable reducing agent such as sodium cyanoborohydride or sodium triacetoxyborohydride. Alternatively, compounds of general formula V-b may be converted to the corresponding benzimines upon reaction with (hetero)aromatic aldehydes XIV by methods known to those skilled in the art, followed by reduction with a reducing agent such as sodium borohydride to give compounds I-t in which Y=CH$_2$.

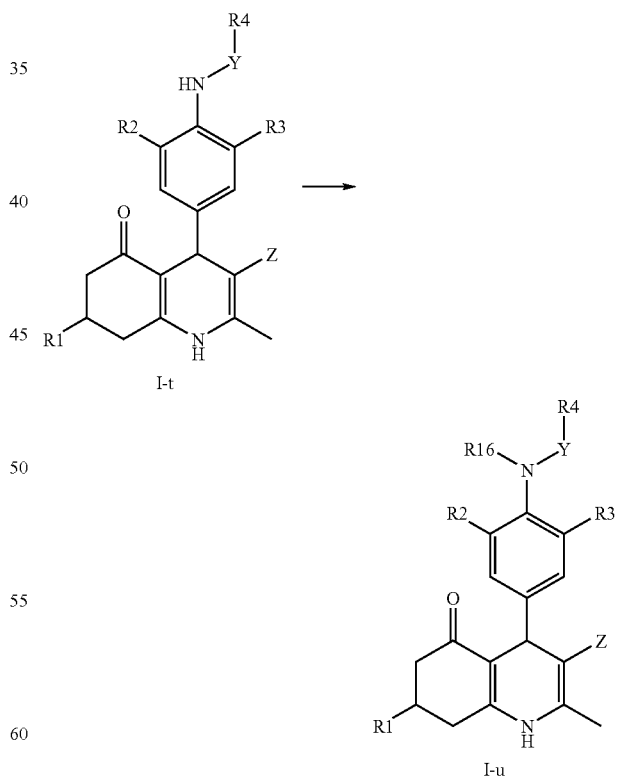

Compounds of general formula I-t wherein R$^1$, R$^2$, R$^3$, R$^4$, Y and Z are as previously defined and X is NH may be N-alkylated by the same methods as described for the preparation of derivatives I-b from I-a (if Y=C(O) or SO$_2$) or by the same methods as described for the preparation of derivatives compounds I-b from II-a (if Y=CH$_2$) to afford compounds of general formula I-u, wherein R$^{16}$ is a (1-4C)alkyl group.

Compounds of general formula I, wherein R$^1$, R$^2$, R$^3$, R$^4$, X, Y and Z are as previously defined, may also be prepared starting from cyclohexane-1,3-diones of general formula VI, enamines of general formula VII and benzaldehydes of general formula VIII-a-b, by the well-documented three component Hantzsch-type cyclo-condensation reaction (Method E).

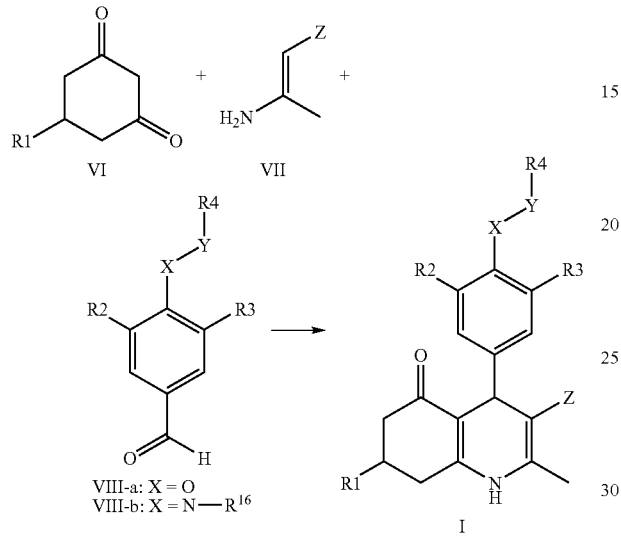

Related Hantzsch-type cyclo-condensation reactions can be found in: Bioorg. Med. Chem. Lett. 12 (2002) 1481-1484, J. Chem. Soc., Perkin Trans. 1 (2002) 1141-1156, Synlett (2002) 89-92, Drug Dev. Res. 51 (2000) 225-232, Drug Dev. Res. 51 (2000) 233-243, J. Med. Chem. 42 (1999) 1422-1427, ibid. 5266-5271, ibid. 41 (1998) 2643-2650, WO 9408966, Arzneim.-Forsch./Drug Res. 45 (1995) 1054-1056, J. Med. Chem. 34 (1991) 2248-2260, ibid. 17 (1974) 956-65, Indian J. Chem., Sect B (1994) 526-531, Chem. Rev. 72 (1972), 1-42. The above mentioned reaction is typically conducted at elevated temperature in suitable solvents such as acetic acid, (iso)propanol, ethanol, methanol or mixtures thereof.

Compounds of general formula I-w, wherein R$^2$ is H and R$^3$ is R$^9$,R$^{10}$-aminosulfonyl and R$^1$, R$^4$, X, Y and Z are as previously defined may be synthesized by catalytic hydrogenation of compounds of general formula I-v, using hydrogen and a transition metal catalyst such as palladium on charcoal in suitable solvents such as ethanol, methanol, ethyl acetate or mixtures thereof.

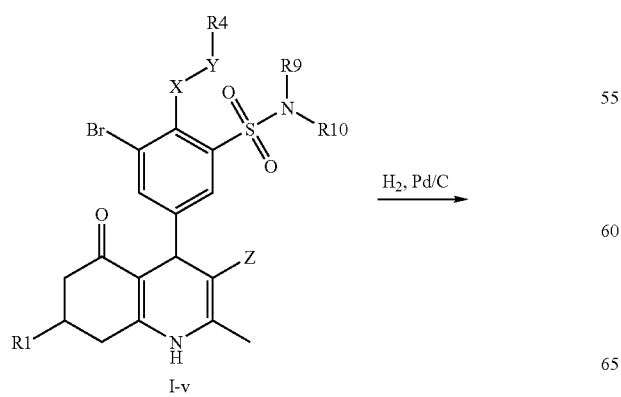

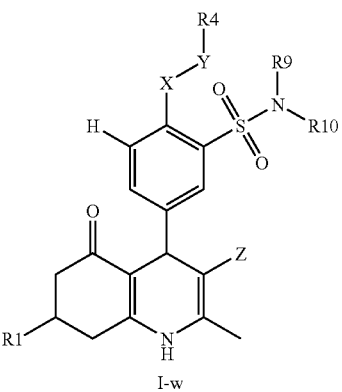

Compounds of general formula II are accessible from derivatives of general formula XV-a and XV-b using the same methods as described for the preparation of compounds of general formula I-s and I-t, respectively, using reagents of formula IX-XIV.

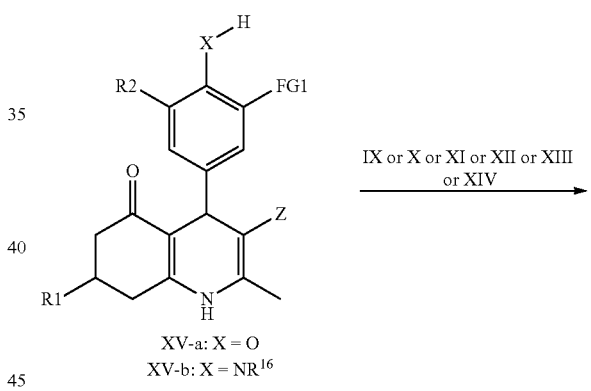

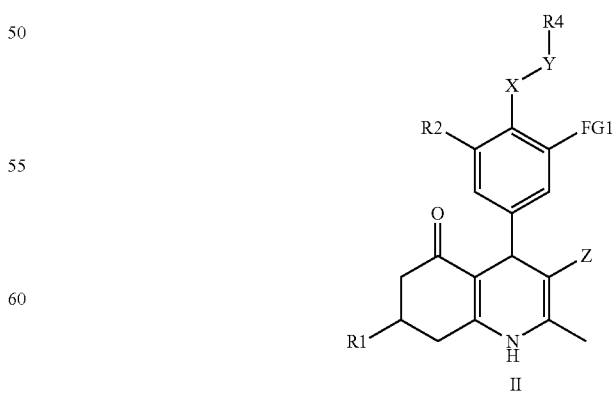

Similar to the N-alkylations of compounds of general formula I-t to give I-u, compounds of general formula I-k, wherein $R^1$, $R^2$, $R^4$, Y, Z are as previously defined and X=NH, may be N-alkylated to give compounds of general formula II-1, wherein $R^{16}$ is a (1-4C)alkyl group.
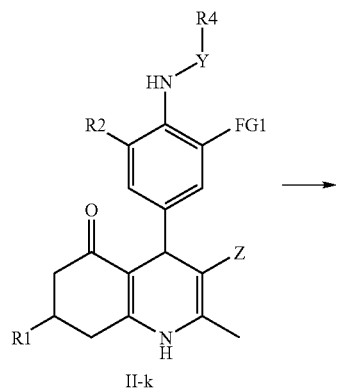
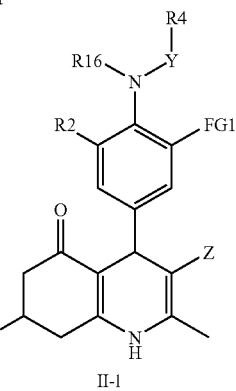
Compounds of general formula II and III may also be synthesized by the Hantzsch-type cyclo-condensation reactions by reacting compounds VI and VII with aldehydes of formula XVI or XVII, respectively.
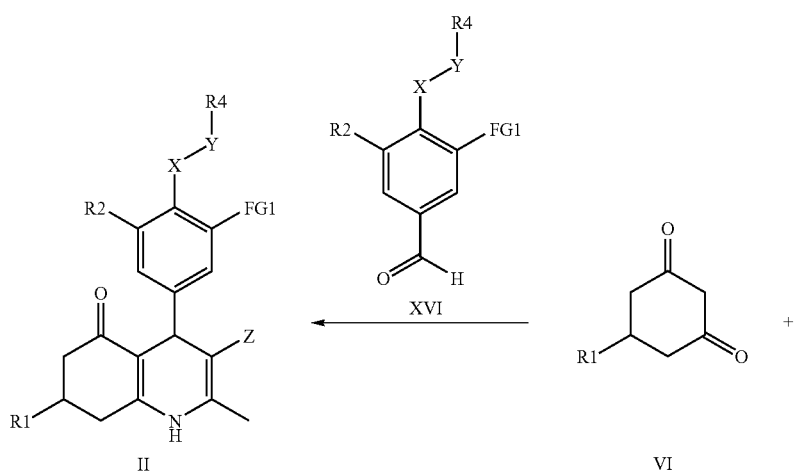
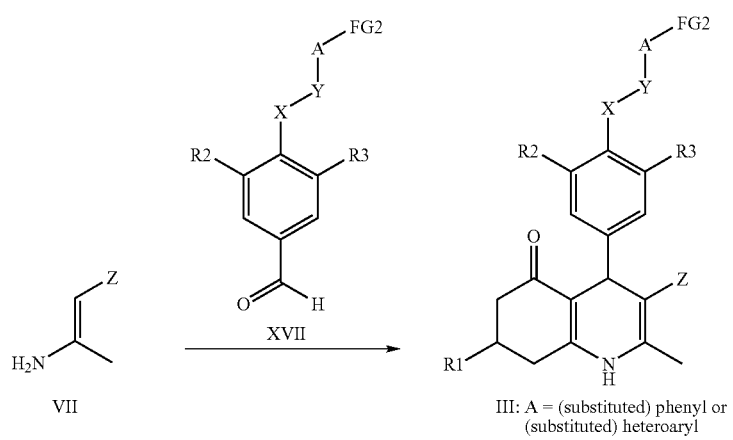

Compounds of general formula III are also accessible from derivatives of general formula V-a and V-b using the same methods as described for the preparation of compounds of general formula I-s and I-t, respectively, using reagents of formula XVIII-XXIII.

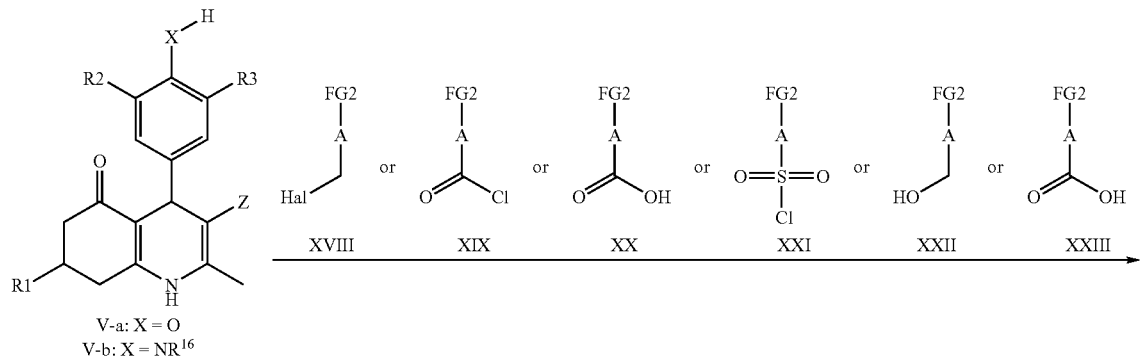

V-a: X = O
V-b: X = NR$^{16}$

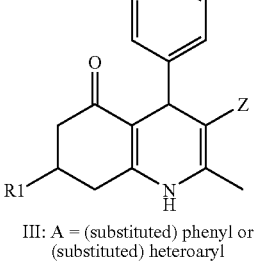

III: A = (substituted) phenyl or (substituted) heteroaryl

Similarly, compounds of general formula IV may be prepared from derivatives of general formula XV-a and XV-b using the same methods as described for the -continued

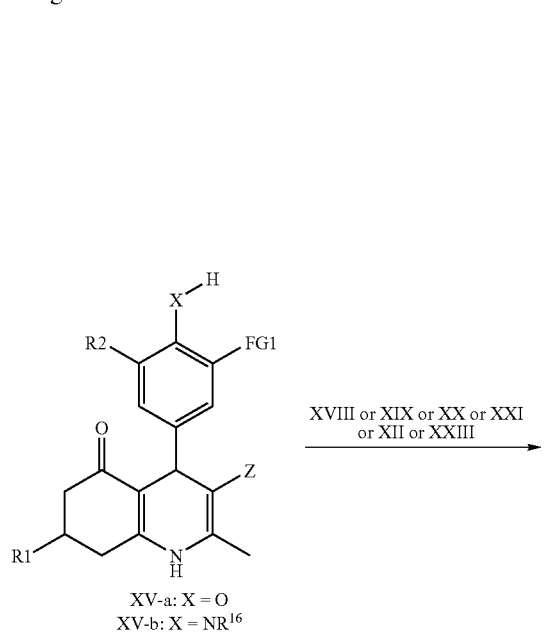

XV-a: X = O
XV-b: X = NR$^{16}$

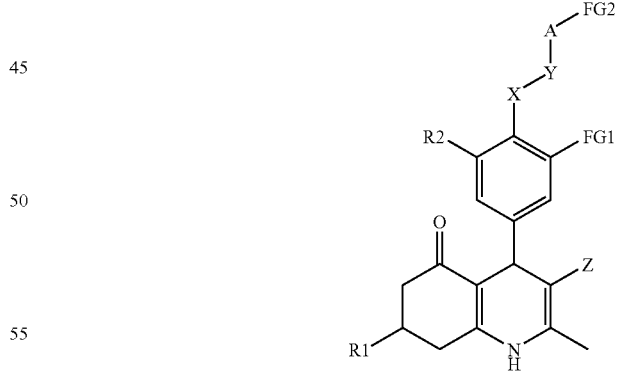

IV: A = (substituted) phenyl or (substituted) heteroaryl preparation of compounds of general formula I-s and I-t, respectively, using reagents of formula XVIII-XXIII.

Compounds of general formula IV and V-a-b may also be prepared by the previously mentioned Hantzsch-type cyclocondensation, by using substituted benzaldehydes of general formula XXIV or XXV, respectively.

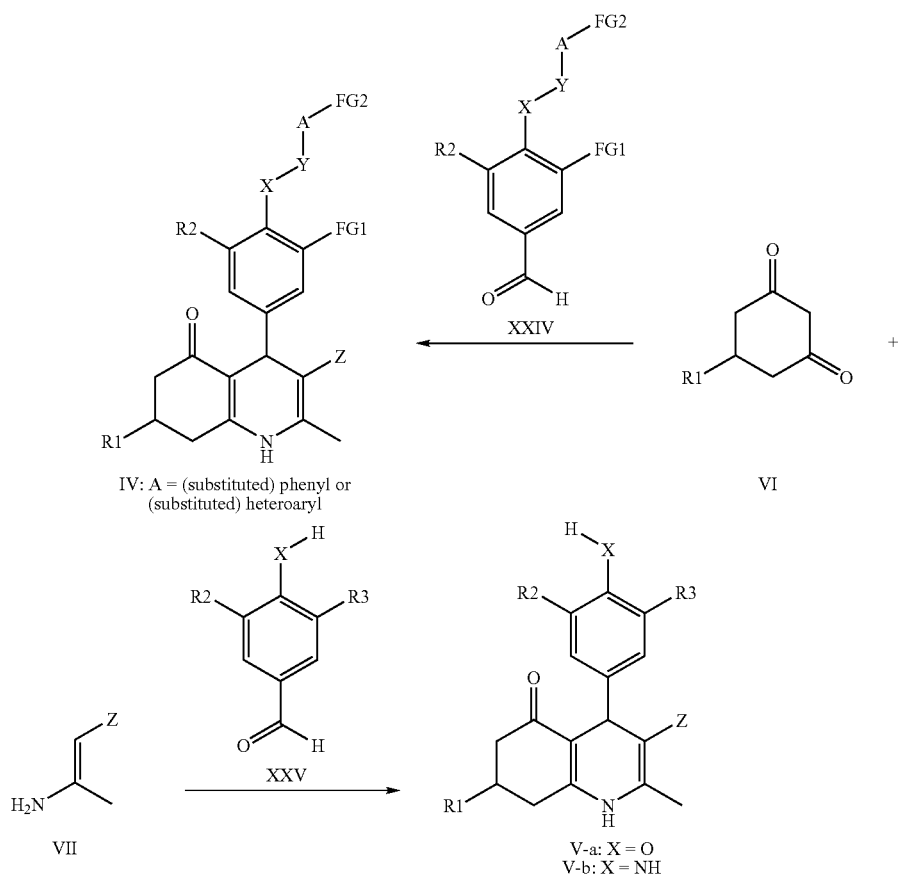

Compounds of general formula V-c-d in which $R^2$ is Br may also be obtained by ortho-bromination of phenols or anilines, which are well known to those skilled in the art. Thus, compounds of formula V-e-f—synthesized from compounds VI and VII and aldehydes XXVI by a Hantzsch-type cyclocondensation reaction—afford compounds of formula V-c-d upon treatment with bromine in a suitable solvent such as acetic acid, ethanol or dichloromethane or mixtures thereof, optionally in the presence of sodium acetate. Alternatively, N-bromosuccinimide in N,N-dimethylformamide or acetonitrile may be used to achieve this conversion. For example, see: J. Chem. Soc. Perkin Trans.2 6 (2000) 1113-1118, J. Org. Chem. 44 (1979), 4733-4735.

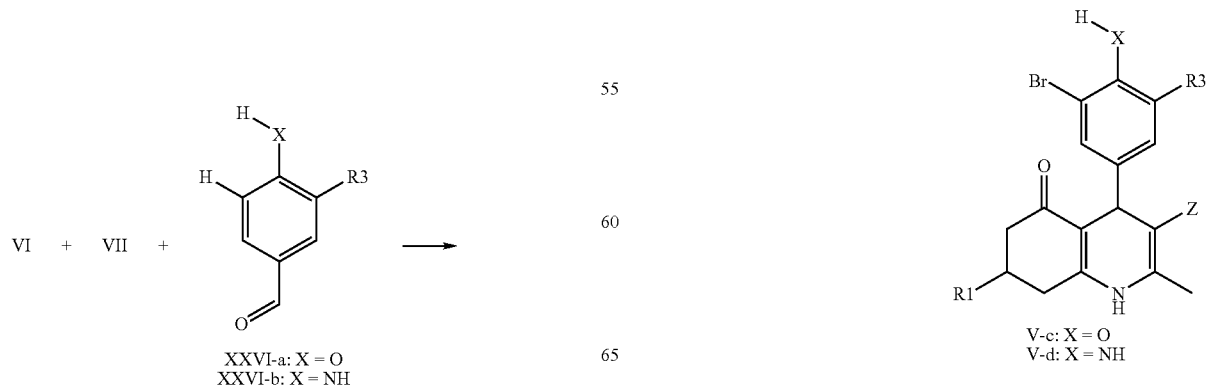

Additionally, compounds of general formula V-i, wherein $R^3$ is a sulfamoyl group and X=O, may be obtained by reacting amines of general formula $R^9R^{10}NH$ with compounds of general formula V-h, optionally in the presence of a tertiary amine base such as triethylamine or DiPEA. Compounds V-h are obtained by chlorosulfonylation of compounds of general formula V-g. For related examples in the literature concerning chlorosulfonylation of phenols, see: Tetrahedron 53 (1997) 4145-4158, Bioorg. Med. Chem. Lett. 13 (2003) 379-382.

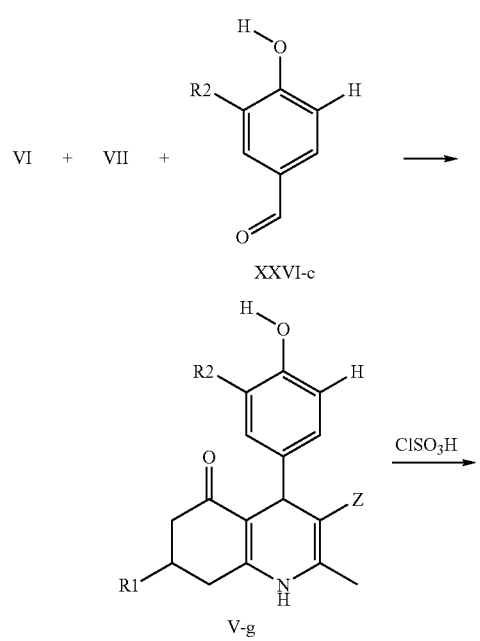

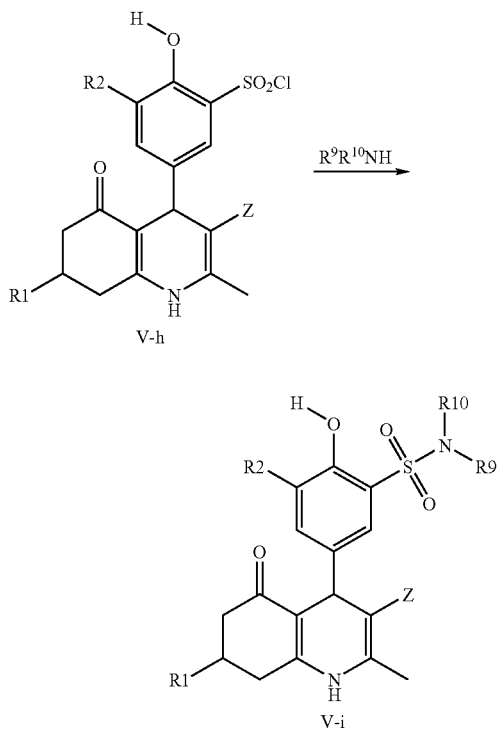

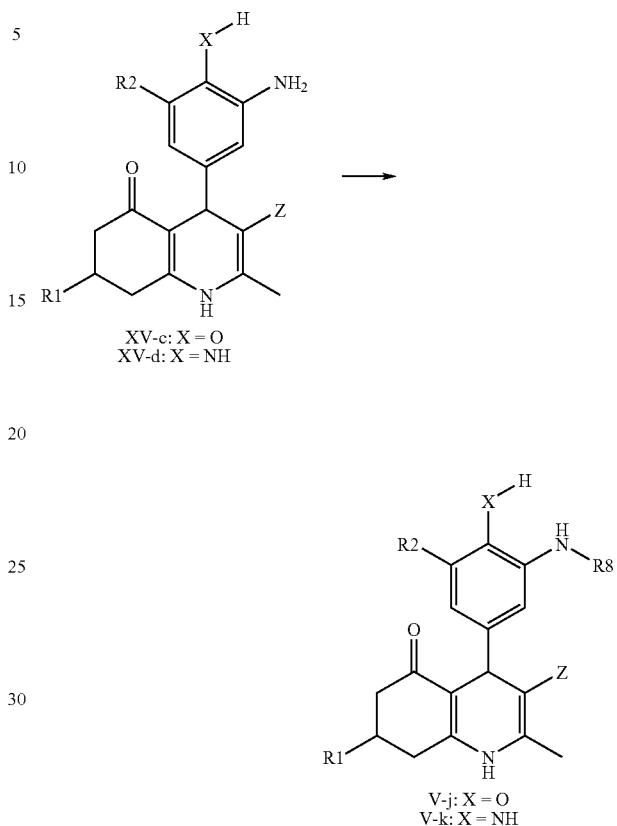

Compounds of general formula V may also be prepared from compounds of general formula XV by selective modification of FG1. For example, compounds of general formula XV-c-d, wherein $R^1$, $R^2$ and Z are as previously defined and FG1 is $NH_2$, may be selectively N-acylated or N-sulfonylated, using the same conditions described for the preparation of compounds I-a from II-a, to give compounds of general formula V-j-k, wherein $R^1$, $R^2$, $R^8$ and Z are as previously defined. For examples in literature reporting similar regioselectivity in the acylation or sulfonylation of 1,2-diaminobenzene derivatives, see: J. Chem. Soc., Perkin Trans. 1 (1988) 1939-1943, J. Med. Chem. 33 (1990) 2101-2108, J. Med. Chem. 43 (2000) 4084-4097, Bioorg. Med. Chem. 10 (2002) 3997-4004. For examples describing regioselective functionalisation of ortho-hydroxy aniline derivatives, see: J. Org. Chem. 53 (1988) 4762-4769, JP 2003026630, Pharm. Chem. J. 36 (2002), 410-412.

Compounds of general formula XV may also be prepared by the previously mentioned Hantzsch-type cyclo-condensation, by using substituted benzaldehydes of general formula XXVII. Additionally, compounds of general formula XV wherein $R^2$=Br may be prepared by Hantzsch reaction with aldehydes of general formula XXVIII, followed by ortho-bromination of the resulting phenols and anilines, in analogy with the preparation of compounds of formula V-c-d.

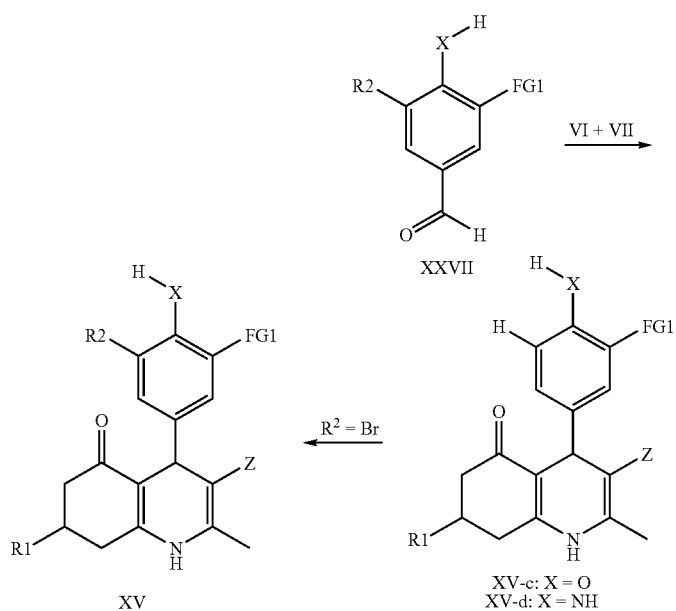
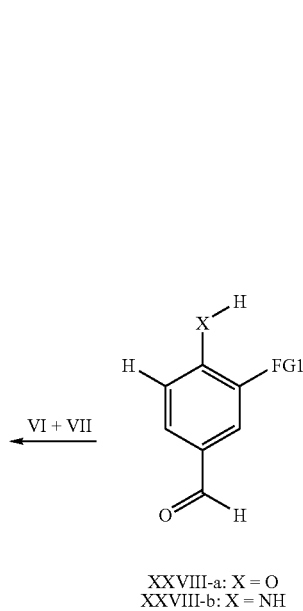

The substituted cyclohexane-1,3-diones of general formula VI are commercially available or may be prepared by literature procedures. Relevant examples are found in: J. Med. Chem. 43 (2000) 4678-4693, Tetrahedron 56 (2000) 4753-4758, J. Med. Chem. (1992) 3429-3447, ibid. 24 (1981) 1026-1034, Org. Synt. Coll. Vol. V (1973) 400, Chem. Ber. 88 (1955) 316-327, Justus Liebig Ann. Chem. 570 (1950) 15-31.

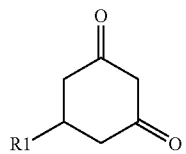

VI

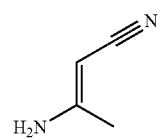

VII-a

-continued

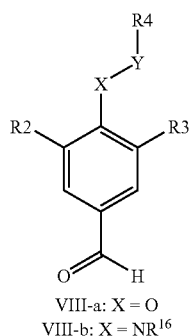

VII-b

The compound of formula VII-a is commercially available and compound VII-b has been documented in literature, see for example: Drug Dev. Res. 51 (2000) 225-232.

Compounds of general formula IX to XIV and XVIII to XXIII are either commercially available, documented in literature or readily synthesized by those skilled in the art.

Benzaldehydes of general formula VIII-a, wherein $R^2$, $R^3$, $R^4$ and Y are as previously defined and X=O, are readily prepared from benzaldehydes of general formula XXV-a using the same methods as described for the conversion of compounds of formula V-a to I-s. Likewise, compounds of general formula VIII-b, wherein $R^2$, $R^3$, $R^4$ and Y are as previously defined and X=N—$R^{16}$, are prepared from XXV-b using the same methods as described for the conversion of compounds of formula V-b to I-t. Similarly, benzaldehydes of general formula XVII-a-b are prepared from aldehydes XXV-a-b, upon reaction with compounds XVIII to XXIII.

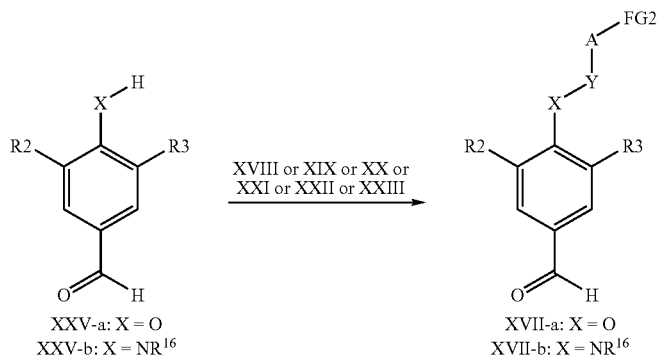

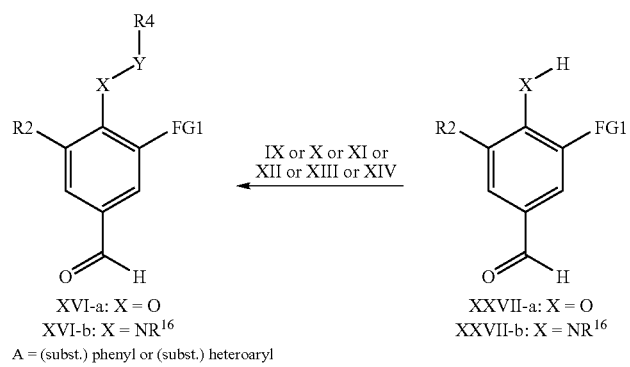

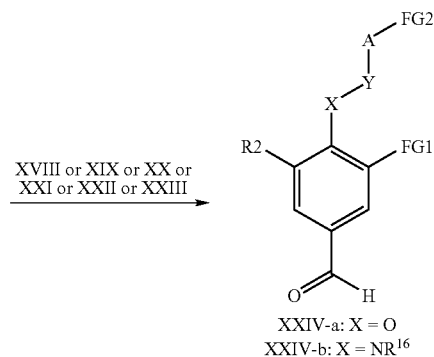

Following the same strategy, benzaldehydes of general formula XVI-a-b and XXIV-a-b are prepared from compounds of general formula XXVII-a-b.

Benzaldehydes of general formula XXV, XXVI, XXVII and XXVIII are commercially available, documented in the literature or may be prepared by those skilled in the art. For example, see: J. Chem. Soc., Perkin Trans. 2 (2000) 1119-1124, J. Chem. Soc., Chem. Commun. 4 (1993) 419-420, Synth. Commun. 20 (1990) 2659-2666, Chem. Pharm. Bull. 34 (1986) 121-129, Indian J. Chem. Sect. B 20 (1981) 1010-1013, Monatsh. Chem. 106 (1975) 1191-1201, DE 1070162, J. Org. Chem. 23 (1958) 120, Tetrahedron Lett. 25 (1984), 2901-2904, J. Org. Chem. 25 (1960), 2053-2055, J. Chem. Soc., Perkin Trans. 2 (1992), 2235-2242.

Additionally, benzaldehydes of general formula XXV-c and XXVII-c wherein $R^2$ is bromide and X is N—H may be obtained by bromination of compounds of general formula XXIX using the same procedures described for the conversion of compounds of general formula V-f to V-d. Compounds of general formula XXIX are easily prepared from compounds of general formula XXX using the same reduction methods that were described for the preparation of compounds of general formula II-a from II-e. Compounds of general formula XXX are commercially available, reported in literature or may be readily be prepared by those skilled in the art.

Furthermore, substituted benzaldehydes of general formulas VIII, XVI, XVII, XXIV, XXV, XXVI, XXVII, XXVIII, XXIX, XXX may be prepared from the corresponding benzoic acids XXXI or benzoic esters of general formula XXXII by reduction methods known in the art. Additionally, oxidation of alcohols XXXIII by methods well known in the art also affords benzaldehydes. Benzyl bromides XXXIV, which may be prepared from the corresponding toluene derivatives XXXV by benzylic bromination, may be converted into benzaldehydes by art known methods as well. Furthermore, the aldehydes may be obtained by deprotection of the corresponding (cyclic) acetals of general formula XXXVI.

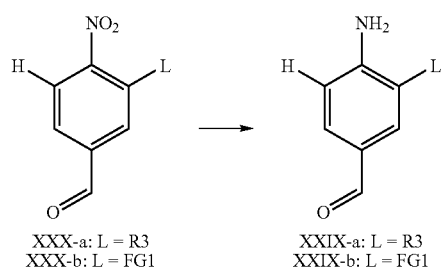

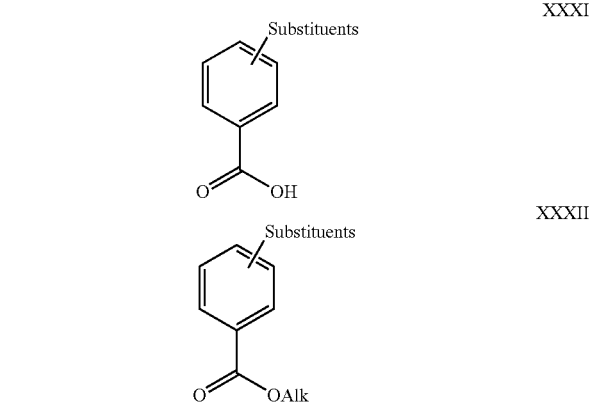

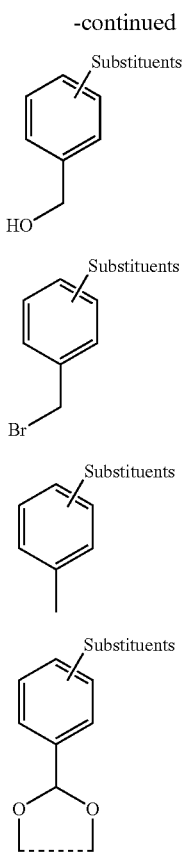

XXXIII

XXXIV

XXXV

XXXVI

The compounds of the present invention possess at least two chiral carbon atoms and may therefore be obtained as pure enantiomers, or as a mixture of enantiomers, or as a mixture of diastereomers. Methods for obtaining the pure enantiomers are well known in the art, e.g. crystallization of salts which are obtained from optically active acids and the racemic mixture, or chromatography using chiral columns. For separation of diastereomers, straight phase or reversed phase columns may be used.

The compounds of the invention may form hydrates or solvates. It is known to those of skill in the art that charged compounds form hydrated species when lyophilized with water, or form solvated species when concentrated in a solution with an appropriate organic solvent. The compounds of this invention include the hydrates or solvates of the compounds listed.

The 4-phenyl-5-oxo-1,4,5,6,7,8-hexahydroquinoline derivatives of the invention were found to agonists of the FSH receptor. Methods to determine receptor binding, as well as in vitro and in vivo assays to determine biological activity, of gonadotropins are well known. In general, expressed receptor is contacted with the compound to be tested and binding or stimulation or inhibition of a functional response is measured.

To measure a functional response, isolated DNA encoding the FSH receptor gene, preferably the human receptor, is expressed in suitable host cells. Such a cell might be the Chinese Hamster Ovary cell, but other cells are also suitable. Preferably the cells are of mammalian origin (Jia et al, Mol.Endocrin., 5:759-776, 1991).

Methods to construct recombinant FSH expressing cell lines are well known in the art (Sambrook et al., Molecular Cloning: a Laboratory Manual, Cold Spring Harbor Laboratory Press, Cold Spring Harbor, latest edition). Expression of receptor is attained by expression of the DNA encoding the desired protein. Techniques for site directed mutagenesis, ligation of additional sequences, PCR, and construction of suitable expression systems are all, by now, well known in the art. Portions, or all, of the DNA encoding the desired protein may be constructed synthetically using standard solid phase techniques, preferably to include restriction sites for ease of ligation. Suitable control elements for transcription and translation of the included coding sequence may be provided to the DNA coding sequences. As is well known, expression systems are now available which are compatible with a wide variety of hosts, including prokaryotic hosts such as bacteria and eukaryotic hosts such as yeast, plant cells, insect cells, mammalian cells, avian cells and the like.

Cells expressing the receptor are then contacted with the test compound to observe binding, or stimulation or inhibition of a functional response.

Alternatively, isolated cell membranes containing the expressed receptor may be used to measure binding of the test compound.

For measurement of binding, radioactive or fluorescent compounds may be used. As reference compound human recombinant FSH can be used.

In the alternative, also competition binding assays may be performed.

Another assay involves screening for FSH receptor agonist compounds by determining stimulation of receptor mediated cAMP accumulation. Thus, such a method involves expression of the receptor on the cell surface of a host cell and exposing the cell to the test compound. The amount of cAMP is then measured. The level of cAMP will be increased, by the stimulating effect of the test compound upon binding to the receptor.

In addition to direct measurement of e.g. cAMP levels in the exposed cell, cells lines can be used which in addition to transfection with receptor encoding DNA are also transfected with a second DNA encoding a reporter gene the expression of which responds to the level of cAMP. Such reporter genes might be cAMP inducible or might be constructed in such a way that they are connected to novel cAMP responsive elements. In general, reporter gene expression might be controlled by any response element reacting to changing levels of cAMP. Suitable reporter genes are e.g. LacZ, alkaline phosphatase, firefly luciferase and green fluorescence protein. The principles of such transactivation assays are well known in the art and are described e.g. in Stratowa, Ch., Himmler, A. and Czernilofsky, A. P., (1995) Curr. Opin. Biotechnol. 6:574.

The present invention also relates to a pharmaceutical composition comprising a 4-phenyl-5-oxo-1,4,5,6,7,8-hexahydroquinoline derivative or pharmaceutically acceptable salts thereof having the general formula I in admixture with pharmaceutically acceptable auxiliaries and optionally other therapeutic agents. The auxiliaries must be "acceptable" in the sense of being compatible with the other ingredients of the composition and not deleterious to the recipients thereof.

Pharmaceutical compositions include e.g. those suitable for oral, sublingual, subcutaneous, intravenous, intramuscular, nasal, local, or rectal administration, and the like, all in unit dosage forms for administration.

For oral administration, the active ingredient may be presented as discrete units, such as tablets, capsules, powders, granulates, solutions, suspensions, and the like.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., Remington: *The Science and Practice of Pharmacy* (20th Edition., Lippincott Williams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as hereinbefore described, in combination with packaging material suitable for said composition, said packaging material including instructions for the use of the composition for the use as hereinbefore described.

The exact dose and regimen of administration of the active ingredient, or a pharmaceutical composition thereof, may vary with the particular compound, the route of administration, and the age and condition of the individual subject to whom the medicament is to be administered.

In general parenteral administration requires lower dosages than other methods of administration which are more dependent upon absorption. However, a suitable dosage for humans may be 0.05-25 mg per kg body weight. The desired dose may be presented as one dose or as multiple subdoses administered at appropriate intervals throughout the day, or, in case of female recipients, as doses to be administered at appropriate daily intervals throughout the menstrual cycle. The dosage as well as the regimen of administration may differ between a female and a male recipient.

Thus, the compounds according to the invention can be used in therapy.

A further aspect of the invention resides in the use of a 4-phenyl-5-oxo-1,4,5,6,7,8-hexahydroquinoline derivative having the general formula I for the manufacture of a medicament to be used for the treatment of disorders responsive to FSH receptor mediated pathways, preferably for the treatment of fertility disorders. Thus, patients in need thereof can be administered with suitable amounts of the compounds according to the invention.

In yet another aspect the invention resides in the use of a 4-phenyl-5-oxo-1,4,5,6,7,8-hexahydroquinoline derivative having the general formula I for the manufacture of a medicament to be used for the treatment of fertility disorders.

The invention is illustrated by the following examples.

EXAMPLES

General Comments

The following abbreviations are used in the examples: DMA=N,N-dimethylaniline, DIPEA=N,N-diisopropylethylamine, TFA=trifluoroacetic acid, HATU=O-(7-azabenzotriazole-1-yl)-N,N,N',N'-tetramethyluronium hexafluorophosphate, Fmoc=9-fluorenylmethoxycarbonyl, Fmoc-Cl=9-fluorenylmethoxycarbonylchloride, DMF=N,N-dimethylformamide, THF=tetrahydrofuran.

Unless stated otherwise, all final products of the examples below were lyophilized from water/1,4-dioxane mixtures, water/tert-butanol or water/acetonitrile mixtures. If the compound was prepared as a HCl— or TFA salt, the respective acids were added in appropriate amounts to the solvent mixture before lyophilization.

The names of the final products described in the examples were generated using the Beilstein Autonom program (version: 2.02.304).

The following analytical HPLC methods were used for determination of retention times:

Method 1: Column: 5 μm Luna C-18(2) 150×4.6 mm; flow: 1 ml/min; detection: 210 nm; column temperature: 40° C.; solvent A: $CH_3CN/H_2O=1/9$ (v/v); solvent B: $CH_3CN$; solvent C: 0.1 M aqueous trifluoroacetic acid; gradient: solvent A/B/C=65/30/5 to 10/85/5 (v/v/v) in 30.00 min, then constant for an additional 10.00 min at A/B/C=10/85/5 (v/v/v).

Method 2: Identical to method 1, except for the gradient used: Gradient: solvent A/B/C=75/20/5 to 15/80/5 (v/v/v) in 30.00 min, then constant for an additional 10.00 min at A/B/C=15/80/5 (v/v/v).

Method 3: Identical to method 1, except for the gradient used: Gradient: solvent A/B/C=95/0/5 to 15/80/5 (v/v/v) in 30.00 min, then constant for an additional 10.00 min at A/B/C=15/80/5 (v/v/v).

Method 4: Identical to method 1, except for the gradient used: Gradient: solvent A/B/C=60/40/0 to 0/100/0 (v/v/v) in 20.00 min, then constant for an additional 10.00 min at A/B/C=0/100/0 (v/v/v).

The diastereomeric ratio was determined if baseline separation of the individual diastereomers was observed using the appropriate analytical HPLC method. Alternatively, the diastereomeric ratio was determined by $^1H$ NMR analysis when distinct signals corresponding to the diastereomers were identified.

The following methods were used for preparative HPLC-purifications:

Method A: Column=Luna C-18. Gradient: 0.1% trifluoroacetic acid in $H_2O/CH_3CN$ (9/1, v/v)/$CH_3CN$=80/20 to 0/100 (v/v) in 30-45 min, depending on the ease of separation. Detection: 210 nm.

Method B: Column=Luna C-18. Gradient: $H_2O/CH_3CN$ (9/1, v/v)/$CH_3CN$=80/20 to 0/100 (v/v) in 30-45 min, depending on the ease of separation. Detection: 210 nm.

EXAMPLE 1

4-[3-Bromo-4,5-bis-(3-methoxy-benzyloxy)-phenyl]-2-methyl-5-oxo-7-propyl-1,4,5,6,7,8-hexahydro-quinoline-3-carbonitrile (a). 3-Bromo-4,5-bis-(3-methoxy-benzyloxy)-benzaldehyde A mixture of 5-bromo-3,4-dihydroxybenzaldehyde (100 mg), 3-methoxybenzyl bromide (71 μl), potassium carbonate (140 mg) and tetrabutylammonium iodide (10 mg) in 5 ml of DMF was stirred at 60° C. for 3 h. The reaction mixture was diluted with water and extracted with ethyl acetate. The organic layer was dried ($MgSO_4$), filtered and concentrated in vacuo.

Yield: 143 mg.

(b). 4-[3-Bromo-4,5-bis-(3-methoxy-benzyloxy)-phenyl]-2-methyl-5-oxo-7-propyl-1,4,5,6,7,8-hexahydro-quinoline-3-carbonitrile A mixture of 3-bromo-4,5-bis-(3-methoxy-benzyloxy)-benzaldehyde (143 mg), 3-aminocrotonitrile (28 mg), 5-propylcyclohexane-1,3-dione (52 mg) in ethanol (10 ml) was stirred at 80° C. for 17 h. The mixture was concentrated in vacuo. The residue was purified by chromatography on silicagel in heptane/ethyl acetate 1/1→2/8 (v/v) as eluent.

Yield: 122 mg. MS-ESI: $[M+H]^+$=657.4/659.4; anal. HPLC $R_t$=17.18 min (diast.1) $R_t$=17.43 min (diast.2) (method 4)

Diast. ratio: 4:1

EXAMPLE 2

4-[3-Bromo-4-(3-methoxy-benzyloxy)-5-nitro-phenyl]-2-methyl-5-oxo-7-propyl-1,4,5,6,7,8-hexahydro-quinoline-3-carbonitrile

(a). 3-Bromo-4-hydroxy-5-nitro-benzaldehyde

3-Bromo-4-hydroxybenzaldehyde (250 mg) was dissolved in 5 ml of acetic acid. Nitric acid (52 µl) was added and the mixture was stirred for 3 h during which a solid formed. The solid was filtered off, washed with water and dried in vacuo.

Yield: 249 mg. MS-ESI: $[M+H]^+$=245.8/247.8

(b). 3-Bromo-4-(3-methoxy-benzyloxy)-5-nitro-benzaldehyde

To a solution of 3-bromo-4-hydroxy-5-nitro-benzaldehyde (87.4 mg) in dry dichloromethane (7.5 ml) was added 3-methoxybenzyl alcohol (35 µl), triphenylphosphine (103 mg) and diethyl azodicarboxylate (45 µl). The mixture was stirred under a nitrogen atmosphere for 17 h and then concentrated in vacuo. The residue was purified by chromatography on silicagel in heptane/ethyl acetate 9/1→1/1 (v/v) as eluent.

Yield: 50 mg.

(c). 4-[3-Bromo-4-(3-methoxy-benzyloxy)-5-nitro-phenyl]-2-methyl-5-oxo-7-propyl-1,4,5,6,7,8-hexahydro-quinoline-3-carbonitrile A mixture of 3-bromo-4-(3-methoxy-benzyloxy)-5-nitro-benzaldehyde (50 mg), 3-aminocrotonitrile (13 mg) and 5-propylcyclohexane-1,3-dione (25 mg) in 10 ml of ethanol was stirred at 80° C. for 17 h. The mixture was concentrated in vacuo. The residue was purified by chromatography on silicagel in heptane/ethyl acetate 8/2→1/1 (v/v) as eluent.

Yield: 50 mg. MS-ESI: $[M+H]^+$=566.2/568.2; anal. HPLC $R_t$=22.66 min (method 1)

Diast. ratio: 4:1

EXAMPLE 3

4-[3-Amino-5-bromo-4-(3-methoxy-benzyloxy)-phenyl]-2-methyl-5-oxo-7-propyl-1,4,5,6,7,8-hexahydro-quinoline-3-carbonitrile The compound described in example 2c (81 mg) was dissolved in THF (10 ml) and cooled to 0° C. Acetic acid (123 µl) was added, followed by addition of zinc dust (187 mg). After stirring at room temperature for 1 h, the mixture was diluted with dichloromethane and washed with sat. aq. $NaHCO_3$ and brine. The organic layer was dried ($MgSO_4$), filtered and concentrated in vacuo. The residue was purified by preparative HPLC (Method A).

Yield: 15.3 mg (as TFA salt). MS-ESI: $[M+H]^+$=536.4/538.4; anal. HPLC: $R_t$=18.77 min. (method 1)

Diast. ratio: 5:1

EXAMPLE 4

4-[3-Ethoxy-4-(3-methoxy-benzyloxy)-5-nitro-phenyl]-2-methyl-5-oxo-7-propyl-1,4,5,6,7,8-hexahydro-quinoline-3-carbonitrile

(a). 3-Ethoxy-4-(3-methoxy-benzyloxy)-5-nitro-benzaldehyde

A mixture of 5-nitro-3-ethoxy-4-hydroxybenzaldehyde (100 mg), 3-methoxybenzyl bromide (73 µl), potassium carbonate (144 mg) and tetrabutylammonium iodide (10 mg) in DMF (5 ml) was stirred at 60° C. for 90 min. The mixture was poured into water and extracted with ethyl acetate. The organic layer was dried ($MgSO_4$), filtered and concentrated in vacuo. The residue was purified by chromatography on silicagel in heptane/ethyl acetate 2/1 (v/v) as eluent.

Yield: 43 mg.

(b). 4-[3-Ethoxy-4-(3-methoxy-benzyloxy)-5-nitro-phenyl]-2-methyl-5-oxo-7-propyl-1,4,5,6,7,8-hexahydro-quinoline-3-carbonitrile A mixture of 3-ethoxy-4-(3-methoxy-benzyloxy)-5-nitro-benzaldehyde (40 mg), 3-aminocrotonitrile (10 mg) and 5-propylcylcohexane-1,3-dione (19 mg) in ethanol (2 ml) was stirred at 80° C. for 17 h. The mixture was concentrated in vacuo. The residue was purified by chromatography on silicagel in heptane/ethyl acetate 1/1 (v/v) as eluent.

Yield: 50 mg. MS-ESI: $[M+H]^+$=532.4; anal. HPLC: $R_t$=21.17 min. (diast.1) $R_t$=21.55 min. (diast 2.) (hetero 1)

Diast. ratio: 4.5:1

EXAMPLE 5

4-[3-Amino-5-ethoxy-4-(3-methoxy-benzyloxy)-phenyl]-2-methyl-5-oxo-7-propyl-1,4,5,6,7,8-hexahydro-quinoline-3-carbonitrile To a solution of the compound described in example 4b (100 mg) and acetic acid (162 µl) in THF (5 ml), cooled to 0° C., was added zinc dust (246 mg) under vigorous stirring.

After stirring for 30 min., the mixture was filtered, diluted with dichloromethane and washed with water. The organic layer was dried ($MgSO_4$), filtered and concentrated in vacuo.

Yield: 85 mg (as TFA salt). MS-ESI: $[M+H]^+$=502.4; anal. HPLC: $R_t$=15.28 min. (diast.1) $R_t$=16.38 min. (diast.2) (method 2)

Diast. ratio 4:1

EXAMPLE 6

N-[3-Bromo-5-(3-cyano-2-methyl-5-oxo-7-propyl-1,4,5,6,7,8-hexahydro-quinolin-4-yl)-2-(3-methoxy-benzyloxy)-phenyl]-butyramide A mixture of the compound described in example 3 (100 mg), butyryl chloride (21 µl) and N,N-diisopropylethylamine (162 µl) in dichloromethane (5 ml) was stirred for 17 h. The mixture was diluted with dichloromethane and washed with sat. aq. NaHCO$_3$. The organic layer was dried (MgSO$_4$), filtered and concentrated in vacuo. The residue was purified by preparative HPLC (Method B).

Yield: 52 mg. MS-ESI: [M+H]$^+$=606.2/608.2; anal. HPLC: R$_t$=21.60 min. (diast.1) R$_t$=21.99 min. (diast.2) (method 1)

Diast. ratio: 4:1

EXAMPLE 7

[3-Bromo-5-(3-cyano-2-methyl-5-oxo-7-propyl-1,4, 5,6,7,8-hexahydro-quinolin-4-yl)-2-(3-methoxy-benzyloxy)-phenyl]-carbamic acid methyl ester A mixture of the compound described in example 3 (100 mg), methyl chloroformate (17 µl) and N,N-diisopropylethylamine (162 µl) in dry dichloromethane (5 ml) was stirred for 17 h. The mixture was diluted with dichloromethane and washed with sat. aq. NaHCO$_3$. The organic layer was dried (MgSO$_4$), filtered and concentrated in vacuo. The residue was purified by preparative HPLC (Method B).

Yield: 35 mg. MS-ESI: [M+H]$^+$=594.2/596.2; anal. HPLC: R$_t$=20.33 min. (diast.1) R$_t$=20.73 min. (diast.1) (method 1)

Diast. ratio: 5:1

EXAMPLE 8

N-[3-Bromo-5-(3-cyano-2-methyl-5-oxo-7-propyl-1, 4,5,6,7,8-hexahydro-quinolin-4-yl)-2-(3-methoxy-benzyloxy)-phenyl]-2-methoxy-acetamide A mixture of the compound described in example 3 (100 mg), methoxy-acetyl chloride (24.3 mg) and N,N-diisopropylethylamine (162 µl) in dichloromethane (5 ml) was stirred for 17 h. The mixture was diluted with dichloromethane and washed with sat. aq. NaHCO$_3$. The organic layer was dried (MgSO$_4$), filtered and concentrated in vacuo. The residue was purified by preparative HPLC (Method B).

Yield: 37 mg. MS-ESI: [M+H]$^+$=608.2/610.2; anal. HPLC: R$_t$=19.99 min. (diast.1) R$_t$=20.44 min. (diast.2) (method 1)

Diast. ratio: 5:1

EXAMPLE 9

Furan-2-carboxylic acid [3-bromo-5-(3-cyano-2-methyl-5-oxo-7-propyl-1,4,5,6,7,8-hexahydro-quinolin-4-yl)-2-(3-methoxy-benzyloxy)-phenyl]-amide A mixture of the compound described in example 3 (100 mg), 2-furoyl chloride (28.9 mg) and N,N-diisopropylethylamine (162 µl) in dichloromethane (5 ml) was stirred for 17 h. The mixture was diluted with dichloromethane and washed with sat. aq. NaHCO$_3$. The organic layer was dried (MgSO$_4$), filtered and concentrated in vacuo. The residue was purified by preparative HPLC (Method B).

Yield: 92 mg. MS-ESI: [M+H]$^+$=630.2/632.2; anal. HPLC: R$_t$=21.27 min. (diast.1) R$_t$=21.75 min. (diast.2) (method 1)

Diast. ratio: 5:1

EXAMPLE 10

N-[3-Bromo-5-(3-cyano-2-methyl-5-oxo-7-propyl-1, 4,5,6,7,8-hexahydro-quinolin-4-yl)-2-(3-methoxy-benzyloxy)-phenyl]-methanesulfonamide A mixture of the compound described in example 3 (100 mg), methanesulfonyl chloride (22 µl) and pyridine (46 µl) in dichloromethane (5 ml) was stirred for 17 h. The mixture was diluted with dichloromethane and washed with sat. aq. NaHCO$_3$. The organic layer was dried (MgSO$_4$), filtered and concentrated in vacuo. The residue was purified by preparative HPLC (Method B).

Yield: 55 mg. MS-ESI: [M+H]$^+$=614.2/616.2; anal. HPLC: R$_t$=18.24 min. (method 1)

Diast. ratio: 6:1

EXAMPLE 11

2-Methoxy-benzoic acid 2-bromo-4-(3-cyano-2-methyl-5-oxo-7-propyl-1,4,5,6,7,8-hexahydro-quinolin-4-yl)-6-nitro-phenyl ester (a). 3-Bromo-4-hydroxy-5-nitro-benzaldehyde To a cooled solution of 3-bromo-4-hydroxybenzaldehyde (5 g) in acetic acid (50 ml) was added nitric acid (1.17 ml). The mixture was allowed to reach room temperature. After stirring for 17 h, the resulting precipitate was filtered off. The solid was washed with water and dried in vacuo.

Yield: 3.7 g.

(b). 4-(3-Bromo-4-hydroxy-5-nitro-phenyl)-2-methyl-5-oxo-7-propyl-1,4,5,6,7,8-hexahydro-quinoline-3-carbonitrile A mixture of 3-bromo-4-hydroxy-5-nitro-benzaldehyde (2 g), 3-aminocrotonitrile (667 mg) and 5-propylcyclohexane-1,3-dione (1.25 g) in ethanol (75 ml) was heated to reflux for 17 h. The mixture was concentrated in vacuo. The residue was purified by chromatography on silicagel in heptane/ethyl acetate 1/0→0/1 (v/v) as eluent.

Yield: 1.8 g. MS-ESI: [M+H]$^+$=446.2/448.2

(c). 2-Methoxy-benzoic acid 2-bromo-4-(3-cyano-2-methyl-5-oxo-7-propyl-1,4,5,6,7,8-hexahydro-quinolin-4-yl)-6-nitro-phenyl ester A mixture of 4-(3-bromo-4-hydroxy-5-nitro-phenyl)-2-methyl-5-oxo-7-propyl-1,4,5,6,7,8-hexahydro-quinoline-3-carbonitrile (200 mg), N,N-diisopropylethylamine (390 µl) and 2-methoxy-benzoyl chloride (53 µl) in dichloromethane (4 ml) was stirred for 4 h. The mixture was diluted with dichloromethane and washed with water. The organic layer was dried (MgSO$_4$), filtered and concentrated in vacuo.

The residue was purified by chromatography on silicagel in heptane/ethyl acetate 1/0→0/1 (v/v) as eluent.

Yield: 90 mg. MS-ESI: [M+H]$^+$=580.2/582.2; anal. HPLC: R$_t$=24.32 min. (method 2)

EXAMPLE 12

4-[3-Bromo-5-isopropylamino-4-(3-methoxy-benzyloxy)-phenyl]-2-methyl-5-oxo-7-propyl-1,4,5,6,7,8-hexahydro-quinoline-3-carbonitrile To a mixture of the compound described in example 3 (100 mg), acetic acid (114 µl) and acetone (20 µl) in 2 ml of dichloromethane and 2 ml of methanol was added sodium cyanoborohydride (25 mg) in 1 ml of methanol. After stirring for 17 h, the mixture was diluted with dichloromethane and washed with water. The residue was purified by chromatography on silicagel in heptane/ethyl acetate 9/1→0/1 (v/v) as eluent.

Yield: 94 mg. MS-ESI: [M+H]$^+$=578.4/580.4; anal. HPLC: R$_t$=23.34 min. (diast.1) R$_t$=23.73 min. (diast.2) (method 1)

Diast. ratio: 5:1

EXAMPLE 13

4-[3-Bromo-5-dimethylamino-4-(3-methoxy-benzyloxy)-phenyl]-2-methyl-5-oxo-7-propyl-1,4,5,6,7,8-hexahydro-quinoline-3-carbonitrile To a mixture of the compound described in example 3 (100 mg) and acetic acid (114 µl) in 2 ml of dichloromethane and 2 ml of methanol was added a solution of 37% formaldehyde in methanol (64 µl) and sodium cyanoborohydride (16 mg).

After stirring for 17 h, dichloromethane was removed in vacuo. The remaining solution was cooled to 0° C., during which a solid formed. The solid was collected by filtration, washed with cold methanol, and then purified by preparative HPLC (Method B).

Yield: 90 mg. MS-ESI: [M+H]$^+$=564.4/566.4; anal. HPLC: R$_t$=16.18 min. (diast.1) R$_t$=16.71 min. (diast.2) (method 1)

Diast. ratio: 10:1

EXAMPLE 14

Propane-1-sulfonic acid [5-(3-cyano-2-methyl-5-oxo-7-propyl-1,4,5,6,7,8-hexahydro-quinolin-4-yl)-3-ethoxy-2-(3-methoxy-benzyloxy)-phenyl]-amide (a). 3-Ethoxy-4-hydroxy-5-nitro-benzaldehyde To a solution of 3-ethoxy-4-hydroxybenzaldehyde (5 g) in acetic acid (50 ml) was added nitric acid (1.4 ml) in 2 portions. The resulting suspension was stirred for 17 h. The solid was collected by filtration, washed with water and dried in vacuo.

Yield: 5.07 g.

(b). 4-(3-Ethoxy-4-hydroxy-5-nitro-phenyl)-2-methyl-5-oxo-7-propyl-1,4,5,6,7,8-hexahydro-quinoline-3-carbonitrile A mixture of 3-ethoxy-4-hydroxy-5-nitro-benzaldehyde (1.5 g), 3-aminocrotonitrile (584 mg) and 5-propylcyclohexane-1,3-dione (1.09 g) in ethanol (60 ml) was heated at reflux for 17 h. The mixture was concentrated in vacuo. The residue was purified by chromatography on silicagel in heptane/ethyl acetate 1/0→0/1 (v/v) as eluent.

Yield: 1.3 g. MS-ESI: [M+H]$^+$=412.3 (c). 4-[3-Ethoxy-4-(3-methoxy-benzyloxy)-5-nitro-phenyl]-2-methyl-5-oxo-7-propyl-1,4,5,6,7,8-hexahydro-quinoline-3-carbonitrile A mixture of 4-(3-ethoxy-4-hydroxy-5-nitro-phenyl)-2-methyl-5-oxo-7-propyl-1,4,5,6,7,8-hexahydro-quinoline-3-carbonitrile (1.5 g), 3-methoxybenzyl bromide (2.56 ml), potassium hydroxyde (450 mg) and benzyltriethyl ammonium chloride (415 mg) in 60 ml of dichloromethane and 60 ml of water was stirred for 48 h. The organic layer was separated, dried (MgSO$_4$), filtered, and concentrated in vacuo. The residue was purified by chromatography on silicagel in heptane/ethyl acetate 7/3→4/6 (v/v) as eluent.

Yield: 1.2 g. MS-ESI: [M+H]$^+$=532.3

(d). 4-[3-Amino-5-ethoxy-4-(3-methoxy-benzyloxy)-phenyl]-2-methyl-5-oxo-7-propyl-1,4,5,6,7,8-hexahydro-quinoline-3-carbonitrile A solution of 4-[3-ethoxy-4-(3-methoxy-benzyloxy)-5-nitro-phenyl]-2-methyl-5-oxo-7-propyl-1,4,5,6,7,8-hexahydro-quinoline-3-carbonitrile and acetic acid (1.3 ml) in THF (33 ml) was cooled to 0° C. Zinc dust (3.02 g) was added in portions under vigorous stirring. The mixture was allowed to reach room temperature and stirred for 1 h. The mixture was then filtered and concentrated in vacuo. The residue was dissolved in dichloromethane and washed with sat. aq. NaHCO$_3$. The organic layer was dried (MgSO$_4$), filtered and concentrated in vacuo.

Yield: 1.1 g. MS-ESI: [M+H]$^+$=502.3

(e). Propane-1-sulfonic acid [5-(3-cyano-2-methyl-5-oxo-7-propyl-1,4,5,6,7,8-hexahydro-quinolin-4-yl)-3-ethoxy-2-(3-methoxy-benzyloxy)-phenyl]-amide To a solution of 4-[3-amino-5-ethoxy-4-(3-methoxy-benzyloxy)-phenyl]-2-methyl-5-oxo-7-propyl-1,4,5,6,7,8-hexahydro-quinoline-3-carbonitrile (220 mg) and pyridine (106 µl) in dichloromethane (5 ml) was added propane-1-sulfonyl chloride (94 mg). After stirring for 17 h, the mixture was diluted with dichloromethane and extracted with water and sat. aq. NaHCO$_3$. The organic layer was dried (MgSO$_4$), filtered and concentrated in vacuo. The residue was purified by preparative HPLC (Method B).

Yield: 41 mg. MS-ESI: [M+H]$^+$=608.4; anal. HPLC: R$_t$=20.50 min. (method 1)

Diast. ratio: 5:1

EXAMPLE 15

N-[3-Bromo-5-(3-cyano-2-methyl-5-oxo-7-propyl-1,4,5,6,7,8-hexahydro-quinolin-4-yl)-2-(3-methoxy-benzylamino)-phenyl]-methanesulfonamide (a). 4-Amino-3-nitro-benzaldehyde 4-Fluoro-3-nitrobenzaldehyde (3 g) was slowly added to 50 ml of conc. aq. NH$_4$OH. After stirring for 3 h, the mixture was diluted with water and extracted with dichloromethane. The organic layer was dried (MgSO$_4$), filtered and concentrated in vacuo. The residue was purified by chromatography on silicagel in heptane/ethyl acetate 1/0→0/1 (v/v) as eluent.

Yield: 2.1 g. MS-ESI: [M+H]$^+$=167.2

(b). 4-Amino-3-bromo-5-nitro-benzaldehyde

4-Amino-3-nitro-benzaldehyde (2.1 g) was dissolved in 25 ml of dichloromethane. Bromine (2 ml) and acetic acid (1 ml) were added and the mixture was stirred for 2 h at room temperature. The mixture was diluted with ethyl acetate and washed with aq. NaHSO$_3$. The organic layer was dried (MgSO$_4$), filtered and concentrated in vacuo. The residue was purified by chromatography on silicagel in heptane/ethyl acetate 1/0→0/1 (v/v) as eluent.

Yield: 2.5 g. MS-ESI: [M+H]$^+$=245.0/247.0

(c). 4-(4-Amino-3-bromo-5-nitro-phenyl)-2-methyl-5-oxo-7-propyl-1,4,5,6,7,8-hexahydro-quinoline-3-carbonitrile A mixture of 4-amino-3-bromo-5-nitro-benzaldehyde (665 mg), 3-aminocrotonitrile (223 mg), 5-propylcyclohexane-1,3-dione (418 mg) in 50 ml of ethanol was stirred at 80° C. for 4 h, then at room temperature for 16 h. The reaction mixture was concentrated in vacuo. The residue was purified by chromatography on silicagel in heptane/ethyl acetate 1/0→0/1 (v/v) as eluent.

Yield: 680 mg. MS-ESI: $[M+H]^+$=445.2/447.2

(d). 4-(3,4-Diamino-5-bromo-phenyl)-2-methyl-5-oxo-7-propyl-1,4,5,6,7,8-hexahydro-quinoline-3-carbonitrile 4-(4-Amino-3-bromo-5-nitro-phenyl)-2-methyl-5-oxo-7-propyl-1,4,5,6,7,8-hexahydro-quinoline-3-carbonitrile (600 mg) was dissolved in THF (150 ml) and cooled to 0° C. Acetic acid (1.3 ml) was added, followed by addition of zinc dust (2 g). The resulting slurry was stirred at 0° C. for 2 h, and then another 4 h at room temperature. The mixture was filtered and diluted with saturated aq. $NaHCO_3$, followed by extraction with ethyl acetate. The organic layer was dried ($MgSO_4$), filtered and concentrated in vacuo. The residue was purified by chromatography on silicagel in heptane/ethyl acetate 3/1→0/1 (v/v) as eluent.

Yield: 316 mg. MS-ESI: $[M+H]^+$=415.2/417.2

(e). [2-Amino-3-bromo-5-(3-cyano-2-methyl-5-oxo-7-propyl-1,4,5,6,7,8-hexahydro-quinolin-4-yl)-phenyl]-carbamic acid 9H-fluoren-9-yl methyl ester 4-(3,4-Diamino-5-bromo-phenyl)-2-methyl-5-oxo-7-propyl-1,4,5,6,7,8-hexahydro-quinoline-3-carbonitrile (316 mg) and N,N-dimethylaniline (195 µl) were dissolved in dichloromethane (40 ml) and cooled to 0° C. A solution of 9-fluorenylmethyl chloroformate (187 mg) in dichloromethane (3 ml) was added dropwise. After stirring for 2 h, the reaction mixture was diluted with water and extracted with ethyl acetate. The organic layer was dried ($MgSO_4$), filtered and concentrated in vacuo. The residue was purified by chromatography on silicagel in heptane/ethyl acetate 1/0→0/1 (v/v) as eluent.

Yield: 381 mg.

(f). [3-Bromo-5-(3-cyano-2-methyl-5-oxo-7-propyl-1,4,5,6,7,8-hexahydro-quinolin-4-yl)-2-(3-methoxy-benzylamino)-phenyl]-carbamic acid 9H-fluoren-9-yl methyl ester To a solution of [2-amino-3-bromo-5-(3-cyano-2-methyl-5-oxo-7-propyl-1,4,5,6,7,8-hexahydro-quinolin-4-yl)-phenyl]-carbamic acid 9H-fluoren-9-yl methyl ester in methanol (5 ml) was added acetic acid (143 µl) and m-anisaldehyde (304 µl). After stirring for 2 h, sodium cyanoborohydride (158 mg) was added. The resulting mixture was stirred for 3 h and then quenched with water, followed by extraction with ethyl acetate. The organic layer was dried ($MgSO_4$), filtered and concentrated in vacuo. The residue was purified by chromatography on silicagel in heptane/ethyl acetate 1/0→0/1 (v/v) as eluent.

Yield: 145 mg. MS-ESI: $[M+H]^+$=757.6/759.6

(g). 4-[3-Amino-5-bromo-4-(3-methoxy-benzylamino)-phenyl]-2-methyl-5-oxo-7-propyl-1,4,5,6,7,8-hexahydro-quinoline-3-carbonitrile

[3-Bromo-5-(3-cyano-2-methyl-5-oxo-7-propyl-1,4,5,6,7,8-hexahydro-quinolin-4-yl)-2-(3-methoxy-benzylamino)-phenyl]-carbamic acid 9H-fluoren-9-yl methyl ester (145 mg) was dissolved in 20% piperidine in DMF (5 ml) and stirred for 1 hour. The reaction mixture was diluted with water and extracted with ethyl acetate. The organic layer was dried ($MgSO_4$), filtered and concentrated in vacuo. The residue was purified by preparative HPLC (Method B).

Yield: 70 mg. MS-ESI: $[M+H]^+$=535.4/537.4

(h). N-[3-Bromo-5-(3-cyano-2-methyl-5-oxo-7-propyl-1,4,5,6,7,8-hexahydro-quinolin-4-yl)-2-(3-methoxy-benzylamino)-phenyl]-methanesulfonamide To a solution of 4-[3-amino-5-bromo-4-(3-methoxy-benzylamino)-phenyl]-2-methyl-5-oxo-7-propyl-1,4,5,6,7,8-hexahydro-quinoline-3-carbonitrile (70 mg) and pyridine (40 µl) in 1 ml of dichloromethane was added methanesulfonyl chloride (50 µl) in portions until complete conversion was observed as judged by TLC (eluent: heptane/ethyl acetate 1/1, v/v). The reaction mixture was diluted with water and extracted with ethyl acetate. The organic layer was dried ($MgSO_4$), filtered and concentrated in vacuo. The residue was purified by preparative HPLC (Method A).

Yield: 18 mg (as TFA salt). MS-ESI: $[M+H]^+$=613.4/615.4; anal. HPLC: $R_t$=21.27 min. (method 2)

EXAMPLE 16

3-Bromo-5-(3-cyano-2-methyl-5-oxo-7-propyl-1,4,5,6,7,8-hexahydro-quinolin-4-yl)-2-(3-nitro-benzyloxy)-benzoic acid methyl ester (a). 5-Formyl-2-hydroxy-benzoic acid methyl ester 5-Formyl-2-hydroxy-benzoic acid (11.3 g) was dissolved in methanol (35 ml) and conc. sulfuric acid (3 ml). The mixture was heated at reflux for 40 h. Diethyl ether was added, and the mixture was poured into water. The organic layer was dried ($MgSO_4$), filtered and concentrated in vacuo. The residue was dissolved in a mixture of dioxane (80 ml) and water (50 ml) and treated with 6N hydrochloric acid (2.5 ml). After 15 min., dioxane was removed in vacuo. The mixture was extracted with ethyl acetate. The organic layer was dried ($MgSO_4$), filtered and concentrated in vacuo.

Yield: 8.23 g. MS-ESI: $[M+H]^+$=181.2

(b). 3-Bromo-5-formyl-2-hydroxy-benzoic acid methyl ester

To a solution of 5-formyl-2-hydroxy-benzoic acid methyl ester (7.93 g) in acetic acid (50 ml) and dichloromethane (40 ml), cooled to 0° C., was added bromine (2.49 ml). After stirring for 17 h, the mixture was allowed to reach room temperature. Sodium acetate (3.61 g) was added and stirring was continued for 1 h. The mixture was diluted with water and extracted with ethyl acetate. The organic layer was dried ($MgSO_4$), filtered and concentrated in vacuo.

Yield: 11.88 g. MS-ESI: $[M+H]^+$=259.0/261.0

(c). 3-Bromo-5-formyl-2-(3-nitro-benzyloxy)-benzoic acid methyl ester

A mixture of 3-bromo-5-formyl-2-hydroxy-benzoic acid methyl ester (518 mg), potassium carbonate (613 mg), tetrabutylammonium iodide (68 mg) and 3-nitrobenzyl bromide (525 mg) in DMF (10 ml) was heated at 60° C. for 5 h. The mixture was diluted with water and extracted with ethyl acetate. The organic layer was dried (MgSO$_4$), filtered and concentrated in vacuo.

Yield: 851 mg. MS-ESI: [M+H]$^+$=394.0/396.0

(d). 3-Bromo-5-(3-cyano-2-methyl-5-oxo-7-propyl-1,4,5,6,7,8-hexahydro-quinolin-4-yl)-2-(3-nitro-benzyloxy)-benzoic acid methyl ester A mixture of 3-bromo-5-formyl-2-(3-nitro-benzyloxy)-benzoic acid methyl ester (788 mg), 3-aminocrotonitrile (165 mg) and 5-propylcyclohexane-1,3-dione (308 mg) in ethanol (5 ml) was heated at 80° C. for 17 h. The mixture was concentrated in vacuo. The residue was purified by preparative HPLC (Method B).

Yield: 1.37 g. MS-ESI: [M+H]$^+$=594.4/596.4; anal. HPLC: R$_t$=24.59 min. (diast.1) R$_t$=24.89 min. (diast.2) (method 2)

EXAMPLE 17

Propane-1-sulfonic acid {3-bromo-5-(3-cyano-2-methyl-5-oxo-7-propyl-1,4,5,6,7,8-hexahydro-quinolin-4-yl)-2-[(pyridin-3-ylmethyl)-amino]-phenyl}-amide (a). Propane-1-sulfonic acid [2-amino-3-bromo-5-(3-cyano-2-methyl-5-oxo-7-propyl-1,4,5,6,7,8-hexahydro-quinolin-4-yl)-phenyl]-amide The compound described in example 15d (4 g) was dissolved in 250 ml of dichloromethane. Pyridine (1.5 ml) was added, followed by dropwise addition of a solution of propanesulfonyl chloride (1.03 ml) in 50 ml of dichloromethane. The mixture was stirred for 17 h, and then washed with water. The organic layer was dried (MgSO$_4$), filtered and concentrated in vacuo.

Yield: 5.44 g. MS-ESI: [M+H]$^+$=521.4/523.4

(b). Propane-1-sulfonic acid {3-bromo-5-(3-cyano-2-methyl-5-oxo-7-propyl-1,4,5,6,7,8-hexahydro-quinolin-4-yl)-2-r[(pyridin-3-ylmethyl)-amino]-phenyl}-amide Propane-1-sulfonic acid [2-amino-3-bromo-5-(3-cyano-2-methyl-5-oxo-7-propyl-1,4,5,6,7,8-hexahydro-quinolin-4-yl)-phenyl]-amide (842 mg) and acetic acid (950 µl) were dissolved in methanol (25 ml). 3-Pyridine-carboxaldehyde (1.52 ml) was added and the resulting mixture was stirred for 17 h. Sodium cyanoborohydride (1.02 g) was added and stirring was continued for 17 h. The mixture was diluted with ethyl acetate and washed with aq. citric acid and aq. NaHCO$_3$. The organic layer was dried (MgSO$_4$), filtered and concentrated in vacuo. The residue was purified by preparative HPLC (Method A).

Yield: 237 mg (as TFA salt). MS-ESI: [M+H]$^+$=612.4/614.4; anal. HPLC: R$_t$=8.79 min. (method 2)

EXAMPLE 18

3-Bromo-5-(3-cyano-2-methyl-5-oxo-7-propyl-1,4,5,6,7,8-hexahydro-quinolin-4-yl)-2-(3-methoxy-benzyloxy)-N-propyl-benzamide A mixture of the compound described in example 22c (100 mg), n-propylamine (145 µl), TBTU (75 mg) and N,N-diisopropylethylamine (31 µl) in dichloromethane (10 ml) was stirred for 65 h. The mixture was diluted with dichloromethane and extracted with sat. aq. NaHCO$_3$. The organic layer was dried (MgSO$_4$), filtered and concentrated in vacuo. The residue was purified by preparative HPLC (Method B).

Yield: 41 mg. MS-ESI: [M+H]$^+$=605.4/607.4; anal. HPLC: R$_t$=26.72 min. (diast.1) R$_t$=27.01 min. (diast.2) (method 2)

EXAMPLE 19

4-{[2-Bromo-4-(3-cyano-2-methyl-5-oxo-7-propyl-1,4,5,6,7,8-hexahydro-quinolin-4-yl)-6-(propane-1-sulfonylamino)-phenylamino]-methyl}-N-(2-methoxy-ethyl)-benzamide (a). 4-{[2-Bromo-4-(3-cyano-2-methyl-5-oxo-7-propyl-1,4,5,6,7,8-hexahydro-quinolin-4-yl)-6-(propane-1-sulfonylamino)-phenylamino]-methyl}-benzoic acid A mixture of the compound described in example 17a (600 mg), benzoic acid-4-carboxaldehyde (863 mg) and acetic acid (657 µl) in methanol (5 ml) was stirred for 1 hour. Sodium cyanoborohydride (361 mg) was added and the mixture was stirred for 17 h. The reaction mixture was diluted with ethyl acetate and washed with water. The organic layer was dried (MgSO$_4$), filtered and concentrated in vacuo.

Yield: 605 mg. MS-ESI: [M+H]$^+$=655.4/657.4

(b). 4-{[2-Bromo-4-(3-cyano-2-methyl-5-oxo-7-propyl-1,4,5,6,7,8-hexahydro-quinolin-4-yl)-6-(propane-1-sulfonylamino)-phenylamino]-methyl}-N-(2-methoxy-ethyl)-benzamide A mixture of 4-{[2-bromo-4-(3-cyano-2-methyl-5-oxo-7-propyl-1,4,5,6,7,8-hexahydro-quinolin-4-yl)-6-(propane-1-sulfonylamino)-phenylamino]-methyl}-benzoic acid (200 mg), TBTU (300 mg), N,N-diisopropylethylamine (536 µl) and 2-methoxyethylamine (134 µl) in DMF (2 ml) was stirred for 2 h at room temperature. The mixture was diluted with ethyl acetate and washed with aq. NaHCO$_3$.

The organic layer was dried (MgSO$_4$), filtered and concentrated in vacuo.

The residue was purified by preparative HPLC (Method B).

Yield: 115 mg. MS-ESI: [M+H]$^+$=712.4/714.4; anal. HPLC: R$_t$=17.99 min. (method 2)

EXAMPLE 20

4-{[2-Bromo-4-(3-cyano-2-methyl-5-oxo-7-propyl-1,4,5,6,7,8-hexahydro-quinolin-4-yl)-6-(propane-1-sulfonylamino)-phenylamino]-methyl}-N-[2-(1H-imidazol-4-yl)-ethyl]-benzamide Condensation of histamine (283 mg) and the compound described in example 19a (200 mg) in the presence of TBTU (300 mg) and N,N-diisopropylethylamine (536 µl) was performed according to the method described in example 19b.

Yield: 123 mg (as TFA salt). MS-ESI: [M+H]$^+$=748.4/750.4; anal. HPLC: R$_t$=10.38 min. (method 2)

EXAMPLE 21

4-[3-Bromo-4-(3-methoxy-benzyloxy)-5-(morpholine-4-carbonyl)-phenyl]-2-methyl-5-oxo-7-propyl-1,4,5,6,7,8-hexahydro-quinoline-3-carbonitrile A mixture of the compound described in example 22c (100 mg), morpholine (50 µl), HATU (100 mg) and N,N-diisopropylethylamine (92 µl) in dichloromethane (5 ml) was stirred for 17 h. The mixture was diluted with dichloromethane and extracted with sat. aq. NaHCO$_3$. The organic layer was dried (MgSO$_4$), filtered and concentrated in vacuo. The residue was purified by preparative HPLC (Method B).

Yield: 54 mg. MS-ESI: [M+H]$^+$=634.4/636.4; anal. HPLC: R$_t$=21.32 min. (method 2)

EXAMPLE 22

3-Bromo-5-(3-cyano-2-methyl-5-oxo-7-propyl-1,4,5,6,7,8-hexahydro-quinolin-4-yl)-2-(3-methoxy-benzyloxy)-benzamide (a). 3-Bromo-5-formyl-2-(3-methoxy-benzyloxy)-benzoic acid methyl ester A mixture of the compound described in example 16b (4.62 g), 3-methoxybenzyl bromide (3.03 ml), potassium carbonate (5.47 g) and tetrabutylammonium iodide (606 mg) in DMF (90 ml) was stirred at 60° C. for 5 h. The mixture was poured into water and extracted with ethyl acetate. The organic layer was dried (MgSO$_4$), filtered and concentrated in vacuo. The residue was recrystallized from ethanol and diethylether (1/1, v/v).

Yield: 5.65 g.

(b). 3-Bromo-5-(3-cyano-2-methyl-5-oxo-7-propyl-1,4,5,6,7,8-hexahydro-quinolin-4-yl)-2-(3-methoxy-benzyloxy)-benzoic acid methyl ester A mixture of 3-bromo-5-formyl-2-(3-methoxy-benzyloxy)-benzoic acid methyl ester (3.78 g), 3-aminocrotonitrile (822 mg) and 5-propylcyclohexane-1,3-dione (1535 mg) in ethanol (25 ml) was stirred at 80° C. for 17 h. The mixture was concentrated in vacuo.

Yield: 5.9 g.

(c). 3-Bromo-5-(3-cyano-2-methyl-5-oxo-7-propyl-1,4,5,6,7,8-hexahydro-quinolin-4-yl)-2-(3-methoxy-benzyloxy)-benzoic acid A solution of 3-bromo-5-(3-cyano-2-methyl-5-oxo-7-propyl-1,4,5,6,7,8-hexahydro-quinolin-4-yl)-2-(3-methoxy-benzyloxy)-benzoic acid methyl ester (5.7 g) in dioxane (135 ml) and 1N NaOH (15 ml) was stirred for 17 h. The mixture was acidified with conc. acetic acid and extracted with ethyl acetate. The organic layer was dried (MgSO$_4$), filtered and concentrated in vacuo. The residue was dissolved in ethanol and then concentrated until a solid precipitated. The solid was collected by filtration and washed with petroleum ether.

Yield: 4.2 g. MS-ESI: [M+H]$^+$=563.6/565.2

(d). 3-Bromo-5-(3-cyano-2-methyl-5-oxo-7-propyl-1,4,5,6,7,8-hexahydro-quinolin-4-yl)-2-(3-methoxy-benzyloxy)-benzamide A mixture of 3-bromo-5-(3-cyano-2-methyl-5-oxo-7-propyl-1,4,5,6,7,8-hexahydro-quinolin-4-yl)-2-(3-methoxy-benzyloxy)-benzoic acid (57 mg), ammonium chloride (18 mg), HATU (57 mg) and N,N-diisopropylethylamine (34 µl) in DMF (0.8 ml) was stirred for 17 h. The mixture was diluted with water and extracted with ethyl acetate.

The organic layer was dried (MgSO$_4$), filtered and concentrated in vacuo. The residue was purified by preparative HPLC (Method B).

Yield: 29 mg. MS-ESI: [M+H]$^+$=564.4/566.4; anal. HPLC: R$_t$: 19.64 min. (method 2)

EXAMPLE 23

N-[2-Bromo-4-(3-cyano-2-methyl-5-oxo-7-propyl-1,4,5,6,7,8-hexahydro-quinolin-4-yl)-6-(propane-1-sulfonylamino)-phenyl]-3-methoxy-benzamide A solution of the compound described in example 17a (229 mg) and N,N-dimethylaniline (480 mg) in THF (4 ml) was treated with 75 µl of 3-methoxybenzoyl chloride.

After stirring for 17 h, the mixture was diluted with ethyl acetate and washed with water. The organic layer was dried (MgSO$_4$), filtered and concentrated in vacuo. The residue was purified by preparative HPLC (Method B).

Yield: 151 mg. MS-ESI: [M+H]$^+$=655.4/657.4; anal. HPLC: R$_t$=20.82 min. (method 2)

EXAMPLE 24

N-[3-Bromo-5-(3-cyano-2-methyl-5-oxo-7-propyl-1,4,5,6,7,8-hexahydro-quinolin-4-yl)-2-(3-methanesulfonylamino-benzyloxy)-phenyl]-methanesulfonamide (a). 3-Bromo-4-hydroxy-5-nitro-benzaldehyde To a solution of 3-bromo-4-hydroxy-benzaldehyde (20 g) in acetic acid (200 ml) was added fuming nitric acid (4.18 ml). The resulting suspension was stirred for 3 h. The solid was collected by filtration. Another 420 µl of fuming nitric acid was added to the filtrate. After 45 min., water was added and the resulting precipitate was collected by filtration. The combined solids were washed with water and dried in vacuo.

Yield: 18.26 g. MS-ESI: [M+H]$^+$=245.8/247.8

(b). 4-(3-Bromo-4-hydroxy-5-nitro-phenyl)-2-methyl-5-oxo-7-propyl-1,4,5,6,7,8-hexahydro-quinoline-3-carbonitrile A mixture of 3-bromo-4-hydroxy-5-nitro-benzaldehyde (18.26 g), 3-aminocrotonitrile (6.09 g) and 5-propylcyclohexane-1,3-dione (11.45 g) in ethanol (250 ml) was stirred at 80° C. for 17 h. The mixture was concentrated in vacuo. The residue was purified by chromatography on silicagel in dichloromethane as eluent.

Yield: 16.49 g. MS-ESI: [M+H]$^+$=446.2/448.2

(c). 4-(3-Amino-5-bromo-4-hydroxy-phenyl)-2-methyl-5-oxo-7-propyl-1,4,5,6,7,8-hexahydro-quinoline-3-carbonitrile To a solution of 4-(3-bromo-4-hydroxy-5-nitro-phenyl)-2-methyl-5-oxo-7-propyl-1,4,5,6,7,8-hexahydro-quinoline-3-carbonitrile (15.8 g) and acetic acid (30 ml) in THF (300 ml), zinc dust (46 g) was added in portions, under vigorous stirring. After 2 h, the mixture was filtered and concentrated until a precipitate formed. This precipitate was collected by filtration and washed with ethanol.

Yield: 9.27 g. MS-ESI: [M+H]$^+$=416.2/418.2

(d). 4-[3-Amino-5-bromo-4-(3-nitro-benzyloxy)-phenyl]-2-methyl-5-oxo-7-propyl-1,4,5,6,7,8-hexahydro-quinoline-3-carbonitrile A mixture of 4-(3-amino-5-bromo-4-hydroxy-phenyl)-2-methyl-5-oxo-7-propyl-1,4,5,6,7,8-hexahydro-quinoline-3- carbonitrile (5 g), 3-nitrobenzyl bromide (2.72 g), potassium carbonate (3.65 g) and potassium iodide (400 mg) in DMF (100 ml) was stirred for 65 h at room temperature. The mixture was diluted with ethyl acetate and washed with water. The organic layer was dried (MgSO$_4$), filtered and concentrated in vacuo. The residue was purified by chromatography on silicagel in heptane/ethyl acetate 1/0→0/1 (v/v) as eluent.

Yield: 1.45 g. MS-ESI: [M+H]$^+$=551.4/553.4

(e). N-[3-Bromo-5-(3-cyano-2-methyl-5-oxo-7-propyl-1,4,5,6,7,8-hexahydro-quinolin-4-yl)-2-(3-nitro-benzyloxy)-phenyl]-methanesulfonamide A solution of 4-[3-amino-5-bromo-4-(3-nitro-benzyloxy)-phenyl]-2-methyl-5-oxo-7-propyl-1,4,5,6,7,8-hexahydro-quinoline-3-carbonitrile (1.15 g) and triethylamine (740 µl) in dichloromethane (20 ml) was treated with methanesulfonyl chloride (203 µl). After stirring for 18 h, the mixture was diluted with ethyl acetate and washed with water. The organic layer was dried (MgSO$_4$), filtered and concentrated in vacuo. The crude N,N-bis-methanesulfonyl-aniline derivative was dissolved in THF (20 ml) and treated with 2N NaOH (3 ml). After 2 h, the mixture was quenched with sat. aq. NH$_4$Cl and extracted with ethyl acetate. The organic layer was dried (MgSO$_4$), filtered and concentrated in vacuo. The residue was purified by chromatography on silicagel in heptane/ethyl acetate 1/0→0/1 (v/v) as eluent.

Yield: 950 mg. MS-ESI: [M+H]$^+$=629.2/631.2

(f). N-[2-(3-Amino-benzyloxy)-3-bromo-5-(3-cyano-2-methyl-5-oxo-7-propyl-1,4,5,6,7,8-hexahydro-quinolin-4-yl)-phenyl]-methanesulfonamide A mixture of N-[3-bromo-5-(3-cyano-2-methyl-5-oxo-7-propyl-1,4,5,6,7,8-hexahydro-quinolin-4-yl)-2-(3-nitro-benzyloxy)-phenyl]-methanesulfonamide (950 mg) and sodium sulfide (350 mg) in ethanol (12 ml) and water (250 µl) was heated at reflux for 2 h. The mixture was diluted with ethyl acetate and washed with water. The organic layer was dried (MgSO$_4$), filtered and concentrated in vacuo.

Yield: 709 mg. MS-ESI: [M+H]$^+$=599.2/601.2

(g). N-[3-Bromo-5-(3-cyano-2-methyl-5-oxo-7-propyl-1,4,5,6,7,8-hexahydro-quinolin-4-yl)-2-(3-methanesulfonylamino-benzyloxy)-phenyl]-methanesulfonamide To a solution of N-[2-(3-amino-benzyloxy)-3-bromo-5-(3-cyano-2-methyl-5-oxo-7-propyl-1,4,5,6,7,8-hexahydro-quinolin-4-yl)-phenyl]-methanesulfonamide (709 mg) and pyridine (286 µl) in dichloromethane (20 ml) was added methanesulfonyl chloride (138 µl). After stirring for 18 h, the mixture was diluted with ethyl acetate and washed with water. The organic layer was dried (MgSO$_4$), filtered and concentrated in vacuo. The residue was purified by preparative HPLC (Method B).

Yield: 172 mg. MS-ESI: [M+H]$^+$=677.2/679.2; anal. HPLC: R$_t$=22.37 min. (method 3)

EXAMPLE 25

4-[3-Bromo-5-cyano-4-(3-methoxy-benzyloxy)-phenyl]-2-methyl-5-oxo-7-propyl-1,4,5,6,7,8-hexahydro-quinoline-3-carbonitrile A solution of the compound described in example 22d (54 mg) in dichloromethane (1.2 ml) was cooled to 0° C. Triethylamine (58 µl) was added, followed by dropwise addition of trifluoroacetic anhydride (25 µl). The mixture was allowed to reach room temperature. Again, triethylamine (58 µl) and trifluoroacetic anhydride (25 µl) were added. After stirring for 1 h, the mixture was extracted with water. The organic layer was dried (MgSO$_4$), filtered and concentrated in vacuo. The residue was purified by preparative HPLC (Method B).

Yield: 26 mg. MS-ESI: [M+H]$^+$=546.2/548.2; anal. HPLC: R$_t$=24.86 min. (method 2)

EXAMPLE 26

N-[2-Bromo-4-(3-cyano-2-methyl-5-oxo-7-propyl-1,4,5,6,7,8-hexahydro-quinolin-4-yl)-6-(propane-1-sulfonylamino)-phenyl]-N-(3-methoxy-benzyl)-acetamide (a). Propane-1-sulfonic acid [3-bromo-5-(3-cyano-2-methyl-5-oxo-7-propyl-1,4,5,6,7,8-hexahydro-quinolin-4-yl)-2-(3-methoxy-benzylamino)-phenyl]-amide Condensation of the compound described in example 17a (688 mg) with m-anisaldehyde (605 µl) in the presence of acetic acid (570 µl) and sodium cyanoborohydride (317 mg) in methanol (6 ml) was performed as described in example 17b.

Yield: 300 mg. MS-ESI: [M+H]$^+$=641.4/643.4

(b). N-[2-Bromo-4-(3-cyano-2-methyl-5-oxo-7-propyl-1,4,5,6,7,8-hexahydro-quinolin-4-yl)-6-(propane-1-sulfonylamino)-phenyl]-N-(3-methoxy-benzyl)-acetamide A solution of propane-1-sulfonic acid [3-bromo-5-(3-cyano-2-methyl-5-oxo-7-propyl-1,4,5,6,7,8-hexahydro-quinolin-4-yl)-2-(3-methoxy-benzylamino)-phenyl]-amide (120 mg) in pyridine (3 ml) was treated with acetic anhydride (153 µl). After stirring for 17 h, the mixture was diluted with ethyl acetate and washed with water. The organic layer was dried (MgSO$_4$), filtered and concentrated in vacuo. The residue was purified by chromatography on silicagel in heptane/ethyl acetate 1/0→0/1 (v/v) as eluent.

Yield: 27 mg. MS-ESI: [M+H]$^+$=683.2/685.2; anal. HPLC: R$_t$=21.09 min. (method 2)

EXAMPLE 27

Propane-1-sulfonic acid {3-bromo-5-(3-cyano-2-methyl-5-oxo-7-propyl-1,4,5,6,7,8-hexahydro-quinolin-4-yl)-2-[(3-methoxy-benzyl)-methyl-amino]-phenyl}-amide A mixture of the compound described in example 26a (180 mg), 37% formaldehyde in water (230 µl) and acetic acid (160 µl) in methanol (5 ml) was stirred for 2 h. Sodium cyanoborohydride (176 mg) was added and stirring was continued for 17 h. The mixture was diluted with ethyl acetate and washed with water. The organic layer was dried (MgSO$_4$), filtered and concentrated in vacuo.

The residue was purified by preparative HPLC (Method B).

Yield: 17 mg. MS-ESI: [M+H]$^+$=675.2/677.2; anal. HPLC: R$_t$=28.11 min. (method 2)

EXAMPLE 28

Propane-1-sulfonic acid [3-bromo-5-(3-cyano-2-methyl-5-oxo-7-propyl-1,4,5,6,7,8-hexahydro-quinolin-4-yl)-2-(3-methoxy-benzylamino)-phenyl]-methyl-amide A mixture of the compound described in example 26a (180 mg), methyl iodide (19 μl) and potassium carbonate (19 mg) in DMF (1 ml) was stirred for 65 h. The mixture was diluted with ethyl acetate and washed with water. The organic layer was dried (MgSO$_4$), filtered and concentrated in vacuo.

The residue was purified by preparative HPLC (Method B).

Yield: 31 mg. MS-ESI: [M+H]$^+$=655.4/657.4; anal. HPLC: R$_t$=25.00 min. (method 2)

EXAMPLE 29

N-[2-Bromo-4-(3-cyano-2-methyl-5-oxo-7-propyl-1,4,5,6,7,8-hexahydro-quinolin-4-yl)-6-(propane-1-sulfonylamino)-phenyl]-nicotinamide A mixture of the compound described in example 17a (100 mg), TBTU (123 mg), nicotinic acid (47 mg) and N,N-diisopropylethylamine (168 μl) in 2 ml of dichloromethane and 2 ml of THF was stirred for 65 h. The mixture was diluted with dichloromethane and extracted with water and sat. aq. NaHCO$_3$. The organic layer was dried (MgSO$_4$), filtered and concentrated in vacuo. The residue was purified by preparative HPLC (Method A).

Yield: 74 mg (as TFA salt). MS-ESI: [M+H]$^+$=626.4/628.4; anal. HPLC: R$_t$=12.03 min. (method 2)

EXAMPLE 30

N-(2-{[2-Bromo-4-(3-cyano-2-methyl-5-oxo-7-propyl-1,4,5,6,7,8-hexahydro-quinolin-4-yl)-6-(propane-1-sulfonylamino)-phenylamino]-methyl}-phenyl)-acetamide (a). Propane-1-sulfonic acid [3-bromo-5-(3-cyano-2-methyl-5-oxo-7-propyl-1,4,5,6,7,8-hexahydro-quinolin-4-yl)-2-(2-nitro-benzylamino)-phenyl]-amide Condensation of the compound described in example 17a (1.05 g) with 2-nitrobenzaldehyde (1.61 g) in the presence of acetic acid (1.21 ml) and sodium cyanoborohydride (1.34 g) in methanol (25 ml) was performed as described in example 17b.

Yield: 1.21 g. MS-ESI: [M+H]$^+$=676.2/678.2

(b). Propane-1-sulfonic acid [2-(2-amino-benzylamino)-3-bromo-5-(3-cyano-2-methyl-5-oxo-7-propyl-1,4,5,6,7,8-hexahydro-quinolin-4-yl)-phenyl]-amide Propane-1-sulfonic acid [3-bromo-5-(3-cyano-2-methyl-5-oxo-7-propyl-1,4,5,6,7,8-hexahydro-quinolin-4-yl)-2-(2-nitro-benzylamino)-phenyl]-amide (1.21 g) and acetic acid (1.6 ml) were dissolved in THF (150 ml). Zinc dust (2.32 g) was added under vigorous stirring. After 3 h, the mixture was filtered, diluted with ethyl acetate and washed with sat. aq. NaHCO$_3$. The residue was purified by chromatography on silicagel in heptane/ethyl acetate 1/0→0/1 (v/v) as eluent.

Yield: 430 mg. MS-ESI: [M+H]$^+$=626.4/628.4

(c). N-(2-{[2-Bromo-4-(3-cyano-2-methyl-5-oxo-7-propyl-1,4,5,6,7,8-hexahydro-quinolin-4-yl)-6-(propane-1-sulfonylamino)-phenylamino]-methyl}-phenyl)-acetamide A solution of propane-1-sulfonic acid [2-(2-amino-benzylamino)-3-bromo-5-(3-cyano-2-methyl-5-oxo-7-propyl-1,4,5,6,7,8-hexahydro-quinolin-4-yl)-phenyl]-amide (430 mg) and N,N-diisopropylethylamine (120 μl) in 1,2-dichloropropane (50 ml) was cooled to 0° C. and then treated with acetyl chloride (49 μl) in 1,2-dichloropropane (15 ml). After stirring for 2 h, the mixture was diluted with ethyl acetate and washed with water. The organic layer was dried (MgSO$_4$), filtered and concentrated in vacuo.

The residue was purified by preparative HPLC (Method A).

Yield: 45 mg (as TFA salt). MS-ESI: [M+H]$^+$=668.2/670.2; anal. HPLC: R$_t$=18.91 min. (method 2)

EXAMPLE 31

(2-{[2-Bromo-4-(3-cyano-2-methyl-5-oxo-7-propyl-1,4,5,6,7,8-hexahydro-quinolin-4-yl)-6-(propane-1-sulfonylamino)-phenylamino]-methyl}-phenyl)-carbamic acid methyl ester To a solution of the compound described in example 30b (100 mg) in dichloromethane (5 ml) was added N,N-diisopropylethylamine (84 μl) and methylchloroformate (12 μl). After stirring for 17 h, the mixture was diluted with ethyl acetate and washed with water. The organic layer was dried (MgSO$_4$), filtered and concentrated in vacuo. The residue was purified by preparative HPLC (Method A).

Yield: 19 mg (as TFA salt). MS-ESI: [M+H]$^+$=684.2/686.2; anal. HPLC: R$_t$=17.90 min. (method 2)

EXAMPLE 32

N-[2-Bromo-4-(3-cyano-2-methyl-5-oxo-7-propyl-1,4,5,6,7,8-hexahydro-quinolin-4-yl)-6-(propane-1-sulfonylamino)-phenyl]-3-(2-piperazin-1-yl-acetylamino)-benzamide (a). N-[2-Bromo-4-(3-cyano-2-methyl-5-oxo-7-propyl-1,4,5,6,7,8-hexahydro-quinolin-4-yl)-6-(propane-1-sulfonylamino)-phenyl]-3-nitro-benzamide To a solution of the compound described in example 17a (400 mg) and N,N-dimethylaniline (350 μl) in THF (10 ml) was added 3-nitrobenzoyl chloride (150 μl). The mixture was stirred for 17 h, then poured into water and extracted with ethyl acetate. The organic layer was dried (MgSO$_4$), filtered and concentrated in vacuo.

The residue was purified by chromatography on silicagel in heptane/ethyl acetate 1/3 (v/v) as eluent.

Yield: 412 mg. MS-ESI: [M+H]$^+$=670.2/672.2

(b). 3-Amino-N-[2-bromo-4-(3-cyano-2-methyl-5-oxo-7-propyl-1,4,5,6,7,8-hexahydro-quinolin-4-yl)-6-(propane-1-sulfonylamino)-phenyl]-benzamide To a solution of N-[2-bromo-4-(3-cyano-2-methyl-5-oxo-7-propyl-1,4,5,6,7,8-hexahydro-quinolin-4-yl)-6-(propane- 1-sulfonylamino)-phenyl]-3-nitro-benzamide (412 mg) and acetic acid (520 µl) in THF (10 ml), cooled to 0° C., was added zinc dust (810 mg) under vigorous stirring. After stirring for 4 h, the mixture was filtered and concentrated in vacuo. The residue was dissolved in dichloromethane and washed with water. The organic layer was dried (MgSO$_4$), filtered and concentrated in vacuo.

Yield: 257 mg. MS-ESI: [M+H]$^+$=640.4/642.4

(c). N-[2-Bromo-4-(3-cyano-2-methyl-5-oxo-7-propyl-14.5.6.7.8 hexahydro-quinolin-4-yl)-6-(propane-1-sulfonylamino)-phenyl]-3-(2-chloro-acetylamino)-benzamide To a solution of 3-amino-N-[2-bromo-4-(3-cyano-2-methyl-5-oxo-7-propyl-1,4,5,6,7,8-hexahydro-quinolin-4-yl)-6-(propane-1-sulfonylamino)-phenyl]-benzamide (257 mg) in THF (6 ml), N,N-diisopropylethylamine (205 µl) and chloroacetyl chloride (50 µl) were added. The mixture was stirred for 17 h, then diluted with dichloromethane and extracted with water and sat. aq. NaHCO$_3$. The organic layer was dried (MgSO$_4$), filtered and concentrated in vacuo.

Yield: 287 mg. MS-ESI: [M+H]$^+$=716.2/718.2

(d). N-[2-Bromo-4-(3-cyano-2-methyl-5-oxo-7-propyl-1,4,5,6,7,8-hexahydro-quinolin-4-yl)-6-(propane-1-sulfonylamino)-phenyl]-3-(2-piperazin-1-yl-acetylamino)-benzamide To a solution of N-[2-bromo-4-(3-cyano-2-methyl-5-oxo-7-propyl-1,4,5,6,7,8-hexahydro-quinolin-4-yl)-6-(propane-1-sulfonylamino)-phenyl]-3-(2-chloro-acetylamino)-benzamide (143 mg) in dichloromethane (4 ml) was added piperazine (172 mg). The mixture was stirred for 17 h, then diluted with dichloromethane and extracted with sat. aq. NaHCO$_3$. The organic layer was dried (MgSO$_4$), filtered and concentrated in vacuo.

The residue was purified by preparative HPLC (Method A).

Yield: 18 mg (as TFA salt). MS-ESI: [M+H]$^+$=766.4/768.4; anal. HPLC: R$_t$=4.87 min. (method 2)

EXAMPLE 33

4-[3-Bromo-5-(2-hydroxy-ethoxy)-4-(3-methoxy-benzyloxy)-phenyl]-2-methyl-5-oxo-7-propyl-1,4,5,6,7,8-hexahydro-quinoline-3-carbonitrile (a). 3-Bromo-5-hydroxy-4-(3-methoxy-benzyloxy)-benzaldehyde A mixture of 3-bromo-4,5-dihydroxy-benzaldehyde (1 g), lithium carbonate (314 mg), 3-methoxybenzyl chloride (742 µl) and a catalytic amount of tetrabutylammonium iodide in DMF (5 ml) was stirred at 60° C. for 17 h. The mixture was diluted with ethyl acetate and washed with water. The organic layer was dried (MgSO$_4$), filtered and concentrated in vacuo.

Yield: 1.48 g. MS-ESI: [M+H]$^+$=337.2/339.2

(b). 4-[3-Bromo-5-hydroxy-4-(3-methoxy-benzyloxy)-phenyl]-2-methyl-5-oxo-7-propyl-1,4,5,6,7,8-hexahydro-quinoline-3-carbonitrile A mixture of 3-bromo-5-hydroxy-4-(3-methoxy-benzyloxy)-benzaldehyde (1.43 g), 3-aminocrotonitrile (350 mg) and 5-propylcyclohexane-1,3-dione (654 mg) in ethanol (100 ml) was heated at 80° C. for 17 h. The mixture was concentrated in vacuo and then purified by chromatography on silicagel in heptane/ethyl acetate 1/0→0/1 (v/v) as eluent.

Yield: 1.31 g. MS-ESI: [M+H]$^+$=537.2/539.2

(c). 4-[3-Bromo-5-(2-hydroxy-ethoxy)-4-(3-methoxy-benzyloxy)-phenyl]-2-methyl-5-oxo-7-propyl-1,4,5,6,7,8-hexahydro-quinoline-3-carbonitrile A mixture of 4-[3-bromo-5-hydroxy-4-(3-methoxy-benzyloxy)-phenyl]-2-methyl-5-oxo-7-propyl-1,4,5,6,7,8-hexahydro-quinoline-3-carbonitrile (100 mg), 2-bromoethanol (16 µl), tetrabutylammonium iodide (5 mg) and potassium carbonate (50 mg) in DMF (2 ml) was stirred at 70° C. for 17 h. The mixture was diluted with ethyl acetate and washed with water. The organic layer was dried (MgSO$_4$), filtered and concentrated in vacuo.

The residue was purified by preparative HPLC (Method B).

Yield: 36 mg. MS-ESI: [M+H]$^+$=581.4/583.4; anal. HPLC: R$_t$=20.57 min. (diast.1) R$_t$=20.91 min. (diast.2) (method 2)

EXAMPLE 34

4-[3-Bromo-4-(3-methoxy-benzyloxy)-5-(2-methoxy-ethoxy)-phenyl]-2-methyl-5-oxo-7-propyl-1,4,5,6,7,8-hexahydro-quinoline-3-carbonitrile Alkylation of the compound described in example 33b (100 mg) using 2-methoxybromoethane (22 µl), potassium carbonate (50 mg) and tetrabutylammonium iodide (5 mg) in DMF (2 ml) was performed according to the method described in example 33c.

Yield: 48 mg. MS-ESI: [M+H]$^+$=595.2/597.2; anal. HPLC: R$_t$=24.72 min. (diast.1) R$_t$=25.08 min. (diast.2) (method 2)

EXAMPLE 35

4-[3-Bromo-5-hydroxy-4-(3-methoxy-benzyloxy)-phenyl]-2-methyl-5-oxo-7-propyl-1,4,5,6,7,8-hexahydro-quinoline-3-carbonitrile 100 mg of the compound described in example 33b was purified by preparative HPLC (Method B).

Yield: 54 mg. MS-ESI: [M+H]$^+$=537.4/539.4; anal. HPLC: R$_t$=21.85 min. (method 2)

EXAMPLE 36

3-Bromo-5-(3-cyano-2-methyl-5-oxo-7-propyl-1,4,5,6,7,8-hexahydro-quinolin-4-yl)-N,N-diethyl-2-(pyridin-3-ylmethoxy)-benzenesulfonamide (a). 3-Bromo-5-(3-cyano-2-methyl-5-oxo-7-propyl-1,4,5,6,7,8-hexahydro-quinolin-4-yl)-N,N-diethyl-2-hydroxy-benzenesulfonamide A mixture of the compound described in example 37b (1.5 g) and diethylamine (3.1 ml) in dioxane (30 ml) was stirred for 17 h. The mixture was diluted with ethyl acetate and washed with water. The organic layer was dried (MgSO$_4$), filtered and concentrated in vacuo.

Yield: 1.43 g. MS-ESI: [M+H]$^+$=536.2/538.2

(b). 3-Bromo-5-(3-cyano-2-methyl-5-oxo-7-propyl-1,4,5,6,7,8-hexahydro-quinolin-4-yl)-N,N-diethyl-2-(pyridin-3-ylmethoxy)-benzenesulfonamide A mixture of 3-bromo-5-(3-cyano-2-methyl-5-oxo-7-propyl-1,4,5,6,7,8-hexahydro-quinolin-4-yl)-N,N-diethyl-2-hydroxy-benzenesulfonamide (1.43 g), 3-picolyl chloride (689 mg), potassium carbonate (774 mg) and potassium iodide (93 mg) in DMF (40 ml) was stirred at 70° C. for 2 hours and then at room temperature for 17 h. The mixture was diluted with ethyl acetate and extracted with water. The organic layer was dried (MgSO$_4$), filtered and concentrated in vacuo. The residue was purified by preparative HPLC (Method A).

Yield: 991 mg (as TFA salt). MS-ESI: [M+H]$^+$=627.2/629.2; anal. HPLC: R$_t$=17.36 min. (method 3)

EXAMPLE 37

3-Bromo-5-(3-cyano-2-methyl-5-oxo-7-propyl-1,4,5,6,7,8-hexahydro-quinolin-4-yl)-N-methyl-2-(pyridin-3-ylmethoxy)-benzenesulfonamide (a). 4-(3-Bromo-4-hydroxy-phenyl)-2-methyl-5-oxo-7-propyl-1,4,5,6,7,8-hexahydro-quinoline-3-carbonitrile A mixture of 3-bromo-4-hydroxy-benzaldehyde (13.07 g), 5-propylcyclohexane-1,3-dione (10.02 g) and 3-aminocrotonitrile (5.34 g) in ethanol (165 ml) was stirred at 80° C. for 17 h. A precipitate formed, which was collected by filtration. The filtrate was concentrated in vacuo and then triturated with ethyl acetate. The solids were combined and dried in vacuo.

Yield: 20.25 g. MS-ESI: [M+H]$^+$=401.2/403.2

(b). 3-Bromo-5-(3-cyano-2-methyl-5-oxo-7-propyl-1,4,5,6,7,8-hexahydro-quinolin-4-yl)-2-hydroxy-benzenesulfonyl chloride To 47 ml of chlorosulfonic acid, cooled to −10° C. in a pressure vessel under a nitrogen atmosphere, was slowly added 4-(3-bromo-4-hydroxy-phenyl)-2-methyl-5-oxo-7-propyl-1,4,5,6,7,8-hexahydro-quinoline-3-carbonitrile (20.25 g). The mixture was allowed to reach room temperature. After stirring for 17 h, the mixture was poured onto 800 ml of crushed ice and extracted with ethyl acetate. The organic layer was dried (MgSO$_4$), filtered and concentrated in vacuo. The residue was triturated with ethyl acetate. The solids were collected and dried in vacuo.

Yield: 23.7 g. MS-ESI: [M+H]$^+$=499.0/501.0

(c). 3-Bromo-5-(3-cyano-2-methyl-5-oxo-7-propyl-1,4,5,6,7,8-hexahydro-quinolin-4-yl)-2-hydroxy-N-methyl-benzenesulfonamide For 30 min., mono-methylamine was bubbled through a solution of 3-bromo-5-(3-cyano-2-methyl-5-oxo-7-propyl-1,4,5,6,7,8-hexahydro-quinolin-4-yl)-2-hydroxy-benzenesulfonyl chloride (240 mg) in dioxane (5 ml). The mixture was stirred for 17 h. The reaction mixture was diluted with water and extracted with ethyl acetate. The organic layer was dried (MgSO$_4$), filtered and concentrated in vacuo. The residue was purified by preparative HPLC (Method B).

Yield: 60 mg. MS-ESI: [M+H]$^+$=494.2/494.2

(d). 3-Bromo-5-(3-cyano-2-methyl-5-oxo-7-propyl-1,4,5,6,7,8-hexahydro-quinolin-4-yl)-N-methyl-2-(pyridin-3-ylmethoxy)-benzenesulfonamide A mixture of 3-bromo-5-(3-cyano-2-methyl-5-oxo-7-propyl-1,4,5,6,7,8-hexahydro-quinolin-4-yl)-2-hydroxy-N-methyl-benzenesulfonamide (52 mg), 3-picolyl chloride. HCl (24 mg) and potassium carbonate (88 mg) in DMF (2 ml) was heated at 70° C. for 2 h, then at room temperature for 17 h. The reaction mixture was diluted with water and extracted with ethyl acetate. The organic layer was dried (MgSO$_4$), filtered and concentrated in vacuo. The residue was purified by preparative HPLC (Method A).

Yield: 15.5 mg (as TFA salt). MS-ESI: [M+H]$^+$=585.2/587.2; anal. HPLC: R$_t$=8.73 min. (diast.1) R$_t$=9.44 min. (diast.2) (method 2)

Diast. ratio: 10:1

EXAMPLE 38

4-[3-Bromo-5-hydroxy-4-(pyridin-3-ylmethoxy)-phenyl]-2-methyl-5-oxo-7-propyl-1,4,5,6,7,8-hexahydro-quinoline-3-carbonitrile (a). 3-Bromo-5-hydroxy-4-(pyridin-3-ylmethoxy)-benzaldehyde A mixture of 3-bromo-4,5-dihydroxy-benzaldehyde (1 g), 3-pyridinecarbinol (448 µl), diisopropyl azodicarboxylate (DIAD) (908 µl) and polymer supported triphenylphosphine (1.53 g, 3 mmol/g loading) in THF (50 ml) was stirred under a nitrogen atmosphere for 17 h. The mixture was filtered, diluted with ethyl acetate and washed with water. The organic layer was dried (MgSO$_4$), filtered and concentrated in vacuo. The residue was purified by chromatography on silicagel in heptane/ethyl acetate 1/0→0/1 (v/v) as eluent.

Yield: 330 mg. MS-ESI: [M+H]$^+$=308.2/310.2

(b). 4-[3-Bromo-5-hydroxy-4-(pyridin-3-ylmethoxy)-phenyl]-2-methyl-5-oxo-7-propyl-1,4,5,6,7,8-hexahydro-quinoline-3-carbonitrile A mixture of 3-bromo-5-hydroxy-4-(pyridin-3-ylmethoxy)-benzaldehyde (165 mg), 3-aminocrotonitrile (44 mg) and 5-propylcyclohexane-1,3-dione (83 mg) in ethanol (25 ml) was stirred at 80° C. for 17 h. The mixture was then concentrated in vacuo, and the residue was recrystallized from acetonitrile.

Yield: 105 mg (as TFA salt). MS-ESI: [M+H]$^+$=508.4/510.4; anal. HPLC: R$_t$=7.65 min. (method 2)

EXAMPLE 39

4-[3-Bromo-5-fluoromethoxy-4-(pyridin-3-ylmethoxy)-phenyl]-2-methyl-5-oxo-7-propyl-1,4,5,6,7,8-hexahydro-quinoline-3-carbonitrile A mixture of the compound described in example 38b (700 mg), bromo-fluoro-methane (1557 mg) and potassium carbonate (761 mg) in DMF (10 ml) in a pressure vessel was stirred for 20 h. The mixture was diluted with ethyl acetate and washed with water. The organic layer was dried (MgSO$_4$), filtered and concentrated in vacuo. The residue was purified by chromatography on silicagel in heptane/ethyl acetate 2/8 (v/v) as eluent.

Yield: 842 mg (as TFA salt). MS-ESI: [M+H]$^+$=540.2/542.2; anal. HPLC: R$_t$=5.84 min. (method 1)

Diast. ratio: 7:1

EXAMPLE 40

4-[3-Bromo-5-(2,2-difluoro-ethoxy)-4-(pyridin-3-ylmethoxy)-phenyl]-2-methyl-5-oxo-7-propyl-1,4,5,6,7,8-hexahydro-quinoline-3-carbonitrile A mixture of the compound described in example 38b (150 mg), 2,2-difluoro-1-bromoethane (86 mg), potassium carbonate (82 mg) and a catalytic amount of tetrabutylammonium iodide in DMF (5 ml) was stirred at 40° C. for 17 h. The mixture was diluted with ethyl acetate and washed with water. The organic layer was dried (MgSO$_4$), filtered and concentrated in vacuo. The residue was purified by preparative HPLC (Method A).

Yield: 113 mg (as TFA salt). MS-ESI: [M+H]$^+$=572.2/574.2; anal. HPLC: R$_t$=10.99 min. (method 2)

EXAMPLE 41

3-Bromo-5-(3-cyano-2-methyl-5-oxo-7-propyl-1,4,5,6,7,8-hexahydro-quinolin-4-yl)-N,N-dimethyl-2-(thiazol-4-ylmethoxy)-benzenesulfonamide (a). 3-Bromo-5-(3-cyano-2-methyl-5-oxo-7-propyl-1,4,5,6,7,8-hexahydro-quinolin-4-yl)-2-hydroxy-N,N-dimethyl-benzenesulfonamide For 30 min., dimethylamine was bubbled through a solution of the compound described in example 37b (4.1 g) in dioxane (85 ml). The mixture was diluted with water and dichloromethane. In the aqueous layer, a voluminous precipitate formed, which was collected by filtration and dried in vacuo.

Yield: 2.19 g. MS-ESI: [M+H]$^+$=508.2/510.2

(b). 3-Bromo-5-(3-cyano-2-methyl-5-oxo-7-propyl-1,4,5,6,7,8-hexahydro-quinolin-4-yl)-N,N-dimethyl-2-(thiazol-4-ylmethoxy)-benzenesulfonamide A mixture of 3-bromo-5-(3-cyano-2-methyl-5-oxo-7-propyl-1,4,5,6,7,8-hexahydro-quinolin-4-yl)-2-hydroxy-N,N-dimethyl-benzenesulfonamide (200 mg), potassium carbonate (109 mg), potassium iodide (5 mg) and 4-chloromethyl-thiazole. HCl (71 mg) in DMF (4.5 ml) was heated at 60° C. for 6 h. The mixture was diluted with water and extracted with ethyl acetate. The organic layer was dried (MgSO$_4$), filtered and concentrated in vacuo. The residue was purified by preparative HPLC (Method B).

Yield: 110 mg. MS-ESI: [M+H]$^+$=605.2/607.2; anal. HPLC: R$_t$=19.62 min. (method 2)

EXAMPLE 42

3-Bromo-5-(3-cyano-2-methyl-5-oxo-7-propyl-1,4,5,6,7,8-hexahydro-quinolin-4-yl)-2-(2,5-dimethyl-2H-pyrazol-3-ylmethoxy)-N,N-dimethyl-benzenesulfonamide A mixture of the compound described in example 41a (153 mg), potassium carbonate (125 mg), and 5-chloromethyl-1,3-dimethyl-1H-pyrazole (55 mg) in DMF (1.4 ml) was heated at 60° C. for 3 h. The mixture was diluted with 1N hydrochloric acid and extracted with ethyl acetate. The organic layer was dried (MgSO$_4$), filtered and concentrated in vacuo. The residue was purified by preparative HPLC (Method B), then purified by chromatography on aluminum oxide using ethyl acetate as eluent.

Yield: 51 mg. MS-ESI: [M+H]$^+$=616.2/618.2; anal. HPLC: R$_t$=18.40 min. (method 2)

EXAMPLE 43

Agonistic Activity of Compounds at the Human FSH Receptor Expressed in CHO Cells Agonist activity of the compounds at the human FSH receptor was tested in Chinese Hamster Ovary (CHO) cells stably transfected with the human FSH receptor and cotransfected with a cAMP responsive element (CRE)/promotor directing the expression of a firefly luciferase reporter gene. Binding of the compound to the Gs-coupled FSH receptor will result in an increase of cAMP, which in turn will induce an increased transactivation of the luciferase reporter construct. The luciferase activity was quantified using a luminescence counter. The compounds were tested in the concentration range of 0.1 nM to 10 μM. This assay was used to determine the EC$_{50}$ (concentration of test compound causing half-maximal (50%) luciferase stimulation) and efficacy of the compounds compared to recombinant human FSH. For this, the software program XLfit (Excel version 2.0, built 30, ID Business Solutions Limited) was used.

The compounds described in the preceding examples all have an EC$_{50}$ of less than $5.10^{-6}$ M. Some of the compounds, such as those of examples 2, 10, 17, 19, 20, 24, 30-32, 36, 37, and 39-42 showed an EC$_{50}$ of less than $10^{-8}$ M.

What is claimed:

1. A 4-phenyl-5-oxo-1,4,5,6,7,8-hexahydroquinoline derivative according to Formula I,

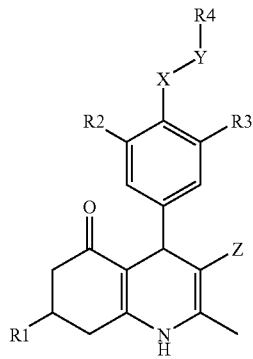

Formula I wherein
R$^1$ is (1-6C)alkyl, (2-6C)alkenyl or (2-6C)alkynyl;
R$^2$ is halogen, (1-4C)alkoxy, fluorinated (1-4C)alkoxy, (1-4C)alkyl, or fluorinated (1-4C)alkyl; or R$^2$ may be H when R$^3$ is R$^9$,R$^{10}$-aminosulfonyl;
R$^3$ is OH, NO$_2$, CN, fluorinated (1-4C)alkoxy, (1-4C)alkoxy(2-4C)alkoxy, hydroxy(2-4C)alkoxy, (1-4C)alkoxycarbonyl, (3-4C)alkenyloxycarbonyl, (1-4C)alkoxycarbonyloxy, (3-4C)alkenyloxycarbonyloxy, R$^7$,R$^8$-amino, R$^9$,R$^{10}$-amino, R$^9$,R$^{10}$-aminocarbonyl, R$^9$,R$^{10}$-aminosulfonyl or phenyl(1-4C)alkoxy, wherein the phenyl ring is optionally substituted with one or more substituents selected from hydroxy, amino, halogen, nitro, trifluoromethyl, cyano, (1-4C)alkyl, (2-4C)alkenyl, (2-4C)alkynyl, (1-4C)alkoxy, (di)(1-4C)alkylamino;

$R^4$ is $R^{11}$-phenyl or $R^{11}$-(2-5C)heteroaryl, wherein the phenyl or heteroaryl group is optionally further substituted with one or more substituents selected from hydroxy, amino, halogen, nitro, trifluromethyl, cyano, (1-4C)alkyl, (1-4C)alkylthio, (1-4C)alkoxy, (2-4C)alkenyl, (2-4C)alkynyl;

$R^7$ is H, (1-4C)alkyl;

$R^8$ is (1-4C)alkylsulfonyl, (1-4C)alkylcarbonyl, (2-4C)alkenylcarbonyl, (3-6C)cycloalkylcarbonyl, (1-4C)alkoxycarbonyl, (3-4C)alkenyloxycarbonyl, (1-4C)alkoxy(1-4C)alkylcarbonyl, (3-4C)alkenyloxy(1-4C)alkylcarbonyl phenylcarbonyl, (2-5C)heteroarylcarbonyl, phenyl(1-4C)alkylcarbonyl, (2-5C)heteroaryl(1-4C)alkylcarbonyl, wherein the phenyl ring or the heteroaromatic ring is optionally substituted with one or more substituents selected from hydroxy, amino, halogen, nitro, trifluoromethyl, cyano, (1-4C)alkyl, (2-4C)alkenyl, (2-4C)alkynyl, (1-4C)alkoxy, (di)(1-4C)alkylamino;

$R^9$ and $R^{10}$ are independently selected from H, (1-6C)alkyl, (3-6C)cycloalkyl, (3-6C)cycloalkyl(1-4C)alkyl and (1-4C)alkoxy(2-4C)alkyl;

or $R^9$ and $R^{10}$ may be joined in a (4-6C)heterocycloalkenyl ring or a (2-6C)heterocycloalkyl ring, optionally substituted with one or more (1-4C)alkyl substituents;

$R^{11}$ is H, (1-6C)alkoxycarbonyl, $R^{12}$,$R^{13}$-amino, (1-6C)alkylcarbonyl, (1-6C)alkylsulfonyl, $R^{14}$-oxy, $R^{14}$,$R^{15}$-amino, $R^{14}$,$R^{15}$-aminocarbonyl, $R^{14}$,$R^{15}$-aminosulfonyl;

$R^{12}$ is H, (1-4C)alkyl;

$R^{13}$ is (1-4C)alkylsulfonyl, (1-4C)alkylcarbonyl, (3-6C)cycloalkylcarbonyl, (1-4C)alkoxycarbonyl, (3-4C)alkenyloxycarbonyl, (di)(1-4C)alkylamino-(1-4C)alkylcarbonyl, (2-6C)heterocycloalkyl(1-4C)alkylcarbonyl, (4-6C)heterocyclo-alkenyl(1-4C)alkylcarbonyl or (1-4C)alkoxy(1-4C)alkylcarbonyl;

$R^{14}$ and $R^{15}$ are independently selected from H, (1-6C)alkyl, (3-4C)alkenyl, (3-4C)alkynyl, (3-6C)cycloalkyl, (3-6C)cycloalkyl(1-4C)alkyl, hydroxy(2-4C)alkyl, amino(2-4C)alkyl, (1-4C)alkoxy(2-4C)alkyl, (di)(1-4C)alkylamino(2-4C)alkyl, (2-6C)heterocycloalkyl(2-4C)alkyl, (4-6C)heterocycloalkenyl(2-4C)alkyl, phenyl(1-4C)alkyl and (2-5C)heteroaryl(1-4C)alkyl;

X is O or $R^{16}$—N;

Y is $CH_2$, C(O) or $SO_2$;

Z is CN or $NO_2$;

$R^{16}$ is H, (1-4C)alkyl, (1-4C)alkylcarbonyl;

or a pharmaceutically acceptable salt thereof.

2. The 4-phenyl-5-oxo-1,4,5,6,7,8-hexahydroquinoline derivative according to claim 1, wherein $R^1$ is (1-6C)alkyl.

3. The 4-phenyl-5-oxo-1,4,5,6,7,8-hexahydroquinoline derivative according to claim 1, wherein $R^2$ is halogen.

4. The 4-phenyl-5-oxo-1,4,5,6,7,8-hexahydroquinoline derivative according to claim 1, wherein $R^3$ is $R^9$,$R^{10}$-aminosulfonyl.

5. The 4-phenyl-5-oxo-1,4,5,6,7,8-hexahydroquinoline derivative according to claim 4, wherein $R^9$ and $R^{10}$ are independently (1-6C)alkyl.

6. The 4-phenyl-5-oxo-1,4,5,6,7,8-hexahydroquinoline derivative according to claim 1, wherein $R^4$ is $R^{11}$-phenyl or $R^{11}$-(2-5C)heteroaryl, wherein the phenyl or heteroaryl group is optionally further substituted with one (1-4C)alkoxy.

7. The 4-phenyl-5-oxo-1,4,5,6,7,8-hexahydroquinoline derivative according to claim 6, wherein $R^{11}$ is H or $R^{12}$,$R^{13}$-amino.

8. The 4-phenyl-5-oxo-1,4,5,6,7,8-hexahydroquinoline derivative according to claim 1, wherein Z is CN.

9. The 4-phenyl-5-oxo-1,4,5,6,7,8-hexahydroquinoline derivative according to claim 1, wherein X is O.

10. The 4-phenyl-5-oxo-1,4,5,6,7,8-hexahydroquinoline derivative according to claim 1, wherein Y is $CH_2$.

11. A pharmaceutical composition comprising a 4-phenyl-5-oxo-1,4,5,6,7,8-hexahydroquinoline derivative or a pharmaceutically acceptable salt thereof according to claim 1, and pharmaceutically suitable auxiliaries.

* * * * *